United States Patent
DeWeille et al.

(12)

(10) Patent No.: US 6,287,859 B1
(45) Date of Patent: Sep. 11, 2001

(54) IDENTIFICATION, FUNCTIONAL EXPRESSION AND CHROMOSAL LOCALIZATION OF A SUSTAINED HUMAN PROTON-GATED CATION CHANNEL

(75) Inventors: Jan R. DeWeille, Valbonne; Frederic Bassilana; Michel Lazdunski, both of Nice; Waldmann Rainer, Les Adrets de l'Ester, all of (FR)

(73) Assignee: Centre National de la Recherche (FR)

( * ) Notice: Subject to any disclaimer, the term of this patent is extended or adjusted under 35 U.S.C. 154(b) by 0 days.

(21) Appl. No.: 09/360,197

(22) Filed: Jul. 23, 1999

Related U.S. Application Data

(63) Continuation-in-part of application No. 09/129,758, filed as application No. PCT/FR98/00270 on Feb. 11, 1998.
(60) Provisional application No. 60/095,408, filed on Aug. 5, 1998.

(51) Int. Cl.[7] .............................. C12N 15/12; C12N 5/10; A61K 38/17
(52) U.S. Cl. ........................ 435/375; 435/375; 435/320.1; 435/325; 435/326; 435/69.1; 514/3; 514/23; 514/397
(58) Field of Search .................................. 514/3, 23, 397; 424/610, 686, 717; 435/69.1, 252.3, 320.1, 325, 375; 530/350

(56) References Cited

FOREIGN PATENT DOCUMENTS

99/11784 * 3/1999 (WO) .

OTHER PUBLICATIONS

Babinski et al., "Molecular Cloning and Regional Distribution of a Human Proton Receptor subunit with biphasic functional properties", Journal of Neurochemistry, vol. 22, No. 1, 1999.*

* cited by examiner

*Primary Examiner*—Karen Cochrane Carlson
*Assistant Examiner*—Patricia Robinson
(74) *Attorney, Agent, or Firm*—Schnader Harrison Segal & Lewis LLP

(57) ABSTRACT

Non inactivating or slowly inactivating proton-gated cation channels are thought to play an important role in the perception of pain that accompanies tissue acidosis. We have identified a novel human proton-gated cation channel subunit that has biphasic desensitisation kinetics with both a rapidly inactivating Na$^+$-selective and a sustained component. The protein shares 84% sequence identity with the proton-gated cation channel rASIC3 (rDRASIC) from rat sensory neurones. The biphasic desensitisation kinetics and the sequence homology suggest that this novel clone (hASIC3) is the human orthologue of rASIC3 (rDRASIC). While rASIC3 (rDRASIC) requires very acidic pH (<pH 4.5) for activation of the sustained current, the non-inactivating hASIC3 current starts to be activated when the pH decreases to below pH 6. hASIC3 is ant acid sensor and might play an important role in the detection of lasting pH changes in human. We localized the hASIC3 gene to the human chromosome 7q35, 6.4 cRad telomeric from the microsatellite AFMA082XC9.

2 Claims, 16 Drawing Sheets

Fig. 1A

Met Glu Leu Lys Thr Glu Glu Glu Val Gly Gly Val Gln Pro Val Ser Ile
                                                    Pro Val Ser Ile

Gln Ala Phe Ala Ser Ser Thr Leu His Gly Leu Ala His Ile Phe Ser Tyr
Gln Ala Phe Ala Ser Ser Thr Leu His Gly Met Ala His Ile Phe Ser Tyr

Glu Arg Ser Leu Lys Arg Ala Ala Leu Trp Ala Leu Cys Phe Leu Gly Ser Leu
Glu Arg Ser Leu Lys Arg Ala Ala Leu Trp Ala Leu Cys Phe Leu Gly Ser Leu

Ala Val Leu Leu Cys Val Cys Thr Glu Arg Val Gln Tyr Tyr Phe Cys Tyr His
Ala Val Leu Leu Cys Val Cys Thr Glu Arg Val Gln Tyr Tyr Phe His Tyr His

His Val Thr Lys Leu Asp Val Ala Ala Ser Gln Leu Thr Phe Pro Pro Ala Val
His Val Thr Lys Leu Asp Val Ala Ala Ser Gln Leu Thr Phe Pro Pro Ala Val

Thr Leu Cys Asn Leu Asn Glu Phe Arg Phe Ser Gln Val Ser Lys Asn Asp Leu
Thr Leu Cys Asn Leu Asn Glu Phe Arg Phe Ser Gln Val Ser Lys Asn Asp Leu

Tyr His Ala Gly Leu Leu Ala Leu Asn Asn Arg Tyr Glu Ile Pro Asp
Tyr His Ala Gly Leu Leu Ala Leu Asn Asn Arg Tyr Glu Ile Pro Asp

Thr Gln Met Ala Asp Glu Lys Gln Ile Leu Gln Asp Lys Ala Asn Phe
Thr Gln Met Ala Asp Glu Lys Gln Ile Leu Gln Asp Lys Ala Asn Phe

Arg Ser Phe Pro Lys Pro Phe Asn Met Arg Glu Phe Tyr Asp Arg Ala Gly
Arg Ser Phe Pro Lys Pro Phe Asn Met Arg Glu Phe Tyr Asp Arg Ala Gly

His Asp Ile Arg Asp Met Leu Leu Ser Cys His Phe Arg Gly Gly Ala Cys Ser
His Asp Ile Arg Asp Met Leu Leu Ser Cys His Phe Arg Gly Val Cys Ser

Ala Gly Asp Phe Lys Val Val Phe Thr Arg Tyr Gly Lys Cys Tyr Thr Phe Asn
Ala Glu Asp Phe Lys Val Val Phe Thr Arg Tyr Gly Lys Cys Tyr Thr Phe Asn

Ser Gly Gln Asp Gly Arg Pro Arg Leu Lys Thr Met Lys Gly Thr Gly Asn
Ser Gly Asn Arg Ala Pro Arg Leu Lys Thr Met Lys Gly Thr Gly Asn

Gly Leu Glu Ile Met Leu Asp Ile Gln Gln Asp Glu Tyr Leu Pro Val Trp Gly
Gly Leu Glu Ile Met Leu Asp Ile Gln Gln Asp Glu Tyr Leu Pro Val Trp Gly

Glu Thr Asp Glu Thr Ser Phe Glu Ala Gly Ile Lys Val Gln Ile His Ser Gln
Glu Thr Asp Glu Thr Ser Phe Glu Ala Gly Ile Lys Val Gln Ile His Ser Gln

Asp Glu Pro Pro Phe Ile Asp Gln Leu Gly Phe Gly Val Ala Pro Gly Phe Gln
Asp Glu Pro Pro Phe Ile Asp Gln Leu Gly Phe Gly Val Ala Pro Gly Phe Gln

Fig. 1B (suite)

```
Thr Phe Val Ser Cys Gln Glu Gln Arg Leu Ile Tyr Leu Pro Ser Pro Trp Gly
Thr Phe Val Ser Cys Gln Glu Gln Arg Leu Ile Tyr Leu Pro Ser Pro Trp Gly

Thr Cys Asn Ala Val Thr Met Asp Ser         Asp Phe Phe Phe Asp Ser Tyr Ser
Thr Cys Lys Ala Val Thr Met Asp Ser Asp Leu Asp Phe Phe Phe Asp Ser Tyr Ser

Ile Thr Ala Cys Arg Ile Asp Cys Glu Thr Arg Tyr Leu Val Glu Asn Cys Asn
Ile Thr Ala Cys Arg Ile Asp Cys Glu Thr Arg Tyr Leu Val Glu Asn Cys Asn

Cys Arg Met Val His Met Pro Gly Asp Ala Pro Tyr Cys Thr Pro Glu Gln Tyr
Cys Arg Met Val His Met Pro Gly Asp Ala Pro Tyr Cys Thr Pro Glu Gln Tyr

Lys Glu Cys Ala Asp Pro Ala Leu Asp Phe Leu Val Glu Lys Asp Gln Glu Tyr
Lys Glu Cys Ala Asp Pro Ala Leu Asp Phe Leu Val Glu Lys Asp Gln Glu Tyr

Cys Val Cys Glu Met Pro Cys Asn Leu Thr Arg Tyr Gly Lys Glu Leu Ser Met
Cys Val Cys Glu Met Pro Cys Asn Leu Thr Arg Tyr Gly Lys Glu Leu Ser Met

Val Lys Ile Pro Ser Lys Ala Ser Leu Tyr Leu Ala Lys Phe Asn Lys
Val Lys Ile Pro Ser Lys Ala Ser Leu Tyr Leu Ala Lys Phe Asn Lys

Ser Glu Gln Tyr Ile Gly Glu Asn Ile Leu Val Leu Asp Ile Phe Phe Glu Val
Ser Glu Gln Tyr Ile Gly Glu Asn Ile Leu Val Leu Asp Ile Phe Phe Glu Val

Leu Asn Tyr Glu Thr Ile Gln Lys Lys Lys Ala Tyr Glu Ile Ala Gly Leu Leu
Leu Asn Tyr Glu Thr Ile Gln Lys Lys Lys Ala Tyr Glu Ile Ala Gly Leu Leu

Gly Asp Ile Gly Gly Gln Met Gly Leu Phe Ile Gly Ala Ser Ile Leu Thr Val
Gly Asp Ile Gly Gly Gln Met Gly Leu Phe Ile Gly Ala Ser Ile Leu Thr Val

Leu Glu Leu Phe Asp Tyr Ala Tyr Glu Val Ile Lys His Arg Leu Cys Arg Arg
Leu Glu Leu Phe Asp Tyr Ala Tyr Glu Val Ile Lys His Arg Leu Cys Arg Arg

Gly Lys Cys Gln Lys Glu Ala Lys Arg Ser Ala Asp Lys Gly Val Ala Leu
Gly Lys Cys Gln Lys Glu Ala Lys Arg Ser Ala Asp Lys Gly Val Ala Leu

Ser Leu Asp Asp Val Lys Arg His Asn Pro Cys Glu Ser Leu Arg Gly His Pro
Ser Leu Asp Asp Val Lys Arg His Asn Pro Cys Glu Ser Leu Arg Gly His Pro

Ala Gly Met Thr Tyr Ala Ala Asn Ile Leu Pro His His Pro Ala Arg Gly Thr
Ala Gly Met Thr Tyr Ala Ala Asn Ile Leu Pro His His Pro Ala Arg Gly Thr

Phe Glu Asp Phe Thr Cys
Phe Glu Asp Phe Thr Cys
```

Fig. 2A

Fig. 2B
(suite)

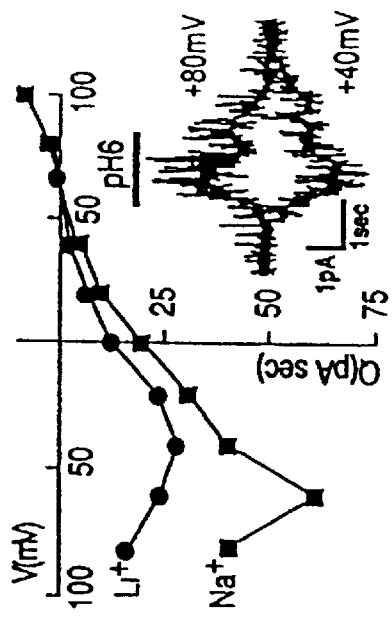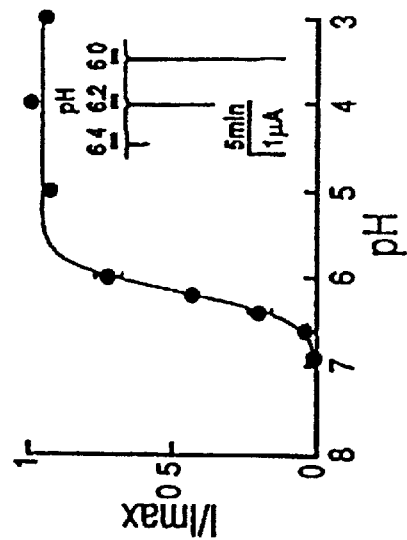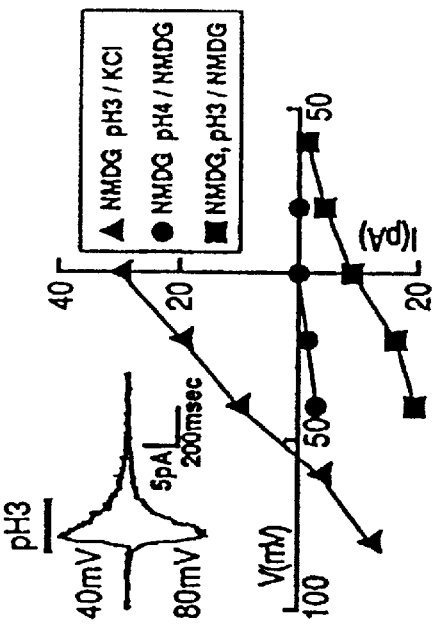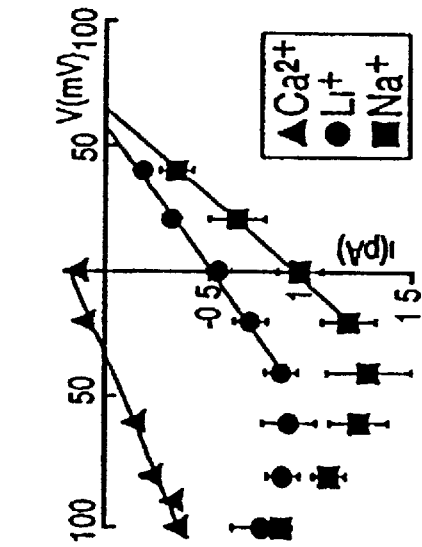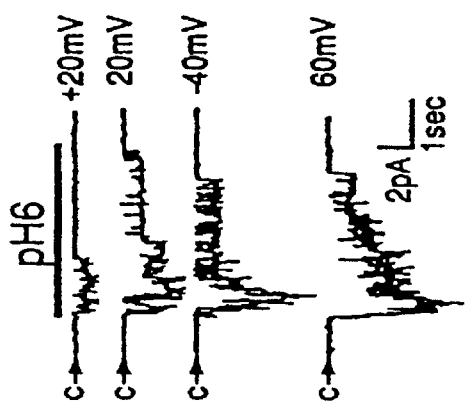

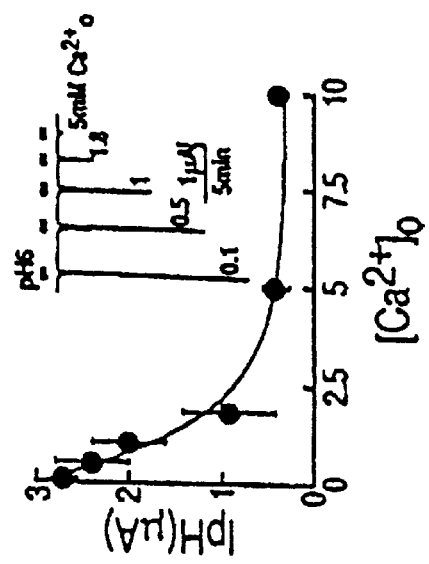
Fig. 6A
Fig. 6B
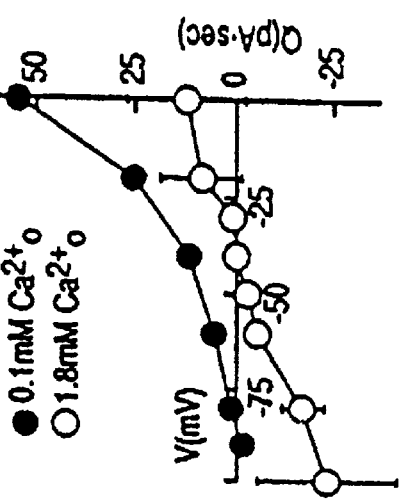
Fig. 6C
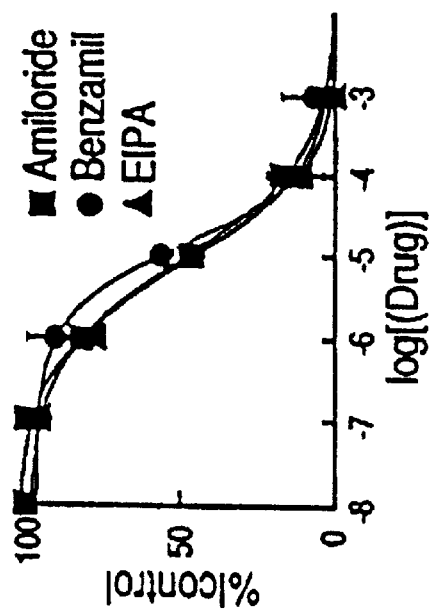
Fig. 6D
Fig. 6E ◀ 4.3 kB

Fig. 9A

Human ASIC3 Sequence

```
            10                    30                    50
ACGACGGGGTTCTGGCCATGAAGCCCACCTCAGGCCCAGAGGAGGCCCGGCGGCCAGCCT
                   M   K   P   T   S   G   P   E   E   A   R   R   P   A   S 70                    90                   110
CGGACATCCGCGTGTTCGCCAGCAACTGCTCGATGCACGGGCTGGGCCACGTCTTCGGGC
 D   I   R   V   F   A   S   N   C   S   M   H   G   L   G   H   V   F   G   P 130                   150                   170
CAGGCAGCCTGAGCCTGCGCCGGGGGATGTGGGCAGCGGCCGTGGTCCTGTCAGTGGCCA
  G   S   L   S   L   R   R   G   M   W   A   A   A   V   V   L   S   V   A   T 190                   210                   230
CCTTCCTCTACCAGGTGGCTGAGAGGGTGCGCTACTACAGGGAGTTCCACCACCAGACTG
  F   L   Y   Q   V   A   E   R   V   R   Y   Y   R   E   F   H   H   Q   T   A 250                   270                   290
CCCTGGATGAGCGAGAAAGCCACCGGCTCATCTTCCCGGCTGTCACCCTGTGCAACATCA
  L   D   E   R   E   S   H   R   L   I   F   P   A   V   T   L   C   N   I   N 310                   330                   350
ACCCACTGCGCCGCTCGCGCCTAACGCCCAACGACCTGCACTGGGCTGGGTCTGCGCTGC
  P   L   R   R   S   R   L   T   P   N   D   L   H   W   A   G   S   A   L   L 370                   390                   410
TGGGCCTGGATCCCGCAGAGCACGCCGCCTTCCTGCGCGCCCTGGGCCGGCCCCCTGCAC
  G   L   D   P   A   E   H   A   A   F   L   R   A   L   G   R   P   P   A   P 430                   450                   470
CGCCCGGCTTCATGCCCAGTCCCACCTTTGACATGGCGCAACTCTATGCCCGTGCTGGGC
  P   G   F   M   P   S   P   T   F   D   M   A   Q   L   Y   A   R   A   G   H
```

Fig. 9B-1
(suite)

```
              490                  510                 530
ACTCCCTGGATGACATGCTGCTGGACTGTCGCTTCCGTGGCCAACCTTGTGGGCCTGAGA
  S   L   D   D   M   L   L   D   C   R   F   R   G   Q   P   C   G   P   E   N 550                  570                 590
ACTTCACCACGATCTTCACCCGGATGGGAAAGTGCTGCACATTTAACTCTGGCGCTGATG
  F   T   T   I   F   T   R   M   G   K   C   Y   T   F   N   S   G   A   D   G 610                  630                 650
GGGCAGAGCTGCTCACCACTACTAGGGGTGGCATGGGCAATGGGCTGGACATCATGCTGG
  A   E   L   L   T   T   T   R   G   G   M   G   N   G   L   D   I   M   L   D 670                  690                 710
ACGTGCAGCAGGAGGAATATCTACCTGTGTGGAGGGACAATGAGGAGACCCCGTTTGAGG
  V   Q   Q   E   E   Y   L   P   V   W   R   D   N   E   E   T   P   F   E   V 730                  750                 770
TGGGGATCCGAGTGCAGATCCACAGCCAGGAGGAGCCGCCCATCATCGATCAGCTGGGCT
  G   I   R   V   Q   I   H   S   Q   E   E   P   P   I   I   D   Q   L   G   L 790                  810                 830
TGGGGGTGTCCCCGGGCTACCAGACCTTTGTTTCTTGCCAGCAGCAGCAGCTGAGCTTCC
  G   V   S   P   G   Y   Q   T   F   V   S   C   Q   Q   Q   Q   L   S   F   L 850                  870                 890
TGCCACCGCCCTGGGGCGATTGCAGTTCAGCATCTCTGAACCCCAACTATGAGCCAGAGC
  P   P   P   W   G   D   C   S   S   A   S   L   N   P   N   Y   E   P   E   P 910                  930                 950
CCTCTGATCCCCTAGGCTCCCCCAGCCCCAGCCCCAGCCCTCCCTATACCCTTATGGGGT
  S   D   P   L   G   S   P   S   P   S   P   P   Y   T   L   M   G   C
```

Fig. 9B-2
(suite)

```
        970                 990                1010
GTCGCCTGGCCTGCGAAACCCGCTACGTGGCTCGGAAGTGCGGCTGCCGAATGGTGTACA
 R   L   A   C   E   T   R   Y   V   A   R   K   C   G   C   R   M   V   Y   M 1030                1050                1070
TGCCAGGCGACGTGCCAGTGTGCAGCCCCCAGCAGTACAAGAACTGTGCCCACCCGGCCA
 P   G   D   V   P   V   C   S   P   Q   Q   Y   K   N   C   A   H   P   A   I 1090                1110                1130
TAGATGCCATGCTTCGCAAGGACTCGTGCGCCTGCCCCAACCCGTGCGCCAGCACGCGCT
 D   A   M   L   R   K   D   S   C   A   C   P   N   P   C   A   S   T   R   Y 1150                1170                1190
ACGCCAAGGAGCTCTCCATGGTGCGGATCCCGAGCCGCGCCGCCGCGCGCTTCCTGGCCC
 A   K   E   L   S   M   V   R   I   P   S   R   A   A   A   R   F   L   A   R 1210                1230                1250
GGAAGCTCAACCGCAGCGAGGCCTACATCGCGGAGAACGTGCTGGCCCTGGACATCTTCT
 K   L   N   R   S   E   A   Y   I   A   E   N   V   L   A   L   D   I   F   F 1270                1290                1310
TTGAGGCCCTCAACTATGAGACCGTGGAGCAGAAGAAGGCCTATGAGATGTCAGAGCTGC
 E   A   L   N   Y   E   T   V   E   Q   K   K   A   Y   E   M   S   E   L   L 1330                1350                1370
TTGGTGACATTGGGGGCCAGATGGGGCTGTTCATCGGGGCCAGCCTGCTCACCATCCTCG
 G   D   I   G   G   Q   M   G   L   F   I   G   A   S   L   L   T   I   L   E 1390                1410                1430
AGATCCTAGACTACCTCTGTGAGGTGTTCCGAGACAAGGTCCTGGGATATTTCTGGAACC
 I   L   D   Y   L   C   E   V   F   R   D   K   V   L   G   Y   F   W   N   R
```

Fig. 9B-3
(suite)

Fig. 10A
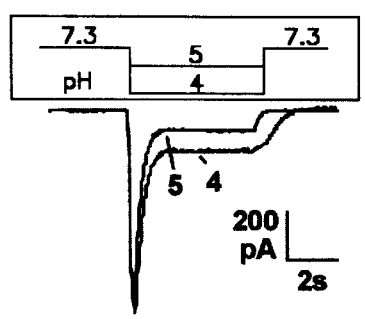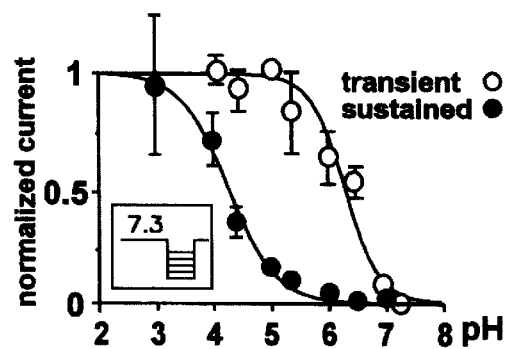
Fig. 10B
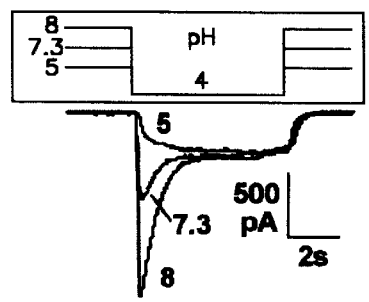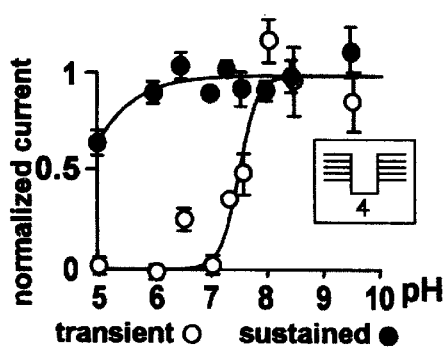
Fig. 10C
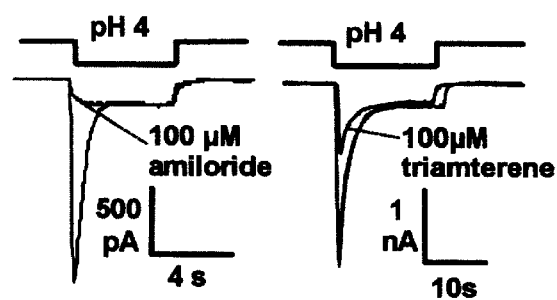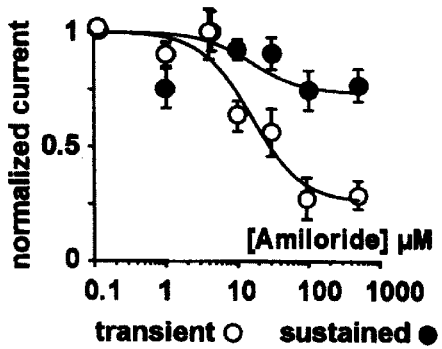

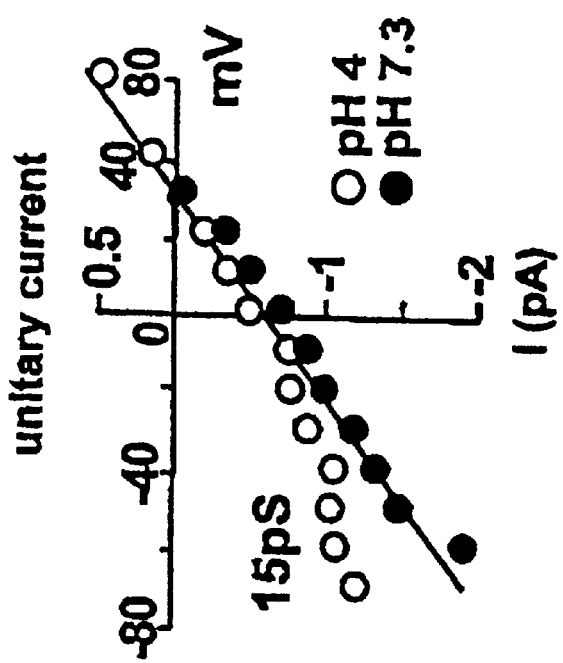
Fig. 11B
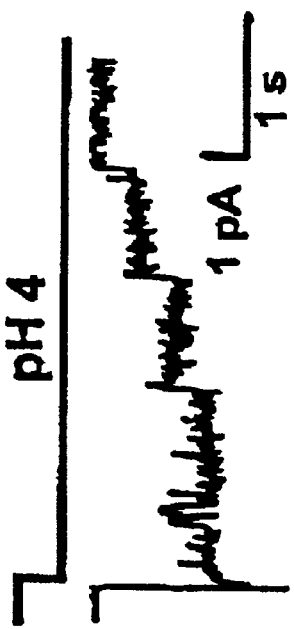
Fig. 11D
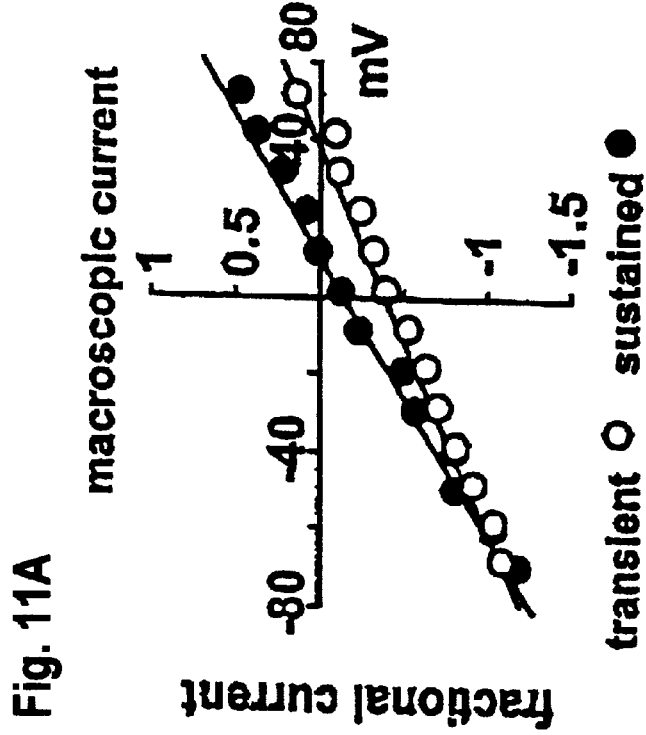
Fig. 11A
Fig. 11C

IDENTIFICATION, FUNCTIONAL EXPRESSION AND CHROMOSAL LOCALIZATION OF A SUSTAINED HUMAN PROTON-GATED CATION CHANNEL

CROSS-REFERENCE TO RELATED PATENT APPLICATIONS

This patent application is a continuation-in-part of U.S. application Ser. No. 09/129,758 filed Aug. 5, 1998 which is a 371 of PCT/FR98/00270 filed Feb. 11, 1998; and the said U.S. application is incorporated herein by reference in its entirety; and said Ser. No. 09/129,758 application claims benefit of provisional application 60/095,908 filed Aug. 5, 1998.

BACKGROUND OF THE INVENTION

FIELD OF THE INVENTION

The present invention relates to new families of mammalian, notably human and rat, acidity-sensitive ionic channels. More particularly, the invention relates to the identification and molecular characterization in humans and rats of a new family of proton-activated cationic channels, collectively referred to below as ASIC polypeptides, for Acid Sensing Ionic Channel.

The ASIC channels constitute the first members of a group of cationic channels belonging to the family of amiloride-sensitive degenerine sodium channels [6, 11–14], which are activated temporarily by extracellular acidification.

Sensitivity to acid is associated with both nociception [1] and the transduction of taste [2]. The stimulation of sensory neurons by acids is of great importance because acidity accompanies numerous painful inflammatory and ischemic situations. The pain caused by acids is thought to be mediated by the cationic channels present at the level of the sensory neurons which are activated by protons [3–5]. The biophysical and pharmacological properties of the ASIC channels of the invention are similar to those of the proton-activated cationic channels described in the sensory neurons [3, 15, 16]. However, as will be seen in the description below, to date there has been no report of ligand-activated ionic channels simpler than the ASIC channels.

SUMMARY OF THE INVENTION

The invention also relates to hybrid cationic channels constituted by the combination of a first protein comprising a proton-activated ionic channel according to the invention with a second proton-activated ionic channel.

The present invention has as its object a nucleic acid molecule coding for a protein constitutung a neuronal neuronal cationic channels that is sensitive to amiloride and activated by protons.

The invention also relates to a vector comprising at least one of the preceding nucleic acid molecules, advantageously combined with suitable control sequences, as well as a procedure for production or expression in a cell host of a protein constituting an ionic channel according to the Invention.

The invention also relates to the transformed cells expressing ASIC cation channels and/or their derivatives obtained according to the preceding methods.

The present invention also relates to application of the ASIC channel for studying pathological modifications that may lead to neuronal degenerations. The invention this also relates to the pharmaceutical preparations comprising as an active ingredient, at least one of these proteins of the invention.

Other characteristics and advantages of the invention will be seen in the description below related to research activities that led to the demonstration and the characterization of the ASIC channel.

This invention can be further understood with reference to the Figures, discussed next and in the Examples.

BRIEF DESCRIPTION OF THE FIGURES

FIG. 1 represents the alignment of the sequences of the rat ASIC proteins (at top) and human ASIC proteins (at bottom) of sequences SEQ ID NO: 1 and SEQ ID NO: 2.

FIG. 2 represents a comparison of the protein sequence of the rASIC1A channel with the sequence of other ionic channels:

FIG. 5 shows the biophysical properties of the proton-activated rASIC1A channel.

FIG. 6 shows the effect of $Ca^{2+}$ and of amiloride on the rASIC1A current.

FIG. 9 shows the alignment of the deduced protein sequences of hASIC3 and rASIC3.

FIG. 10 shows the pH dependence and pharmacology of hASIC3.

FIG. 11 shows the selectivity and single channel properties of hASIC3.

IDENTIFICATION OF THE AMINO ACID AND DNA SEQUENCES

Figure 3:
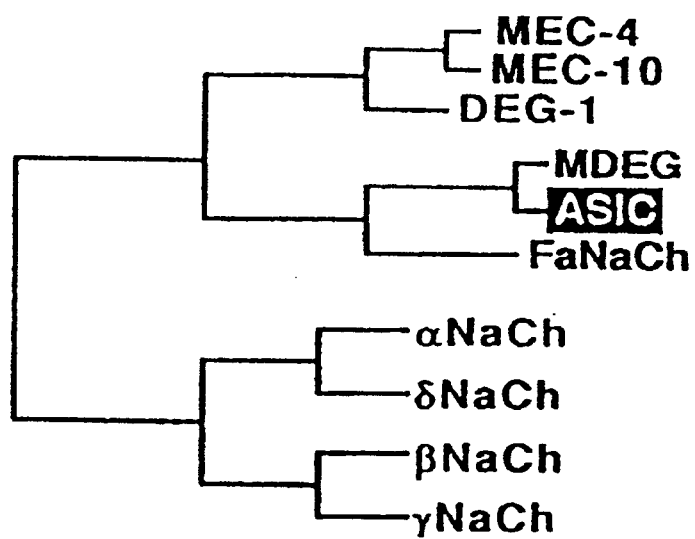
FIG. 3 represents the phylogenetic tree of the proteins of the subunits αNaCh, βNaCh, γNaCh, δNaCh of the amiloride-sensitive sodium channel and of the degenerines MEC-4, MEC-10 and DEG-1 of *C. elegans*.

SEQ ID NO: 1 represents the sequence of 526 amino acids of the protein of the rASIC1A channel deduced from the cDNA sequence of the rat.

SEQ ID NO: 2 represents the partial sequence of 514 amino acids of the protein of the hASIC1A channel deduced from the partial sequence of human cDNA.

SEQ ID NO: 3 represents the sequence of 512 amino acids of the protein of the hASIC2A channel deduced from the sequence of human cDNA.

SEQ ID NO: 4 represents the sequence of 559 amino acids of the protein of the rASIC1B channel as well as the sequence of a DNA molecule comprising the sequence coding for that protein.

SEQ ID NO: 5 represents the sequence of 533 amino acids of the protein of the rASIC3 channel and the sequence of DNA coding for that protein.

SEQ ID NO: 6 represents the sequence of 563 amino acids of the protein of the rASIC2B channel as well as the sequence of a DNA molecule comprising the sequence coding for that protein.

SEQ ID NO: 7 represents the sequence of 533 amino acids of the protein of the hASIC3 channel as well as the sequence of a DNA molecule comprising the sequence coding for that protein.

DETAILED DESCRIPTION OF THE INVENTION

The present invention has as its object and rat protiens constituting neuronal cationic channels that are sensitive to amiloride and which are activated by protons. The invention relates to proteins constituting the ASIC family of cation channels, or functionality equivalent derivatives of these proteins.

Such derivatives are those polypeptides whose sequence includes a modification and/or a suppression and/or an addition of one or more amino acid residues, as long as this modification, suppression, and/or addition does not alter the functional and structural properties of the ASIC channel, principally its activation by protons. Indeed, three different ASIC polypeptides, ASIC1, ASIC2 and ASIC3, in both rat and human, are described herein. In addition, the transcripts encoding ASIC1 and ASIC2 are alternatively spliced, which generates additional functional derivatives of the ASIC1 and ASIC2 proteins (ASIC1A and 1B, ASIC2A and ASIC2B, respectively). Other functional derivatives of the ASIC proteins and/or other forms of the ASIC polypeptides generated by alternative splicing of the ASIC mRNA transcripts are considered to be within the scope of the present invention. Such proteins and their functional derivatives can be analyzed by an expert in the field using the techniques described in the Examples included herein, which make it possible to demonstrate the biophysical and pharmacological properties of the ASIC channels.

Further examples of functional derivatives of the ASIC channels are as follows: The human and rat ASIC1A proteins (hASIC1A and rASIC1A, SEQ ID Nos. 1 and 2, respectively) are considered to be functionally equivalent. The amino acid sequences of these two proteins are highly homologous, but they are not identical. Thus, substitutions can readily be introduced within the primary sequence of ASIC proteins without influencing their basic functional characteristics.

Another example of such a functionally equivalent derivative is the protein constituting a cationic channel previously designated MDEG [14] or BNaCl [20], designated herein as rASIC2A. The amino acid sequence of rASIC2A is represented in the annexed list of sequences under number SEQ ID NO: 3. rASIC2A has been described as a mammalian cationic channel which is sensitive to amiloride and which is activated in *C. elegans* by mutations that result in neurodegeneration. The rASIC2A channel is a structurally similar to the ASIC1A channel, exhibiting approximately 67% homology in their amino acid sequences. Cation transport by both polypeptides is sensitive to amiloride and regulated by acid. However, the electrophysiological properties of these two channels are different because they are not activated by the same pH changes. Thus, the range of sensitivity of rASIC2A ($EC_{50}$=4.05) is different from that of ASIC1A ($EC_{50}$=6.2). Other functionally equivalent proteins that may exhibit different electrophysiological properties are also considered to be within the scope of the invention.

It has been shown that the rASIC2A channel is activated by the same mutations as those causing neuronal degeneration in *C. elegans*. Thus, like the hyperactive mutants of *C. elegans*, the active mutants of rASIC2A are responsible for cell death. This indicates that the acquisition of function by this neuronal ionic channel could be associated with various forms of neuronal degeneration in mammals, notably of rodents and humans. However, no normal physiological function of rASIC2A was known until the demonstration of its activation by protons in accordance with the cationic channels of the present invention.

Other examples of proteins constituting a neuronal cationic channel that are sensitive to amiloride and activated by protons according to the invention are presented below:

A channel designated ASIC1B. whose sequence of 559 amino acids is represented in the annexed list of sequences under number SEQ ID NO: 4. ASIC1B is a splicing variant of the ASIC1A channel cloned from the rat brain by degenerated PCR. The first 185 amino acids are replaced by a new sequence of 218 amino acids which is underlined in SEQ ID NO: 4.

A channel designated rASIC2B. rASIC2B is a splicing variant of rASIC2A and is represented by SEQ ID No. 6.

A channel designated rASIC3, whose sequence of 533 amino acids is represented in the list of sequences under number SEQ ID NO: 5. rASIC3 was cloned from sensory neurons from the rat using a partial sequence from the data banks (Expressed Sequence Tag with accession number W62694). The properties of rASIC3 are as follows:

a) It is expressed in the sensory neurons but not in the brain.

b) Its expression in Xenopus oocytes or in mammalian cells allows recording of a proton-activated sodium current which presents two components: a component activating and inactivating itself rapidly, and a component activating itself more slowly and not inactivating itself. The two components are selective for $Na^+$. A proton-activated cationic channel that does not inactivate itself was implicated in the prolonged sensation of pain caused by acidosis.

A channel designated hASIC3, which is represented by SEQ ID No. 7. This protein is a novel human proton-gated cation channel subunit that has biphasic desensitisation kinetics, with both a rapidly inactivating $Na^+$-selective and a sustained component. The protein shares 84% sequence identity with the proton-gated cation channel rASIC3 from rat sensory neurons.

The invention also relates to hybrid cationic channels, or channels constituted by the combination of a first protein comprising a proton-activated ionic channel according to the invention with a second protein comprising a proton-activated ionic channel. Advantageously, the said second protein is also a protein comprising a proton-activated ionic channel according to the invention. An example of such a combination is illustrated by the combination of the ASIC1A, ASIC2A or ASIC3 channel with the ASIC2A channel. Such hybrid channels exhibit a third range of pH sensitivity (e.g., with ASIC: $EC_{50}$=4.8). Another example of such a hybrid channel is the combination of the ASIC1A, ASIC1B, ASIC2A or ASIC3 channels with the the ASIC2B channel.

ASIC2B is a channel that was cloned from the rat brain using a partial mouse sequence accessible in the data banks (Expressed Sequence Tag with accession number W50528) and whose sequence of 563 amino acids is represented in the annexed list of sequences under number SEQ ID NO: 6. ASIC2B is a splicing variant of ASIC2A. The first 185 amino acids are replaced by a new sequence of 236 amino acids which is underlined in SEQ ID NO: 6. ASIC2B is expressed in the brain and in the sensory neurons of the dorsal root ganglia.

ASIC2B expressed alone in Xenopus oocytes or in mammalian cells does not form a proton-activated cationic channel. However, it can combine with ASIC2A or ASIC3 to form proton-activated heteromultimeric channels with modified properties. The activation pH of the channel formed after the co-expression of ASIC2A and ASIC2B differs from the channel formed by ASIC2A alone. After expression of ASIC2A and ASIC2B in COS cells, the current has not reached its maximum value at pH 3 whereas the current induced by ASIC2A alone is saturated at a pH between 4.5 and 4.0. In addition, the inactivation kinetics and the ionic selectivity of the channel formed after the co-expression of ASIC2A and ASIC2B are clearly different from those of ASIC2A alone. A current appears which inactivates itself slowly and is barely selective for $Na^+$ and $K^+$.

In another example, the sodium current obtained after expression of ASIC3 becomes non-selective (it does not differentiate between sodium and potassium) when ASIC2B is co-expressed with ASIC3. This new property is similar to that of the proton-activated cationic channel which is implicated in the prolonged sensation of pain caused by acidosis. It is very probable that ASIC3 and ASIC2B are part of this channel.

The amino acid sequence homologies of the proteins constituting the ASIC1A, ASIC1B channels cited according to the invention are presented in Table 1 below.

TABLE 1

| Channel | ASIC 1B | ASIC 1A | ASIC2B | ASIC2A | ASIC3 |
|---|---|---|---|---|---|
| ASIC1B | 100 | 80 | 56 | 61 | 52 |
| ASIC1A | | 100 | 59 | 68 | 53 |
| ASIC2B | | | 100 | 78 | 48 |
| ASIC2A | | | | 100 | 51 |
| ASIC3 | | | | | 100 |

Polyclonal or monoclonal antibodies directed against at least one protein constituting an ion channel of the invention and/or against a hybrid channel as described above can be prepared by the classic methods described in the literature. The antibodies are useful for investigating the presence of the ionic channels of the invention in various human and animal tissues, and may also be used to inhibit or activate an ASIC channel and/or its derivatives in vivo. Such an application may be useful for the treatment of diseases arising from defective ASIC cation transport.

The present invention also has as its object a nucleic acid molecule coding for a protein constituting a neuronal cationic channel that is sensitive to amiloride and activated by protons. More particularly, the invention relates to a nucleic acid molecule comprising at least one sequence coding for a protein constituting the ASIC1A, ASIC1B, ASIC2A, ASIC2B, or ASIC3 cation channels from human or rat.

The invention also relates to a vector comprising at least one of the preceding nucleic acid molecules, advantageously combined with suitable control sequences, as well as a procedure for production or expression in a cell host of a protein constituting an ionic channel according to the invention. The preparation of these vectors as well as the production or expression of the channels of the invention in a competent host cell can be accomplished by established methods known to experts in the field.

For example, the expression and production of a protein constituting a cationic channel according to the invention can be accomplished by:

transferring a nucleic acid molecule of the invention or a vector containing said molecule into a competent host cell, culturing said host cell host under conditions allowing expression of the ionic channels of the invention.

isolating the proteins constituting the ionic channels of the invention.

The host cell employed in the preceding methods can be selected from among the prokaryotes or the eukaryotes and notably from among the bacteria, yeasts or cells of mammals, plants or insects.

The vector used is selected in relation to the host to which it will be transferred; any vector such as a plasmid can be used.

The invention also relates to the transformed cells expressing ASIC cation channels and/or their derivatives obtained according to the preceding methods. These cells are useful for screening to identify substances that are capable of modulating cation transport by these polypwptides and hence, the perception of acidity with regard to both nociception and taste transduction. This screening is implemented by bringing variable quantities of a substance to be tested into contact with cells expressing the ASIC channels and determining the effects of said substance on the currents of said cation channels. These screenings allow for the identification of new drugs that are useful in the treatment or prevention of pain. They also enable the identification and investigation of agents that modulate acid taste. In addition, these methods are useful for identifying substances that block, or can inhibit neurodegeneration induced by hyperexpression of these channels. The substances which are isolated and detected by means of the methods above are also part of the invention. The ASIC channels clearly have ionic selectivity properties, notably with regard to their selective permeability by sodium, potassium and calcium, which endows them with excitotoxic properties when hyperstimulated.

A protein constituting an ASIC neuronal ionic channel can also be useful for developing drugs intended for the treatment or prevention of pathologies entailing the painful perception of acidity which intervenes in inflammatory diseases, ischemias and a certain number of tumors. The invention thus also relates to pharmaceutical compositions comprising as active ingredients, at least one protein constituting an ionic channel according to the invention.

A nucleic acid molecule coding for a protein constituting an ASIC channel or a derivative thereof, or a vector comprising this nucleic acid molecule or a cell expressing ASIC channels are also useful for the preparation of transgenic animals. These can be animals superexpressing said channels, but also "knock-out" animals, i.e., animals deficient in the expression of these channels or of the cation transport activity of the ASIC channels. These transgenic animals are prepared by methods known to the expert in the field, and enable the development of live models for studying animal pathologies associated with ASIC channels.

The nucleic acid molecules of the invention or the cells transformed by said molecule can thus be used for genetic therapy to compensate for a deficiency in the ASIC channels at the level of one or more tissues of a patient. The invention thus relates also to a drug comprising nucleic acid molecules of the invention or cells transformed by said nucleic acid molecules for the treatment of pathology involving the ASIC channels or their derivatives.

In addition to the property of being activated by protons and the resultant applications described above relating to the perception of acidity, the ASIC channels, and particularly ASIC channels that have genetic mutations, may be involved in some neurogenerative processes. The death of certain neurons is characteristic of many types of neuronal degenerative disorders such as Alzheimer's disease, Huntington's disease, Parkinson's disease, amyotrophic lateral sclerosis and cerebellar ataxia. Studies of such neurodegenerative processes have identified only a few deficient genes that may be responsible for or associated with these diseases. It is likely that many more important genes remain to be identified. The primitive neural network of the nematode *C. elegans* constitutes a good model of neuronal development and death. The hereditary degeneration in *C. elegans* can be due to mutations of the genes deg-1, mec-4 and mec-10. These genes exhibit homology with the subunits of amiloride-sensitive sodium channels. In addition, the functional expression of the mec-4 chimeras of the epithelial sodium channel, suggest that these genes are ionic channels whose acquisition of function is the cause of neuronal degeneration.

The present invention thus also relates to application of the ASIC channel for studying these pathological modifications that may lead to neuronal degenerations. The techniques employed for these applications, for example for drug screening, are similar to those described above for the investigation of taste-modulating agents and analgesic agents.

In addition, a protein constituting an ASIC neuronal ionic channel, an agonist or an antagonist of said protein, can also be used for the fabrication of drugs intended for the treatment or prevention of pathologies involving cerebral neuronal degeneration. The invention thus also relates to the pharmaceutical preparations comprising as an active ingredient, at least one of these proteins of the invention, possibly combined with a physiologically acceptable vehicle.

More specifically, the invention relates to a chemical or biological substance that is capable of modifying the currents of an ionic channel and/or a hybrid channel according to the invention for the preparation of a drug capable of modulating the perception of acidity with regard to nociception as well as taste transduction in a human or animal subject.

Other characteristics and advantages of the invention will be seen in the description below related to research activities that led to the demonstration and the characterization of the ASIC channel, and in which reference will be made to the annexed sequences and drawings in which:

DETAILED DESCRIPTION OF THE FIGURES

FIG. 1 represents the alignment of the sequences of the rat ASIC proteins (at top) and human ASIC proteins (at bottom) of sequences SEQ ID NO: 1 and SEQ ID NO: 2. Comparison of these sequences shows the absence of 14 amino acids at the beginning of the human coding phase compared to that of the rat.

Figure 2A:
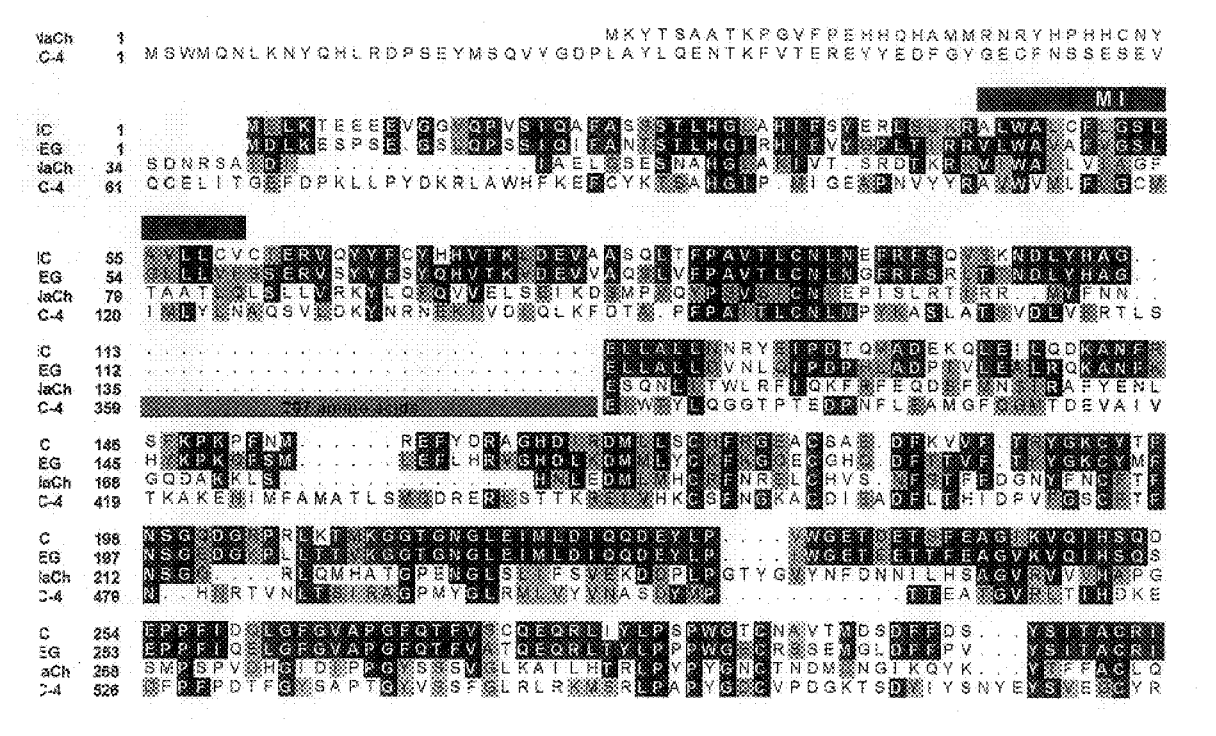
Figure 2B:
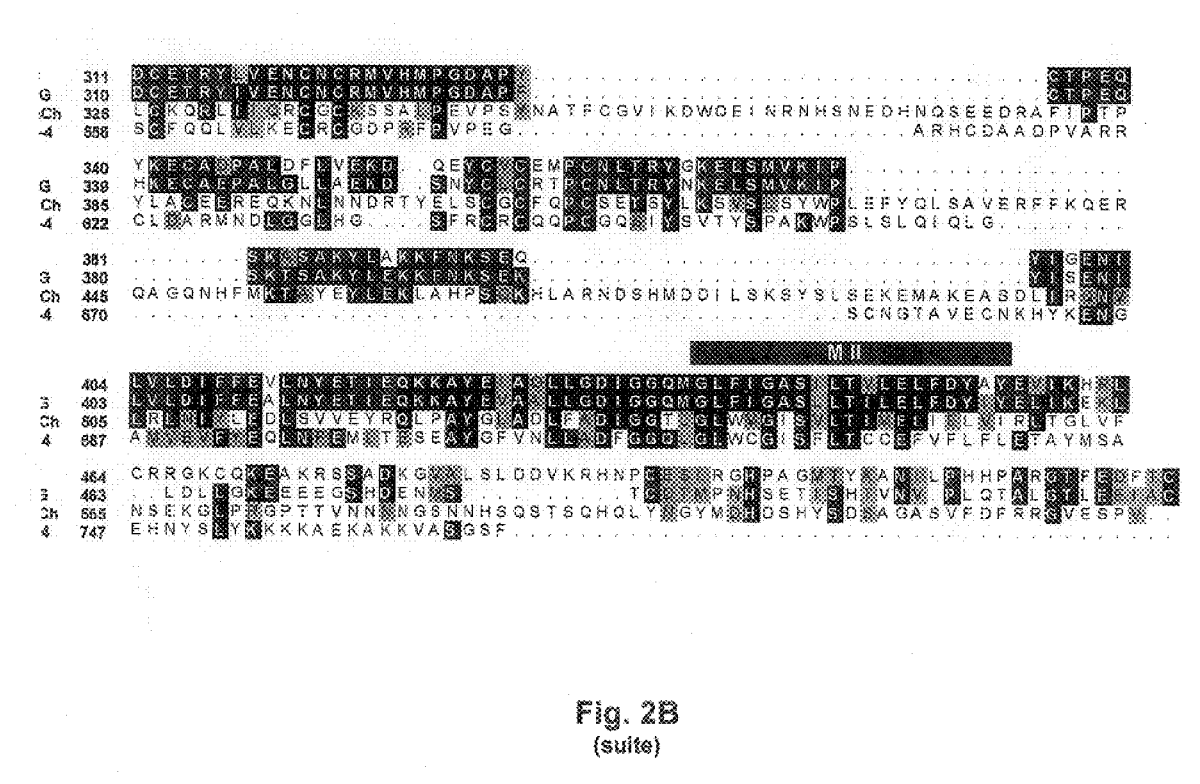

FIG. 2 represents a comparison of the protein sequence of the rASIC1A channel with the sequence of other ionic channels:

ASIC2A (MDEG) [14], a mammalian cationic channel that is activated by the mutations responsible for neuro-degenerations with the degenerines of *C. elegans*.

FaNaCh [10], a peptide of a sodium channel of *Helix aspersa* that is activated by FMRFamide.

The degenerine MEC-4 [12] of *C. elegans*.

In this figure, the residues that are identical or similar to those of ASIC are printed respectively in white on a black background and in black on a gray background. The supposed transmembranal regions (MI, MII) of rASIC1A are marked by black bars.

FIG. 3 represents the phylogenetic tree of the proteins of the subunits αNaCh, βNaCh, γNaCh, δNaCh of the amiloride-sensitive sodium channel and of the degenerines MEC-4, MEC-10 and DEG-1 of *C. elegans*.

Figure 4:
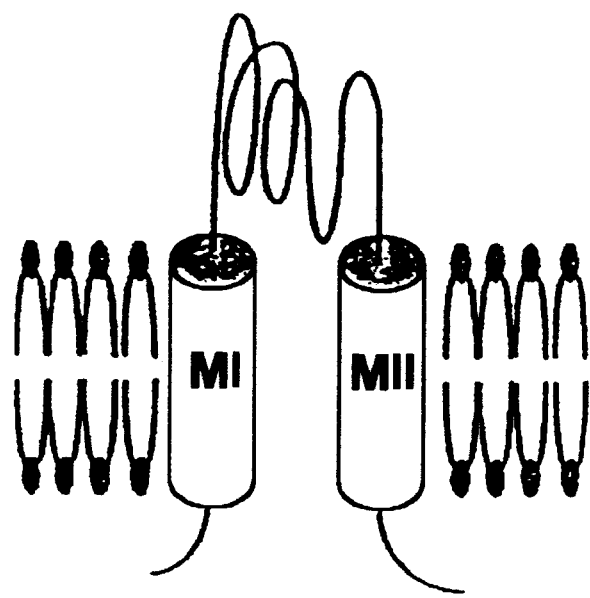
FIG. 4 represents the topology proposed for this latter family of ionic channels [30].

FIG. 4 represents the topology proposed for this latter family of ionic channels [30].

FIG. 5 shows the biophysical properties of the proton-activated rASIC1A channel.

a) the macroscopic inflowing currents recorded at −70 mV after rapid pH changes from pH 7.4 to pH 6.

b) the dose-response curve of the extracellular pH. The initial pH was 7.4 and the points represent the mean values from 6 tests. The insert in this Figure shows the typical responses at −70 mV.

c) the Q-V relations of the outside-out patch with 140 mM of $Na^+$ (■) or of $Li^+$ (●) in the bath solution. Q is the charge transported during the acid pH transition. The insert in this figure shows the typical responses in a medium containing $Na^+$.

d) the currents activated by the $H^+$ protons recorded at various potentials in an outside-out patch in a medium containing $Na^+$.

e) the mean i-V relations measured from the outside-out patch with 140 mM of $Na^+$ (■), 140 mM of $Li^+$ (●) or 1.8 mM of $Ca^{2+}$ (▲), as majority permeable ions in the external solutions; the inversion potentials were respectively 65 mV, 58 mV and −34 mV.

f) the proton current through the rASIC1A channel. The relations between the current peak and the voltage were measured from an outside-out patch in a solution of free $Na^+$, free $Ca^{2+}$ with pipettes containing a solution of free $K^+$, at pH 4 (●) and at pH 3 (■), with (▲) representing the results obtained under the same conditions as (■) but with KCl in the pipette. The insert in this figure shows the typical responses under (▲) conditions.

FIG. 6 shows the effect of $Ca^{2+}$ and of amiloride on the rASIC1A current.

a) the currents activated by the $H^+$ protons recorded at various membranal potentials from an outside-out patch with 1.8 mM of $Ca^{2+}$ in a solution of free $Na^+$; the currents were inverted at −35 mV.

b) the mean Q-V relations from an outside-out patch recorded in solutions of free $Na^+$ containing 1.8 mM of $Ca^{2+}$ (o, inversion potential −34 mV) or 0.1 mM of $Ca^{2+}$ (●, inversion potential −80 mV).

c) the effect of the external $Ca^{2+}$ on the macroscopic peak of inflowing current recorded at −70 mV and activated by a rapid pH change from pH 7.4 to pH 6. The insert in this Figure shows the typical responses. The points represent means values±se of 5 oocytes.

d) the effect of amiloride on the currents activated by the $H^+$ protons recorded at 0 mV from an outside-out patch.

e) the inhibition of the macroscopic current (induced by a pH change from pH 7.4 to pH 6) at −70 mV by amiloride and derivatives. The points represent the means values±se of 5 oocytes.

FIG. 7 shows the tissue distribution of ASIC1A channel mRNA.

a) Northern blot analysis of the mRNA expression of the hASIC1A channel in human tissues.

b) In b: RT-PCR analysis of the mRNA expression of the rASIC1A channel in the rat brain and in the dorsal root ganglion (DRG). (+), (−) represent respectively the samples with or without reverse transcriptase. The agarose gel sections were developed in 1% ethidium bromide. The arrows indicate the discounted size (657 pb) of the PCR product.

Figure 8A:
FIG. 8 shows the in situ hybridization.
Figure 8B:
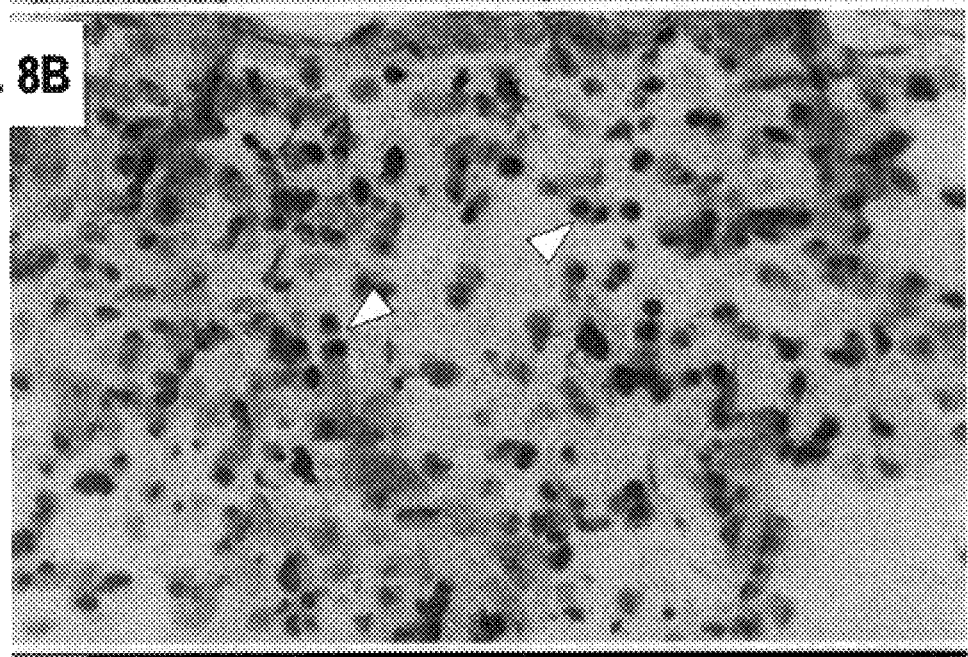

FIG. 8 shows the in situ hybridization.

a,b) hybridization of 6 μm sections of a dorsal root ganglion from a 3-year-old rat with the E probe marked with digoxigenin. In a: a low-lighting microphotograph (enlargement 30×). In b: a high-resolution image (enlargement 80×) of "a". One can see the intense marking of the small-diameter neurons (arrows). Similar results were also obtained with probes A, C and D.

c) the distribution of the rASIC1A channel mRNA in the brain of an adult rat analyzed by in situ hybridization with antisense oligonucleotide C. Identical results were obtained with oligonucleotide B. The colors indicate abundance (red: high expression; blue: not detectable). The abbreviations used in the Figure are as follows: Cer=cerebellum; Hip=hippocampus; OB=olfactory bulb; Cx=cortex.

Figure 9A:
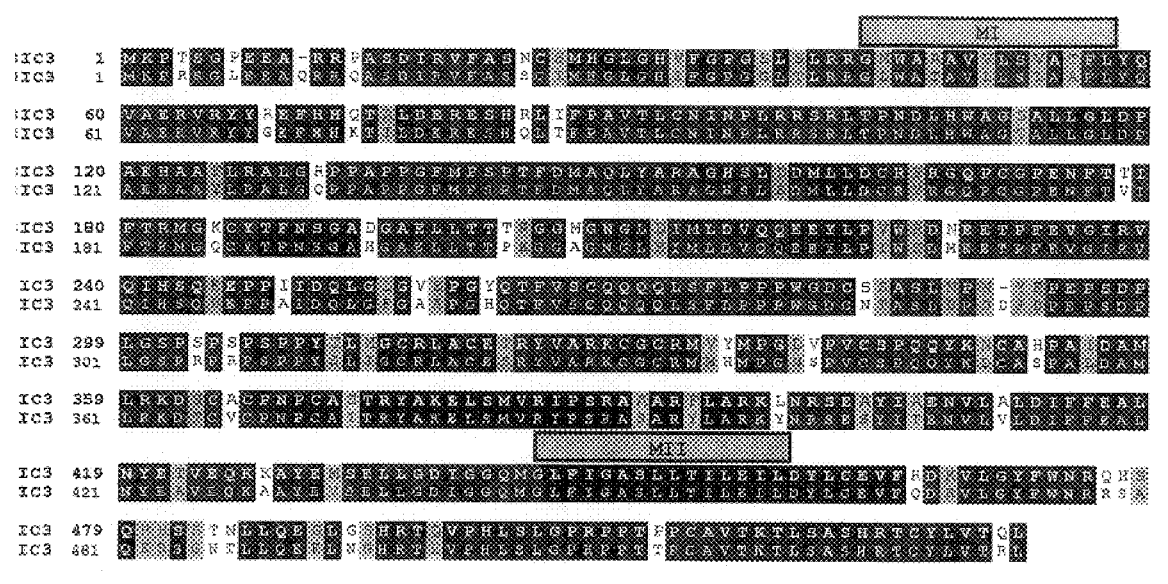

FIG. 9 shows the alignment of the deduced protein sequences of hASIC3 and rASIC3. Amino acids that are identical or similar in both sequences are printed white on black or black on grey background respectively. The two putative hydrophobic transmembrane domains are labelled with boxes. Sequences were aligned with the pileup program (Genetic Computer Group, Wisconsin).

FIG. 10 shows the pH dependence and pharmacology of hASIC3. Proton-induced membrane currents were recorded from hASIC3-transfected COS cells using the whole-cell suction-pipette technique.

a) pH dependence of the hASIC3 current. $H^+$-gated currents were induced by decreasing the extracellular pH rapidly from pH 7.3 to the pH values indicated. The pH required for half maximal activation was pH 6.2 for the transient current and pH 4.3 for the sustained current.

b) $H^+$ induced hASIC3 currents depend on the resting pH. The extracellular pH was decreased rapidly from the indicated resting pH to pH 4. The currents in A and B are shown as the fraction of the saturation level of the Bolzmann fit. c) inhibition of hASIC3 by the diuretics amiloride and triamterene. In the dose-response curve for amiloride ($K_{0.5}$=15.9 μM), currents are expressed as fraction of the mean current in the absence of drug. Data points (o, transient current; l sustained current) represent the average ±SEM of at least 5 experiments. Macroscopic currents were recorded from cells clamped at −60 mV using the whole cell suction-pipette technique.

FIG. 11 shows the selectivity and single channel properties of hASIC3.

a) voltage dependence of the transient and sustained whole cell current. The transient current reverses at 37.6 mV, the sustained current reverses at 10.1 mV.

b) the voltage dependence of the unitary currents of spontaneously active channels at pH7.3 or of channels activated by a step to pH4. Slope conductance between −10 and +40 mV for both conditions is 15.0±0.6 pS. $V_{rev}$=30.2 mV. The $Na^+$ equilibrium potential is at 40.1 mV. Examples of spontaneous channel activity at a resting pH of 7.3 (c) or activity evoked by a drop to pH4 (d). The channel activity recorded at pH7.3 was inhibited by 100 μM amiloride (c). Single channel currents were recorded at −60 mV from outside-out membrane patches excised from hASIC transfected COS cells.

Figure 12:
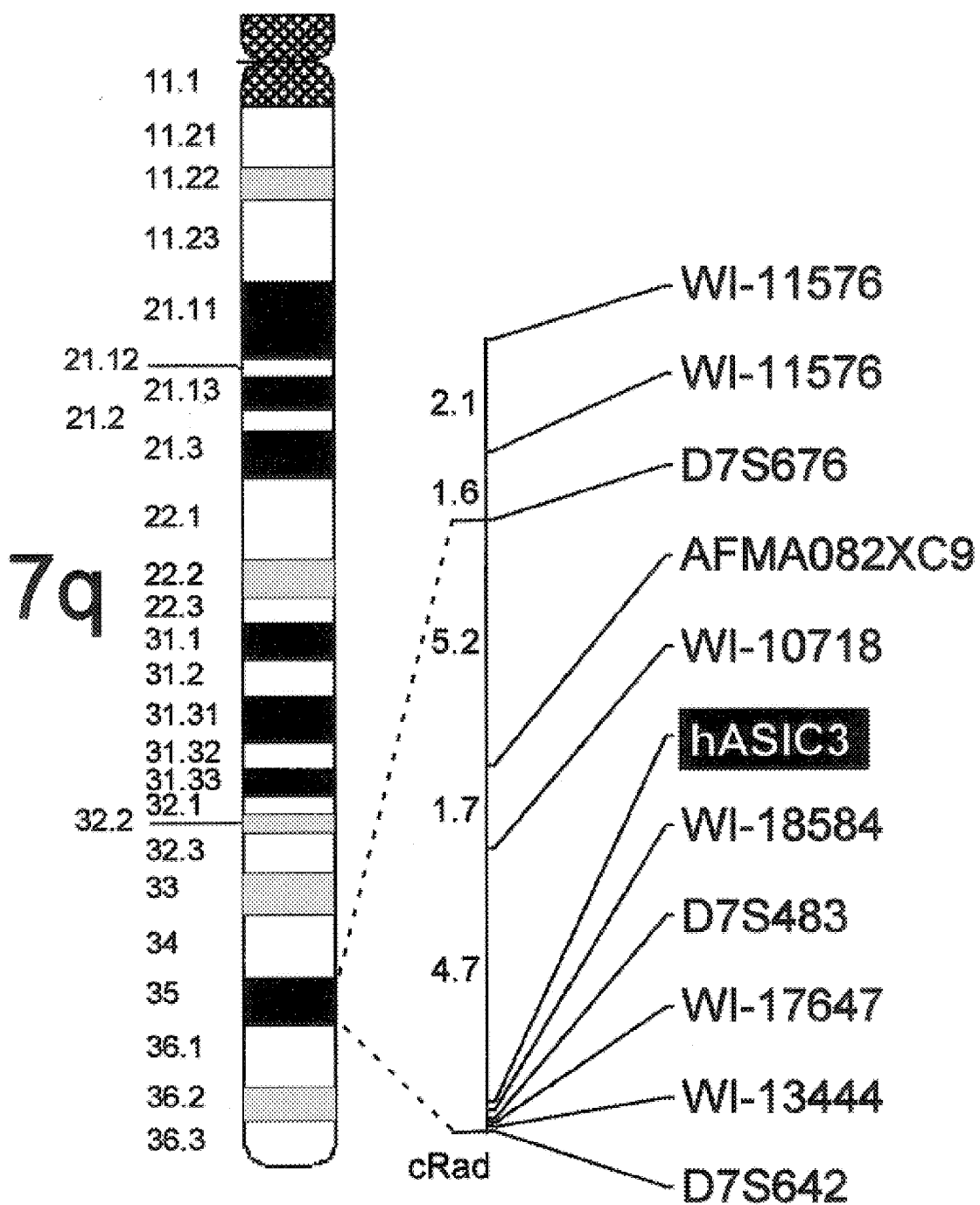
FIG. 12 shows the human chromosomal localization of the hASIC3 gene.

FIG. 12 shows the human chromosomal localization of the hASIC3 gene. The human ASIC3 gene is localized 6.4 cRad telomeric to the framework marker AFMA082XC9 on chromosome 7 (lod score>21). The position of hASIC3 relative to several microsatellites is shown in the right part of the Figure. The relative positions of the markers and their distances (in cRad) are the output of the RHMAPPER program. The microsatellites D7S676 and D7S642 are localized on band q35 of chromosome 7 (data from http://www.ncbi.nlm.nih.gov). The cytogenic localization of those two markers is indicated with dashed lines.

Cloning the ASIC Channel

The conserved sequences of the family of ASIC ionic channels were used to prepare the following PCR primer sequences:

TTYCCIGCIRTIACIITNTGYAAY, and

CAIARICCIAIITGNCCNCCDAWRTC.

A bank of rat brain cDNA (Stratagene #936515) was hybridized with the PCR product of 1 kB of rat brain and the partial clones were isolated. The fifth extremity of the cDNA (202 bp) was isolated by PCR after ligation adapted to the double-strand cDNA.

Electrophysiology 0.25 ng of cRNA was injected into the *Xenopus laevis* oocytes and the recording microelectrodes for the imposed voltage and for the patch-clamp were installed two days after the injection. The bath solutions for the outside-out patch recordings and the pipettes for the outside-out patch and total cells recordings contained: 140 mM KCl (or NMDG), 2 mM $MgCl_2$, 5 mM EGTA, 10 mM Hepes, pH 7.4 (with KOH). The pipettes for the outside-out patch recordings and the bath solutions for the outside-out patch and total cells recordings contained: 140 mM NaCl (or LiCl or NMDGCl), 2 mM $MgCl_2$, 1.8 mM $CaCl_2$, 10 mM Hepes, pH 7.4 (adjusted with HCl, NaOH, LiOH or TMAOH). The rapid pH changes from the initial pH were obtained by perfusion with a bath solution adjusted to the pH indicated in the Figures. The intracellular acidification of the oocytes was implemented by injecting 50 ml of the internal solution at pH 2 or by perfusion and withdrawal of a bath medium containing 20 mM $NH_4Cl$. None of the recorded currents was contaminated by the $Ca^{2+}$ current sensitive to the $Cl^-$ of the Xenopus oocyte. The data were sampled at 2 kHz and filtered at 500 Hz for the analysis (Logiciel Biopatch).

Northern Blot Analysis, RT-PCR and in-situ Hybridization

The Northern blot kit was obtained from Clontech Co. (Palo Alto, Calif.) and contained circa 2 μg of poly(A+) RNA per line. The blot was hybridized with a fragment of the partial human clone (corresponding to bases 270 to 764 of the rat clone) marked with $^{32}P$ at $65_i$ C. in 6×SSC. For the RT-PCR analysis, 5 μg of rat brain total RNA and 3 μg of dorsal root ganglion were reverse transcribed and ⅓₀ of the sample was amplified by 30 PCR cycles with the following sequence primers:

ATTGCTCTTCCCATCTCTAT, and

TTCAAGGCCCATACCTAAGT.

The negative controls were treated in an identical manner with the exception of the reverse transcriptase which was not added. The antisense oligonucleotides corresponding to base 70 to 114 (A), 215 to 248 (B), 1821 to 1859 (C), 1896 to 1940 (D) and the double-strand DNA corresponding to base 1685 to 2672 were used for the in-situ hybridizations. The sections of adult rat brain were hybridized with oligonucleotides B or C the ends of which were marked with $^{32}$P for one night at $37_i$ C. in 50% formamide, 2×SSC, then washed at ambient temperature in 1×SSC. The signal was eliminated by 500-times excess of unmarked oligonucleotides. The dorsal root ganglion sections were hybridized with oligonucleotides A, C or D marked with digoxigenin (DIG)-dUTP and with probe E marked with DIG-dUTP by PCR. The marking of the probes, the preparation of the samples, the hybridization and the visualization of the DIG nucleic acids with alkaline phosphatase conjugated with anti-DIG antibodies were performed in accordance with the supplier's protocols (Boehringer Mannheim).

Computer Analysis

The sequence alignments and the phylogenetic tree (Kimura substitution, UPGMA option) were performed with the GCG program (Genetics Computer Group, Madison, Wis.).

Identification of hASIC3

Comparison of the rat DRASIC protein sequence with the database of expressed sequence tags (EST) identified two partial cDNA sequences from human total fetus (Genbank accession AA449579 and AA449322). Both sequences originate from the same clone (IMAGE ID 785700) that we obtained from the UK HGMP RESOURCE CENTRE. Sequencing both strands using an Applied Biosystems automatic sequencer showed that the clone contains the entire coding sequence.

Chromosomal Lacalization

The human ASIC3 gene was mapped by PCR on the Genebridge 4 Radiation Hybrid DNA panel with the primers CGATTGCAGTTCAGCATCTCT (sense)

and

ACCATTCGGCAGCCGCACTT (antisense)

at an anealing temperature of 65° C. The PCR products were analyzed on 2% agarose gels. Samples were considered positive when a strong amplification of a 159 bp fragment was detected (Code 1), ambiguous when a faint amplification of this fragment was detected (Code 2) and negative when no amplification around 160 bp was visible (Code 0). The positive control (human genomic DNA) was positive and the negative control (hamster genomic DNA) was negative. The following code sequence for the 83 radiation hybrids was obtained and entered into the RHMAPPER program on the Whitehead Institute (http://www-genome.wi.mit.edu) with a Lod score cutoff of 21: 00000 00100 00001 00021 00100 12010 00000 12112 21000 00001 10120 00010 00102 11010 00010 00212 11011 00001 100.

Expression in COS Cells

The vector containing the hASIC3 coding sequence was linearized with NotI and blunt ended with T4 DNA polymerase. After inactivation of the T4 DNA polymerase, the hASIC3 coding sequence was excised with EcoRI and subsequently subcloned into the EcoRI/SalI (blunt) digested PCI expression vector (Promega). COS cells, at a density of 20.000 cells per 35 mm diameter petri dish, were transfected with a mix of CD8 and hASIC3-PCI (1:5) using the DEAE-Dextran method. Cells were used for electrophysiological measurements one to three days after transfection. Successfully transfected cells were recognised by their ability to fix CD8-antibody-coated beads [13].

Electrophysiology

Ion currents were recorded using either the whole cell or outside-out patch-clamp technique. The pipette solution contained (in mM): KCl 120, NaCl 30, $MgCl_2$ 2, EGTA 5, HEPES 10 (pH 7.2). The bath solution contained in mM: NaCl 140, KCl 5, $MgCl_2$ 2, $CaCl_2$ 2, HEPES 10 (pH 7.3). Changes in extracellular pH were induced by opening one out of six outlets of a microperfusion system in front of the cell or patch. Test solutions having a pH of less then 6 were buffered with 10 mM MES rather than HEPES but were identical to the control solution in all other respects. Experiments were carried out at room temperature (20–24° C.).

Results

The 35 kb cDNA isolated from rat brain codes for a protein of 526 amino acids that exhibits, as shown in FIG. 2, homologies with all of the cloned members of the family of amiloride-sensitive degenerine sodium channels.

As shown in FIG. 5, expression of the cRNA in the Xenopus oocytes induced an inflowing current activated by $H^+$ protons. The biophysical and pharmacological properties of the rASIC1A channel are close to those described for the proton-activated cationic channels of sensory neurons [3, 15, 16]. Reduction of the extracellular pH below a pH of 6.9 activates a rapidly rising and desensitized inflowing current (FIG. 5a and b). This channel is activated by extracellular protons since, as shown in FIG. 5(c and d), application of an acid on the extracellular surface of the outside-out patch activates the channel. Intracellular acidification of oocytes and acidification of the intracellular surface of the outside-out patch does not activate the rASIC1A channel nor alter the rASIC1A current induced by the extracellular protons.

The analysis of curves I-V of FIG. 5(c and e) recorded with different extracellular cations shows that $Na^+$ is the majority permeable ion (simple conductance channel 14.3 pS). Like the proton-sensitive ionic channel of the sensory neurons [15, 16], the ASIC channel discriminates weakly between the cations (FIG. 5c, e, f). In fact, the channel is also permeable to $Li^+$, $K^+$, $Ca^{2+}$ and $H^+$ with the ratios $pNa^+/pLi^+$=1.3 (FIG. 5c, e), $pNa^+/pK^+$=13 (FIG. 5c, e), $pNa^+/CA^{2+}$=2.5 (FIG. 5e) and $pNa^+/H^+$=0.8 (FIG. 5f). The permeability to $Ca^{2+}$ of ASIC could be a voltage-independent entry path of $Ca^{2+}$ into the cell. An inflowing current of $Ca^{2+}$ into the cell via the ASIC channels can be detected in the absence of extracellular $Na^+$ (FIG. 6a, b). As indicated in FIG. 5(e), the unitary conductance for $Ca^{2+}$ was 5.2 pS. In the presence of 140 mM of extracellular $Na^+$, augmentation of the concentrations of external $Ca^{2+}$ diminished the amplitude of the current activated by the protons (FIG. 6c), thereby demonstrating that $Ca^{2+}$ inhibits the permeability to $Na^+$. Blockage by external $Ca^{2+}$ is characteristic of the $I(H^+)$ of the sensory neurons [17]. The inflowing current activated by $H^+$ in the sensory neurons is inhibited by amiloride [18] and ethylisopropylamiloride (EIPA) [19]. As shown in FIG. 6(d, e), the rASIC1A channel exhibits the same pharmacology and is blocked in a reversible manner (Kd=10 μM) by amiloride and its derivatives benzamil and EIPA.

In addition, the rASIC1A channel protein exhibits approximately 67% sequence homology with the degenerine ionic channel referred to as MDEG [14] or BNaCl [20], herein designated rASIC2. However, the electrophysiological properties of these two clones expressed in Xenopus oocytes are clearly different:

As shown in FIG. 5(a), the rASIC2 channel is not activated by the same pH changes as the rASIC1A channel.

Substitution of the glycine residue in position 430 of rASIC2 by an acid-inhibiting amino acid such as valine or phenylalanine activates the channel [14], just as the mutation of alanine in position 704 of degenerine MEC-4 causes neurodegeneration in C. elegans [12].

Identical mutations of rASIC1A (glycine in position 431 replaced by valine or phenylalanine) do not lead to activity and the mutants cannot be activated by protons.

Figure 7A:
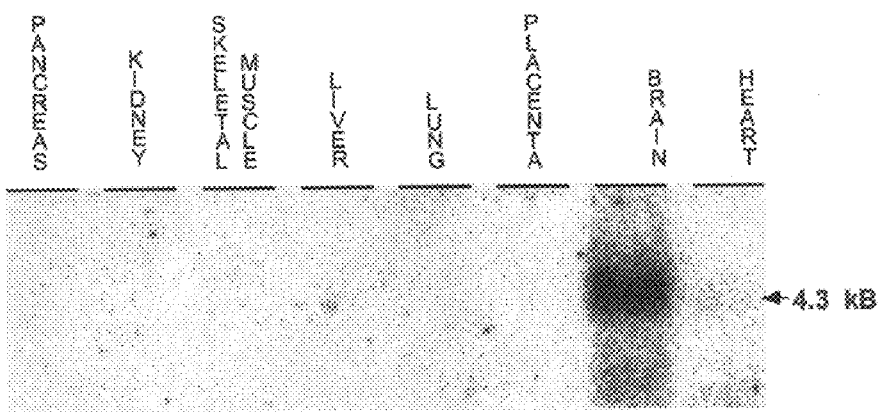
FIG. 7 shows the tissue distribution of ASIC1A channel mRNA.
Figure 7B:
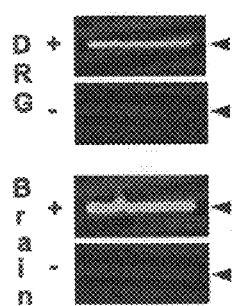
Figure 8C:
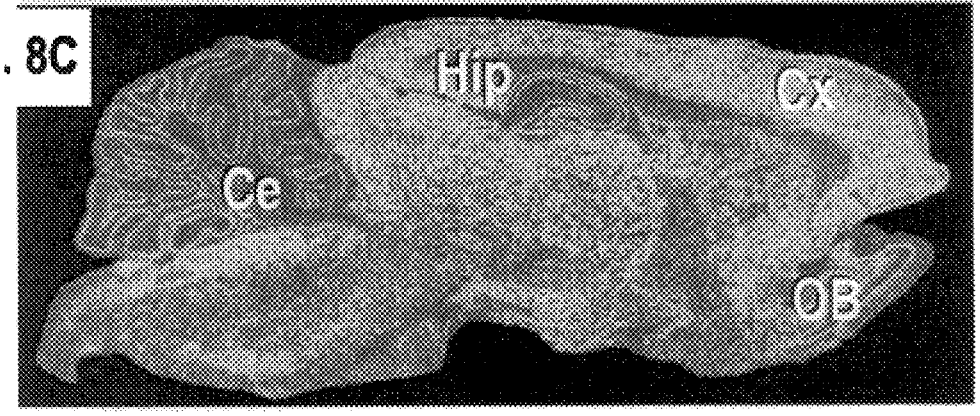

Proton-activated cationic channels have been described not only in the sensory neurons but also in the neurons of the central nervous system [21]. The tissue distribution of the expression of the mRNA of the hASIC1A channel is in agreement with this observation. As shown in FIG. 7a, a 4.3-kb transcript was detected in the brain by Northern blot analysis and the PT-PCR results presented in FIG. 7b show that the dorsal root ganglion expresses the rASIC1A mRNA. FIG. 8(a, b) shows that rASIC1A mRNA is well expressed by the small neurons of the dorsal root ganglion, which supports the fact that ASIC is the rapidly desensitizing proton-activated cationic channel described in the nociceptive sensory neurons. Whereas the presence of proton-activated cationic channels in the dorsal root ganglion is in agreement with their function of acidity detector in nociception, their role in the brain remains to be established. The results of in-situ hybridization in FIG. 8c show a broad and heterogeneous expression of the rASIC1A channel mRNA. The highest levels of expression were observed in the principal olfactory bulb, the cerebral cortex, the hippocampus, the habenula, the basolateral amygdaloid nucleus and the cerebellum. The synaptic activity accompanies extracellular pH changes [22, 23] and the rapid localized pH changes in or close to the synaptic cleft are noticeably more saturated and stronger than the reported macroscopic fluctuations in the pH.

The proton-activated cationic channels are the only known ionic channels that are directly activated by a change in pH and it was envisaged that the extracellular fluctuations in pH played a neuromodulator role [23]. The expression of cationic channels in the brain supports in addition the hypothesis that the pH fluctuations are not solely a neuronal activation by a product, but even more a communications pathway in the central nervous system.

In addition to the rapidly inactivated proton-activated cationic channels, the presence has been reported in the sensory neurons of proton-activated cationic channels exhibiting slower kinetics [4, 24]. The proton-activated cationic channels probably form, like other cationic channels activated by a ligand [25, 26], a family of cationic channels in which different subunits or combinations of subunits constitute channels with diverse pharmacological and biophysical properties.

The sensation of acidity is not uniquely implicated in nociception but is also associated with the transduction of taste [2]. Acid stimulations activate the proton-activated cationic channels in the taste cells [2, 27] and amiloride inhibits the perception of acid taste [2]. Also, the physiological as well as pharmacological data indicate that rASIC1A and other members of this family are implicated in the transduction of taste. It is, in fact, especially surprising that the same class of ionic channels is associated with different facets of sensory perception:

the amiloride-sensitive sodium channels are associated with the transduction of salty taste [2].

the degenerines of *C. elegans* are implicated in mechanotransduction and have been proposed as forming the mechanosensitive ionic channels [28, 29].

the ASIC family of channels are implicated in nociception and the transduction of acid taste.

Comparison of the rASIC3 sequence with the database of expressed sequence tags identified a novel human member of this ion channel family. This novel clone from a total human embryo library codes for a protein of 533 amino acids that shares the closest homology (84% identity, 87% homology) with rASIC3 (FIG. 9). The cloning of a nearly identical cDNA from human testis (hTNaC1), although without functional expression, was reported recently [14].

Expression of the novel hASIC3 clone in COS cells induced a $H^+$-gated cation current with kinetics very similar to that of rASIC3. When the pH is decreased rapidly from pH 7.3 to pH 5, a biphasic current is observed. A rapidly inactivating component is followed by a sustained current (FIG. 10A). These very peculiar kinetics that are also found with the rASIC3 [9] channel together with the sequence homology (84% amino acid, 82% nucleic acid identity) with rASIC3 suggest that this novel clone is the human ASIC3. We therefore call it hASIC3 (human Acid Sensing Ion Channel 3).

The pH dependence of the transient hASIC3 current ($pH_{0.5}$=6.2, FIG. 10A) is almost identical to that reported for rASIC3 ($pH_{0.5}$=6.5) [9]. However, the pH dependencies of the sustained rASIC3 and hASIC3 currents are clearly different. While rASIC3 requires very acidic pH values (<pH 4.5) [9] for activation of the sustained current, the sustained hASIC3 current starts to activate when the extracellular pH decreases to below pH 6 and reaches half-maximal activity at pH 4.3 (FIG. 10A). The channel activity of hASIC3 depends, just as that of the rASIC3 channel, on the resting pH (FIG. 10B). The maximal activity of the transient hASIC3 current was observed when the resting pH was above pH 8, indicating that a fraction of the transiently activating $H^+$-gated cation channels are inactivated at physiological pH. Half-maximal activation of the transient current was observed at pH 7.5, a slightly more alkaline pH than that reported for the rASIC3 clone (pH 6.5) [9]. When the resting pH was below pH 7, only activation of the sustained current could be observed after acidification of the bath medium (FIG. 10B). The sustained hASIC3 current can, just as the sustained rASIC3 channel, still be activated when the initial pH is quite acidic (pH5) (FIG. 10B).

All members of the ASIC family cloned so far are sensitive to the diuretic amiloride. The hASIC3 channel is no exception. The effect of amiloride on the hASIC3 current is similar to that reported for rASIC3 [9]. The transient current is inhibited by amiloride ($K_D$=15.9 $\mu$M; FIG. 2C) as well as by triamterene (FIG. 10C), while the sustained hASIC3 current is virtually not affected by those diuretics.

The transient hASIC3 current reverses at 37.6 mV, close to the $Na^+$ reversal potential, indicating a high selectivity for $Na^+$ vs $K^+$ (FIG. 11A). Conversely, the sustained current discriminates much less between $Na^+$ and $K^+$ (selectivity ratio $gNa^+/gK^+$=1.62) as it reverses at 10.1 mV (FIG. 11A). The low selectivity for $Na^+$ vs $K^+$ of the sustained hASIC3 current clearly distinguishes the hASIC3 channel from the rASIC3 channel which is highly selective for $Na^+$ [9].

Proton-induced unitary currents were recorded from excised outside-out patches (FIG. 11B–D). In a narrow pH window around pH 7.3, spontaneous channel activity can be observed (FIG. 11C) that disappears upon an increase in pH to 8.0, a decrease in pH to 6.0 (not shown) or in the presence of 100 $\mu$M amiloride (FIG. 11C). This basal current is mainly carried by $Na^+$, since it reverses at 30.2 mV (FIG. 11B). When the pH on the extracellular face of an outside-out patch is decreased from pH 7.3 to pH 4, unitary currents are induced (FIG. 11D) that reverse at the same membrane potential as the spontaneously active channel (FIG. 11B). The unitary conductance of the hASIC3 channel for $Na^+$ is 15±0.6 pS, close to that reported for rat ASIC3 (12.6 pS) [9]. While the sustained non-selective $H^+$-activated hASIC3 current could be easily detected in whole cell recordings, no sustained or non-selective current could be recorded on outside-out patches. One possible explanation is, that soluble factors might be necessary that are lost during excision of the patch.

The human chromosomal localization of the hASIC3 gene was determined by PCR on a human-hamster radiation hybrid DNA panel. The hASIC3 gene is localised on the human chromosome 7q35, 6.4 cRad telomeric from the microsatellite AFMA082XC9 (Lod score>21). To our knowledge, no hereditary diseases with symptoms that are consistent with an altered function of a $H^+$-gated cation channel were mapped to this region of the human genome.

The hASIC3 channel subunit forms a sustained $H^+$-gated cation channel that has properties similar to those reported for the rASIC3 channel. However, very important differences exist. Most importantly, the sustained hASIC3 current requires less acidic pH for activation than rASIC3 [9]. In this respect the properties of the hASIC3 channel match better the physiological and electrophysiological data from sensory neurones than those of rASIC3. Subcutaneous perfusion of human volunteers with acidic buffer causes pain. At pH 5.2, the pain was rated 20% on a scale ranging from 0 to 100% (unbearable pain) [2]. Furthermore, a subpopulation of polymodal C-fibres in rat nerve-skin preparations can be excited by acidic pH [4]. The threshold for activation lies between pH 6.9 and pH 6.1, maximal stimulation is reached at pH 5.2. The endogenous $H^+$-gated cation channel recorded in rat sensory neurones starts to activate below pH 6.6 [5]. The pH dependence of the sustained hASIC3 current matches closely those physiological data, while rASIC3 has a pH dependence that is shifted two pH units towards more acidic pH values [9]. One possible explanation for the differences between physiological data and the pH dependence of the sustained ASIC3 channel (especially the rASIC3) might be the participation of as yet unknown subunits n the formation of the native channel. Heteromultimeric assembly was previously demonstrated for the rASIC3 channel [9]. rASIC3 can associate with rASIC2b resulting in an altered selectivity of the channel. While rASIC3 is completely $Na^+$-selective, the sustained current of the heteromultimeric rASIC3/rASIC2b channel does not discriminate between $Na^+$ and $K^+$. The $H^+$-gated cation channel recorded in rat sensory neurones does not discriminate between $Na^+$ and $K^+$ either [5], suggesting that both rASIC3 and rASIC2b participate in the formation of this ion channel in rat sensory neurons. In contrast with the rASIC3 channel, hASIC3 does not require coexpression of other subunits to generate a non-selective sustained current. The ion selectivity of sustained human $H^+$-gated cation channels is not known yet. A more detailed electrophysiological characterization of human sustained $H^+$-gated cation channels will be necessary to allow a comparison of the properties of the native channel with those of the hASIC3 channel.

LIST OF SEQUENCES

Information Concerning SEQ ID NO: 1 i) CHARACTERISTIC OF THE SEQUENCE:
   A) LENGTH: 3562 base pairs
   B) TYPE: nucleic acid
   C) NUMBER OF STRANDS: double
   D) CONFIGURATION: linear
ii) TYPE OF MOLECULE: DNA
vi) ORIGIN: rat
ix) CHARACTERISTIC
   A) NAME/KEY: ASIC
   B) LOCALIZATION: 123 . . . 1700
xi) DESCRIPTION OF THE SEQUENCE: SEQ ID NO: 1:
Top of page 28=

Information Concerning SEQ ID NO: 2 i) CHARACTERISTIC OF THE SEQUENCE:
   A) LENGTH: 1620 base pairs
   B) TYPE: nucleic acid
   C) NUMBER OF STRANDS: double
   D) CONFIGURATION: linear
ii) TYPE OF MOLECULE: DNA
vi) ORIGIN: human
ix) CHARACTERISTIC
   A) NAME/KEY: ASIC
   B) LOCALIZATION: 1 . . . 1542
xi) DESCRIPTION OF THE SEQUENCE: SEQ ID NO: 2:
Top of page 31=

Information Concerning SEQ ID NO: 3 i) CHARACTERISTIC OF THE SEQUENCE:
   A) LENGTH: 1666 base pairs
   B) TYPE: nucleic acid
   C) NUMBER OF STRANDS: double
   D) CONFIGURATION: linear
ii) TYPE OF MOLECULE: DNA
vi) ORIGIN: human
ix) CHARACTERISTIC
   A) NAME/KEY: MDEG
   B) LOCALIZATION: 127 . . . 1663
xi) DESCRIPTION OF THE SEQUENCE: SEQ ID NO: 3:
Top of page 34=

Information Concerning SEQ ID NO: 4 i) CHARACTERISTIC OF THE SEQUENCE:
   A) LENGTH: 3647 base pairs
   B) TYPE: nucleic acid
   C) NUMBER OF STRANDS: double
   D) CONFIGURATION: linear
ii) TYPE OF MOLECULE: DNA
vi) ORIGIN: rat
ix) CHARACTERISTIC
   A) NAME/KEY: ASIC1B
   B) LOCALIZATION: 109 . . . 1785
xi) DESCRIPTION OF THE SEQUENCE: SEQ ID NO: 4:
Top of page 38=

Information Concerning SEQ ID NO: 5 i) CHARACTERISTIC OF THE SEQUENCE:
   A) LENGTH: 1602 base pairs
   B) TYPE: nucleic acid
   C) NUMBER OF STRANDS: double
   D) CONFIGURATION: linear
ii) TYPE OF MOLECULE: DNA
vi) ORIGIN: rat
ix) CHARACTERISTIC
   A) NAME/KEY: ASIC3
   B) LOCALIZATION: 1 . . . 1602
xi) DESCRIPTION OF THE SEQUENCE: SEQ ID NO: 5:
Top of page41=

Information Concerning SEQ ID NO: 6 i) CHARACTERISTIC OF THE SEQUENCE:
   A) LENGTH: 1948 base pairs

B) TYPE: nucleic acid
C) NUMBER OF STRANDS: double
D) CONFIGURATION: linear
ii) TYPE OF MOLECULE: DNA
vi) ORIGIN: rat
ix) CHARACTERISTIC
A) NAME/KEY: ASIC2B
B) LOCALIZATION: 16 . . . 1707
xi) DESCRIPTION OF THE SEQUENCE: SEQ ID NO: 6:

Information Concerning SEQ ID NO: 7 i) CHARACTERISTIC OF THE SEQUENCE:
A) LENGTH: 1736 base pairs
B) TYPE: nucleic acid
C) NUMBER OF STRANDS: double
D) CONFIGURATION: linear
ii) TYPE OF MOLECULE: DNA
vi) ORIGIN: human
ix) CHARACTERISTIC
A) NAME/KEY: ASIC3
B) LOCALIZATION: 18 . . . 1611
xi) DESCRIPTION OF THE SEQUENCE: SEQ ID NO: 7:

Information Concerning SEQ ID NO: 8 i) CHARACTERISTIC OF THE SEQUENCE:
A) LENGTH: 531
B) TYPE: protein
C) NUMBER OF STRANDS: single
D) CONFIGURATION: linear
ii) TYPE OF MOLECULE: protein
vi) ORIGIN: human
ix) CHARACTERISTIC
A) NAME/KEY: hASIC3
B) LOCALIZATION: 1–531

REFERENCES

1. Rang, H. P., Bevan, S. & Dray, A. *Br. Med. Bull.* 47, 534–548 (1991).
2. Lindeman, B. *Physiol Rev.* 76, 718–766 (1996).
3. Krishtal, O. A. & Pidoplichko, V. I. *Neuroscience* 6, 2599–2601 (1981).
4. Bevan, S. & Geppeti, P. *Trends Neurosci.* 17, 509–512 (1994).
5. Akaike, N., Krishtal, O. A. & Maruyama, T. *J. Neurophysiol.* 63, 805–813 (1990).
6. Canessa, C. M., Horisberger, J. D. & Rossier, B. C. *Nature* 361, 467–470 (1993).
7. Canessa, C. M., Schild, L., Buell, G., Thorens, B., Gautschi, I., Horisberger, J. D. & Rossier, B. C. *Nature* 367, 463–467 (1994).
8. Lingueglia, E., Voilley, N., Waldmann, H., Lazunski, M. & Barbry, P. *Febs Lett.* 318, 95–99 (1993).
9. Lingueglia, E., Renard, S., Waldmann, R., Voilley, N., Champigny, G., Plass, H., Lazunski, M. & Barbry, P., *J. Biol. Chem.* 269, 13736–13739 (1994).
10. Lingueglia, E., Champigny, G., Lazdunski, M. & Barbry, P. *Nature* 378, 730–733 (1995).
11. Waldmann, R., Champigny, G., Bassilana, F., Voilley, N. & Lazdunski, M. *J. Biol. Chem.* 270, 27411–27414 (1995).
12. Driscoll, M. & Chalfie, M. *Nature* 349, 588–593 (1991).
13. Huang, M. & Chalfie, M. *Nature* 367, 467–470 (1994).
14. Waldmann, R., Champigny, G., Voilley, N., Lauritzen, I. & Lazdunski, M. *J Biol. Chem.* 271, 10433–10434 (1996).
15. Kovalchuk Yu, N., Krishtal, O. A. & Nowycky, M. C. *Neurosci. Lett.* 115-237–242 (1990).
16. Konnerth, A., Lux, H. D. & Morad, M. *J. Physiol.* 386, 603–633 (1987).
17. Davies, N. W., Lux, H. D. & Morad, M. *J. Physiol.* 400, 159–187 (1988).
18. Korkushko, A. O. & Krishtal, O. A. *Neirofiziologiia* 16, 557–561 (1984).
19. Grantyn, R., Perouansky, M., Rodriguez-Tebar, A. & Lux, H. D. *Dev. Brain Res.* 49,150–155 (1989).
20. Price, M. P., Snyder, P. M. & Welsh, M. J. *J. Biol. Chem.* 271, 7879–7882 (1996).
21. Akaike, N. & Ueno, S. *Prog. Neurobiol.* 43, 73–83 (1994).
22. Krishtal, O. A., Osipchuk, Y. V., Shelest, T. N. & Smirnoff, S. V. *Brain Res.* 436, 352–356 (1987).
23. Chesier, M. & Kaila, K. *Trends Neurosci.* 15, 396–402 (1992).
24. Bevan, S. & Yeats, J. *J. Physiol.* 433, 145–161 (1991).
25. Lewis, C., Neidhart, S., Holy, C., North, R. A., Buell, G. & Surprenant, A. *Nature* 377, 432–435 (1995).
26. Barnard, E. A. *Trends Pharmacol. Sci.* 17, 305–309 (1996).
27. Okada, Y., Miyamoto, T. & Sato, T. *J. Exp. Biol.* 187, 19–32 (1994).
28. Liu, J. Schrank, B. & Waterson, R. *Science* 273, 361 (1996).
29. Waldmann, R., Champigny, G. & Lazdunski, M. *J. Biol. Chem.* 270, 11735–11737 (1995).
30. Renard, S., Lingueglia, E., Voilley, N., Lazdunski, M. & Barbry, P. *J. Biol. Chem.* 269, 12981–12986 (1994).
31. Reeh, P. W. and Steen, K. H. *Prog Brain Res* 113, 143–151 (1996).
32. Steen, K. H., Steen, A. E., Kreysel, H. W. & Reeh, P. W. *Pain* 66, 163–170 (1996).
33. Steen, K. H., Issberner, U. & Reeh, P. W. *Neurosci Lett* 199, 29–32 (1995).
34. Steen, K. H., Reeh, P. W., Anton, F. & Handwerker, H. O. *J. Neurosci* 12, 86–95 (1992).
35. Waldmann, R., Champigny, G., Bassilana, F., Heurteaux, C. and Lazdunski, M. *Nature* 386, 173–177 (1997).
36. Bassilana, F., Champigny, G., Waldmann, R., de Weille, J. R., Heurteaux, C. & Lazdunski, M. *J. Biol. Chem.* 272, 28819–28822 (1997).
37. Waldmann, R., Bassilana, F., de Weille, J., Champigny, G., Heurteaux, C. & Lazdunski, M. *J. Biol. Chem.* 272, 20975–20978 (1997)
38. Lingueglia, E., de Weille, J. R., Bassilana, F., Heurteaux, C., Sakai, H., Waldmann, R. & Lazdunski, M. J. Biol Chem. 272, 29778–29783 (1997).
39. Waldmann, R. & Lazdunski, M. *Curr. Op. Neurobiol.* 8, 418–424 (1998).
40. Baumann, T. K., Burchiel, K. J., Ingram, S. L. & Martenson, M. E. *Pain* 65, 31–38 (1996).
41. Jurman, M. E., Boland, L. M., Liu, Y. & Yellen, G. *Biotechniques* 17, 876–881 (1994).
42. Ishibashi, K. & Marumo, F. *Biochem. Biophys Res Comm* 245, 589–593 (1998).

We claim:

1. A method of screening a substance which modulates the activity of cation transport channels comprised of human acid sensing ionic channel hASIC3, comprising contacting pre-selected amounts of the substance to be tested with cells expressing said cation transport channel, measuring the effects of the substance on the transport functions of the cation transport channel, and identifying the substance that has an effect on potassium channel activity.

2. A substance, identified by the method of claim 1 that is capable of influencing the transport functions of a cation transport channel.

* * * * *

SEQUENCE LISTING

<160> NUMBER OF SEQ ID NOS: 22

<210> SEQ ID NO 1
<211> LENGTH: 3562
<212> TYPE: DNA
<213> ORGANISM: rattus sp.
<220> FEATURE:
<221> NAME/KEY: CDS
<222> LOCATION: (123)..(1700)

<400> SEQUENCE: 1

```
cacacacaca cacacacaca cacacacaca cacacacaca cacacagaac ctgcgcctgt      60
gcctgtgcct gtgcctgtgc ctgtttgaga gctggagaca cagaaggatc cccttggcaa     120 gg atg gaa ttg aag acc gag gag gag gag gtg ggt ggt gtc cag ccg        167
   Met Glu Leu Lys Thr Glu Glu Glu Glu Val Gly Gly Val Gln Pro
    1               5                  10                  15 gtg agc atc cag gct ttc gcc agc agc tcc acg ctc cat ggt ctt gcc       215
Val Ser Ile Gln Ala Phe Ala Ser Ser Ser Thr Leu His Gly Leu Ala
                20                  25                  30 cac atc ttc tcc tat gag cgg ctg tct ctg aag cgg gca ctg tgg gcc       263
His Ile Phe Ser Tyr Glu Arg Leu Ser Leu Lys Arg Ala Leu Trp Ala
             35                  40                  45 ctg tgc ttc ctg ggt tcg ctg gcc gtc ctg ctg tgt gtg tgc act gag       311
Leu Cys Phe Leu Gly Ser Leu Ala Val Leu Leu Cys Val Cys Thr Glu
         50                  55                  60 cgt gtg cag tac tac ttc tgc tat cac cac gtc acc aag ctt gac gaa       359
Arg Val Gln Tyr Tyr Phe Cys Tyr His His Val Thr Lys Leu Asp Glu
     65                  70                  75 gtg gct gcc tcc cag ctc acc ttc cct gct gtc aca ctg tgc aat ctc       407
Val Ala Ala Ser Gln Leu Thr Phe Pro Ala Val Thr Leu Cys Asn Leu
 80                  85                  90                  95 aat gag ttc cgc ttt agc caa gtc tcc aag aat gac ctg tac cat gct       455
Asn Glu Phe Arg Phe Ser Gln Val Ser Lys Asn Asp Leu Tyr His Ala
                100                 105                 110 ggg gag ctg ctg gcc ctg ctc aac aac agg tat gag atc ccg gac aca       503
Gly Glu Leu Leu Ala Leu Leu Asn Asn Arg Tyr Glu Ile Pro Asp Thr
            115                 120                 125 cag atg gct gat gaa aag cag cta gag ata ttg cag gac aag gcc aac       551
Gln Met Ala Asp Glu Lys Gln Leu Glu Ile Leu Gln Asp Lys Ala Asn
        130                 135                 140 ttc cgg agc ttc aag ccc aag ccc ttc aac atg cgt gaa ttc tac gac       599
Phe Arg Ser Phe Lys Pro Lys Pro Phe Asn Met Arg Glu Phe Tyr Asp
    145                 150                 155 aga gcg ggg cac gat att cga gac atg ctg ctc tcg tgc cac ttc cgt       647
Arg Ala Gly His Asp Ile Arg Asp Met Leu Leu Ser Cys His Phe Arg
160                 165                 170                 175 ggg gag gcc tgc agc gct gaa gat ttc aaa gtg gtc ttc act cgg tat       695
Gly Glu Ala Cys Ser Ala Glu Asp Phe Lys Val Val Phe Thr Arg Tyr
                180                 185                 190 ggg aag tgt tac aca ttc aac tcg ggc caa gat ggg cgg cca cgg ctg       743
Gly Lys Cys Tyr Thr Phe Asn Ser Gly Gln Asp Gly Arg Pro Arg Leu
            195                 200                 205 aag acc atg aaa ggt ggg act ggc aat ggc ctg gag atc atg ctg gac       791
Lys Thr Met Lys Gly Gly Thr Gly Asn Gly Leu Glu Ile Met Leu Asp
        210                 215                 220 att cag caa gat gaa tat ttg cct gtg tgg gga gag acc gac gag aca       839
Ile Gln Gln Asp Glu Tyr Leu Pro Val Trp Gly Glu Thr Asp Glu Thr
    225                 230                 235
```

-continued

| | | |
|---|---|---|
| tcc ttc gaa gca ggc atc aaa gtg cag atc cac agt cag gat gaa ccc<br>Ser Phe Glu Ala Gly Ile Lys Val Gln Ile His Ser Gln Asp Glu Pro<br>240                           245                       250                       255 | | 887 |
| cct ttc atc gac cag ctg ggc ttt ggt gtg gct cca ggt ttc cag acg<br>Pro Phe Ile Asp Gln Leu Gly Phe Gly Val Ala Pro Gly Phe Gln Thr<br>                       260                     265                   270 | | 935 |
| ttt gtg tct tgc cag gag cag agg ctc atc tac ctg ccc tca ccc tgg<br>Phe Val Ser Cys Gln Glu Gln Arg Leu Ile Tyr Leu Pro Ser Pro Trp<br>         275                     280                     285 | | 983 |
| ggc acc tgc aat gct gtt acc atg gac tcg gat ttc ttc gac tcc tac<br>Gly Thr Cys Asn Ala Val Thr Met Asp Ser Asp Phe Phe Asp Ser Tyr<br>         290                     295                   300 | | 1031 |
| agc atc act gcc tgc cgg att gat tgc gag acg cgt tac ctg gtg gag<br>Ser Ile Thr Ala Cys Arg Ile Asp Cys Glu Thr Arg Tyr Leu Val Glu<br>305                           310                       315 | | 1079 |
| aac tgc aac tgc cgt atg gtg cac atg cca ggg gac gcc cca tac tgc<br>Asn Cys Asn Cys Arg Met Val His Met Pro Gly Asp Ala Pro Tyr Cys<br>320                           325                     330                   335 | | 1127 |
| act cca gag cag tac aag gag tgt gca gat cct gcc ctg gac ttc cta<br>Thr Pro Glu Gln Tyr Lys Glu Cys Ala Asp Pro Ala Leu Asp Phe Leu<br>                       340                     345                   350 | | 1175 |
| gtg gag aaa gac cag gaa tac tgc gtg tgt gag atg cct tgc aac ctg<br>Val Glu Lys Asp Gln Glu Tyr Cys Val Cys Glu Met Pro Cys Asn Leu<br>                   355                     360                   365 | | 1223 |
| acc cgc tac ggc aag gag ctg tcc atg gtc aag atc cca agc aaa gcc<br>Thr Arg Tyr Gly Lys Glu Leu Ser Met Val Lys Ile Pro Ser Lys Ala<br>                       370                     375                   380 | | 1271 |
| tcc gcc aag tac ctg gcc aag aag ttc aac aaa tcg gag cag tac ata<br>Ser Ala Lys Tyr Leu Ala Lys Lys Phe Asn Lys Ser Glu Gln Tyr Ile<br>385                           390                       395 | | 1319 |
| ggg gag aac att ctg gtg ctg gac att ttc ttt gaa gtc ctc aac tat<br>Gly Glu Asn Ile Leu Val Leu Asp Ile Phe Phe Glu Val Leu Asn Tyr<br>400                           405                     410                   415 | | 1367 |
| gag acc atc gag cag aaa aag gcc tat gag atc gca ggg ctg ttg ggt<br>Glu Thr Ile Glu Gln Lys Lys Ala Tyr Glu Ile Ala Gly Leu Leu Gly<br>                       420                     425                   430 | | 1415 |
| gac atc ggg ggc cag atg ggg ttg ttc atc ggt gcc agc atc ctc acc<br>Asp Ile Gly Gly Gln Met Gly Leu Phe Ile Gly Ala Ser Ile Leu Thr<br>                       435                     440                   445 | | 1463 |
| gtg ctg gaa ctc ttt gac tat gcc tac gag gtc att aag cac agg ctg<br>Val Leu Glu Leu Phe Asp Tyr Ala Tyr Glu Val Ile Lys His Arg Leu<br>         450                     455                     460 | | 1511 |
| tgc aga cgt gga aag tgc cag aag gag gct aag agg agc agc gca gac<br>Cys Arg Arg Gly Lys Cys Gln Lys Glu Ala Lys Arg Ser Ser Ala Asp<br>465                           470                     475 | | 1559 |
| aag ggc gtg gcg ctc agc ctg gat gac gtc aaa aga cac aat ccc tgc<br>Lys Gly Val Ala Leu Ser Leu Asp Asp Val Lys Arg His Asn Pro Cys<br>480                           485                     490                   495 | | 1607 |
| gag agc ctc cga gga cat cct gcc ggg atg acg tac gct gcc aac atc<br>Glu Ser Leu Arg Gly His Pro Ala Gly Met Thr Tyr Ala Ala Asn Ile<br>                       500                     505                   510 | | 1655 |
| cta cct cac cat ccc gct cga ggc acg ttt gag gac ttt acc tgc<br>Leu Pro His His Pro Ala Arg Gly Thr Phe Glu Asp Phe Thr Cys<br>                   515                     520                   525 | | 1700 |
| taagccctcg caggccgctg taccaaaggc ctaggtgggg agggctgggg gagcaagggg | | 1760 |
| cccccaactg cccccagcta ccctgtggac ttaactgcat tcctggtcag tggttccctc | | 1820 |
| ttgtctgtgg tgagaaagga gtcttgacca tagagtcctc tcccagcctc tatcccatct | | 1880 |
| ttttatttta atttaatcac atttgctctg taatattgct tgaggctggg gatcgtgatt | | 1940 |

-continued

```
tcccccccagt tctttttattg ttgagaatag ttttctctat tctgggtttt ctgttatttc    2000
aaatgaatct gcaaattgct cttcccatct ctatgaagaa ttgcgttgga attttgatgg    2060
ggattgtatt gaatctgtag attgcctttg gtaagatggc cattttttact atgttaatcc    2120 tgccaattca tgagcaaggg agatctttct atctctgaaa tctacttcag tttctttctt    2180
cagagacttg aagttcttgt cataaaaatc ttttttggtta gagccacacc aaggtatttt    2240
atattgtttg tgactattgt gaatggtgtc atttccctaa tttccttctc agcctactta    2300
tcctttgagt agaggaaggc ttctgatttg tttggggttaa ttttataccc agctgctttg    2360
ctaaagttct ttatcaggtt taggtgttct ctggtggaac ttttggggtc acgtaagaat    2420
actattatat catctgcaaa tagtgatatt tcacttcttc ctttccaatt tctatccctc    2480
tggggacttt tgttgtctca attgctctgg ctaggacttc aaattctata ttgaatagat    2540
agggagagag tgggcagcct tgtctagttc ctggttttcg tgggatcgct tcaaatttct    2600
ctccatttag tttgatattg gctactggtt tgctgtatat ggcttttact gtacttaggt    2660
atgggccttg aattcctgat atttccaaga cttttaacat gaagggtttt tgaaatttgc    2720
caaatgcttt ctcagcatct aatgagatga tcatgtgccc tccccccacc ttgagtttgt    2780
ttatatagtg ggtacatga aaggatcatt tctaatagtc cacaagtctg ccaaatcttg    2840
ctgattgtga ctcatttcca tagcaggctc tataacttct ctaacagatt gcattaaact    2900
ctgcttgggg aaggcattac ctcttggttg aagcaatgtt gtagtttcta tgcctgctga    2960
gtaaatagcc tcaagtccaa gtacttgccc agactaatga tcaaacgtat ccaggagttc    3020
cataccagag atgtactctt ctctcctttg aagtacattg ctggaagagt aattgtgttt    3080
gctagagata ctccttcgaa ctgcaaaaga atctcttgg ctaagcatat aatcaagcct    3140
caggttttct ttttattaaa tagctgcttg taagaaagtg gacactaagc atataccctca    3200 aagggagaca gaatgactct gtgccttcac tgatggaagt ctgggttaca aattacatca    3260
gaagaaccta tcatagtgaa acatctcatt ccctggtat aatcccttct agaaatacac    3320
ttgtgactct gaaatgttat aatcgtgaca actaggctgt tacagataca ccaagttaaa    3380
tttgatagag aaaccaggct tggagcctca tgtccatagg gcaagaggaa gatgctgagt    3440
gtttaaggtt ggtttgagcg aagaacaata ccttgtgtca caaaaatgaa aggaaaaaag    3500
aaaaaaggaa agaaggaaag aaagagagag aaagaaaaag aaagaaagaa aaaaaaaaaa    3560
aa                                                                   3562
```

<210> SEQ ID NO 2
<211> LENGTH: 526
<212> TYPE: PRT
<213> ORGANISM: rattus sp.

<400> SEQUENCE: 2

```
Met Glu Leu Lys Thr Glu Glu Glu Val Gly Gly Val Gln Pro Val
 1               5                  10                  15

Ser Ile Gln Ala Phe Ala Ser Ser Thr Leu His Gly Leu Ala His
            20                  25                  30

Ile Phe Ser Tyr Glu Arg Leu Ser Leu Lys Arg Ala Leu Trp Ala Leu
        35                  40                  45

Cys Phe Leu Gly Ser Leu Ala Val Leu Cys Val Cys Thr Glu Arg
     50                  55                  60

Val Gln Tyr Tyr Phe Cys Tyr His His Val Thr Lys Leu Asp Glu Val
 65                  70                  75                  80
```

-continued

```
Ala Ala Ser Gln Leu Thr Phe Pro Ala Val Thr Leu Cys Asn Leu Asn
                85                  90                  95
Glu Phe Arg Phe Ser Gln Val Ser Lys Asn Asp Leu Tyr His Ala Gly
            100                 105                 110
Glu Leu Leu Ala Leu Leu Asn Asn Arg Tyr Glu Ile Pro Asp Thr Gln
        115                 120                 125
Met Ala Asp Glu Lys Gln Leu Glu Ile Leu Gln Asp Lys Ala Asn Phe
    130                 135                 140
Arg Ser Phe Lys Pro Lys Pro Phe Asn Met Arg Glu Phe Tyr Asp Arg
145                 150                 155                 160
Ala Gly His Asp Ile Arg Asp Met Leu Leu Ser Cys His Phe Arg Gly
                165                 170                 175
Glu Ala Cys Ser Ala Glu Asp Phe Lys Val Val Phe Thr Arg Tyr Gly
            180                 185                 190
Lys Cys Tyr Thr Phe Asn Ser Gly Gln Asp Gly Arg Pro Arg Leu Lys
        195                 200                 205
Thr Met Lys Gly Gly Thr Gly Asn Gly Leu Glu Ile Met Leu Asp Ile
    210                 215                 220
Gln Gln Asp Glu Tyr Leu Pro Val Trp Gly Glu Thr Asp Glu Thr Ser
225                 230                 235                 240
Phe Glu Ala Gly Ile Lys Val Gln Ile His Ser Gln Asp Glu Pro Pro
                245                 250                 255
Phe Ile Asp Gln Leu Gly Phe Gly Val Ala Pro Gly Phe Gln Thr Phe
            260                 265                 270
Val Ser Cys Gln Glu Gln Arg Leu Ile Tyr Leu Pro Ser Pro Trp Gly
        275                 280                 285
Thr Cys Asn Ala Val Thr Met Asp Ser Asp Phe Phe Asp Ser Tyr Ser
    290                 295                 300
Ile Thr Ala Cys Arg Ile Asp Cys Glu Thr Arg Tyr Leu Val Glu Asn
305                 310                 315                 320
Cys Asn Cys Arg Met Val His Met Pro Gly Asp Ala Pro Tyr Cys Thr
                325                 330                 335
Pro Glu Gln Tyr Lys Glu Cys Ala Asp Pro Ala Leu Asp Phe Leu Val
            340                 345                 350
Glu Lys Asp Gln Glu Tyr Cys Val Cys Glu Met Pro Cys Asn Leu Thr
        355                 360                 365
Arg Tyr Gly Lys Glu Leu Ser Met Val Lys Ile Pro Ser Lys Ala Ser
    370                 375                 380
Ala Lys Tyr Leu Ala Lys Lys Phe Asn Lys Ser Glu Gln Tyr Ile Gly
385                 390                 395                 400
Glu Asn Ile Leu Val Leu Asp Ile Phe Phe Glu Val Leu Asn Tyr Glu
                405                 410                 415
Thr Ile Glu Gln Lys Lys Ala Tyr Glu Ile Ala Gly Leu Leu Gly Asp
            420                 425                 430
Ile Gly Gly Gln Met Gly Leu Phe Ile Gly Ala Ser Ile Leu Thr Val
        435                 440                 445
Leu Glu Leu Phe Asp Tyr Ala Tyr Glu Val Ile Lys His Arg Leu Cys
    450                 455                 460
Arg Arg Gly Lys Cys Gln Lys Glu Ala Lys Arg Ser Ser Ala Asp Lys
465                 470                 475                 480
Gly Val Ala Leu Ser Leu Asp Asp Val Lys Arg His Asn Pro Cys Glu
                485                 490                 495
```

```
Ser Leu Arg Gly His Pro Ala Gly Met Thr Tyr Ala Ala Asn Ile Leu
            500                 505                 510
Pro His His Pro Ala Arg Gly Thr Phe Glu Asp Phe Thr Cys
            515                 520                 525

<210> SEQ ID NO 3
<211> LENGTH: 1620
<212> TYPE: DNA
<213> ORGANISM: Homo sapiens
<220> FEATURE:
<221> NAME/KEY: CDS
<222> LOCATION: (1)..(1542)

<400> SEQUENCE: 3 ccg gtg agc atc cag gcc ttc gcc agc agc tcc aca ctg cac ggc atg      48
Pro Val Ser Ile Gln Ala Phe Ala Ser Ser Ser Thr Leu His Gly Met
  1               5                  10                  15 gcc cac atc ttc tcc tac gag cgg ctg tct ctg aag cgg gca ctg tgg      96
Ala His Ile Phe Ser Tyr Glu Arg Leu Ser Leu Lys Arg Ala Leu Trp
                 20                  25                  30 gcc ctg tgc ttc ctg ggc tcg ctg gct gtg ctg ctg tgt gtg tgc acg     144
Ala Leu Cys Phe Leu Gly Ser Leu Ala Val Leu Leu Cys Val Cys Thr
             35                  40                  45 gag cgt gtg cag tac tac ttc cac tac cac cat gtc acc aag ctc gac     192
Glu Arg Val Gln Tyr Tyr Phe His Tyr His His Val Thr Lys Leu Asp
 50                  55                  60 gag gtg gct gcc tct cag ctt acc ttc cct gct gtc acg ctg tgc aac     240
Glu Val Ala Ala Ser Gln Leu Thr Phe Pro Ala Val Thr Leu Cys Asn
 65                  70                  75                  80 ctc aac gag ttc cgc ttt agc caa gtc tcc aag aat gac ctg tat cat     288
Leu Asn Glu Phe Arg Phe Ser Gln Val Ser Lys Asn Asp Leu Tyr His
                 85                  90                  95 gct ggg gag ctg ctg gcc ctg ctc aac aac agg tat gag ata cca gac     336
Ala Gly Glu Leu Leu Ala Leu Leu Asn Asn Arg Tyr Glu Ile Pro Asp
            100                 105                 110 aca cag atg gca gat gaa aag cag ctg gag ata ctg cag gac aaa gcc     384
Thr Gln Met Ala Asp Glu Lys Gln Leu Glu Ile Leu Gln Asp Lys Ala
        115                 120                 125 aac ttc cgc agc ttc aaa ccc aaa ccc ttc aac atg cgt gag ttc tac     432
Asn Phe Arg Ser Phe Lys Pro Lys Pro Phe Asn Met Arg Glu Phe Tyr
    130                 135                 140 gac cga gct ggg cac gac att cga gac atg ctg ctc tcc tgc cac ttc     480
Asp Arg Ala Gly His Asp Ile Arg Asp Met Leu Leu Ser Cys His Phe
145                 150                 155                 160 cgg ggg gag gtc tgc agc gct gaa gac ttc aag gtg gtc ttc aca cgc     528
Arg Gly Glu Val Cys Ser Ala Glu Asp Phe Lys Val Val Phe Thr Arg
                165                 170                 175 tat gga aag tgc tac acg ttc aac tcg ggc cga aat ggg cgg ccg cgg     576
Tyr Gly Lys Cys Tyr Thr Phe Asn Ser Gly Arg Asn Gly Arg Pro Arg
            180                 185                 190 ctg aag acc atg aag ggt ggg acg ggc aat ggg ctg gaa atc atg ctg     624
Leu Lys Thr Met Lys Gly Gly Thr Gly Asn Gly Leu Glu Ile Met Leu
        195                 200                 205 gac atc cag cag gac gag tac ctg cct gtg tgg ggg gag act gac gag     672
Asp Ile Gln Gln Asp Glu Tyr Leu Pro Val Trp Gly Glu Thr Asp Glu
    210                 215                 220 acg tct ttc gaa gca ggc atc aaa gtg cag atc cat agt cag gat gaa     720
Thr Ser Phe Glu Ala Gly Ile Lys Val Gln Ile His Ser Gln Asp Glu
225                 230                 235                 240 cct cct ttc atc gac cag ctg ggc ttt ggc gtg gcc cca ggc ttc cag     768
Pro Pro Phe Ile Asp Gln Leu Gly Phe Gly Val Ala Pro Gly Phe Gln
```

```
                          245                 250                 255
acc ttt gtg gcc tgc cag gag cag cgg ctc ata tac ctg ccc cca ccc        816
Thr Phe Val Ala Cys Gln Glu Gln Arg Leu Ile Tyr Leu Pro Pro Pro
                260                 265                 270 tgg ggc acc tgc aaa gct gtt acc atg gac tcg gat ttg gat ttc ttc        864
Trp Gly Thr Cys Lys Ala Val Thr Met Asp Ser Asp Leu Asp Phe Phe
            275                 280                 285 gac tcc tac agc atc act gcc tgc cgc atc gac tgt gag acg cgc tac        912
Asp Ser Tyr Ser Ile Thr Ala Cys Arg Ile Asp Cys Glu Thr Arg Tyr
        290                 295                 300 ctg gtg gag aac tgc aac tgc cgc atg gtg cac atg cca ggg gat gcc        960
Leu Val Glu Asn Cys Asn Cys Arg Met Val His Met Pro Gly Asp Ala
305                 310                 315                 320 cca tac tgt act cca gag cag tac aag gag tgt gca gat cct gct ctg       1008
Pro Tyr Cys Thr Pro Glu Gln Tyr Lys Glu Cys Ala Asp Pro Ala Leu
                325                 330                 335 gac ttc ctg gtg gag aag gac cag gag tac tgc gtg tgt gaa atg cct       1056
Asp Phe Leu Val Glu Lys Asp Gln Glu Tyr Cys Val Cys Glu Met Pro
            340                 345                 350 tgc aac ctg acc cgc tat ggc aaa gag ctg tcc atg gtc aag atc ccc       1104
Cys Asn Leu Thr Arg Tyr Gly Lys Glu Leu Ser Met Val Lys Ile Pro
        355                 360                 365 agc aaa gcc tca gcc aag tac ctg gcc aag aag ttc aac aaa tct gag       1152
Ser Lys Ala Ser Ala Lys Tyr Leu Ala Lys Lys Phe Asn Lys Ser Glu
    370                 375                 380 caa tac ata ggg gag aac atc ctg gtg ctg gac att ttc ttt gaa gtc       1200
Gln Tyr Ile Gly Glu Asn Ile Leu Val Leu Asp Ile Phe Phe Glu Val
385                 390                 395                 400 ctc aac tat gag acc att gaa cag aag aag gcc tat gag att gca ggg       1248
Leu Asn Tyr Glu Thr Ile Glu Gln Lys Lys Ala Tyr Glu Ile Ala Gly
                405                 410                 415 ctc ctg ggt gac atc ggg ggc cag atg ggg ctg ttc atc ggg gcc agc       1296
Leu Leu Gly Asp Ile Gly Gly Gln Met Gly Leu Phe Ile Gly Ala Ser
            420                 425                 430 atc ctc acg gtg ctg gag ctc ttt gac tac gcc tac ggg gtc att aag       1344
Ile Leu Thr Val Leu Glu Leu Phe Asp Tyr Ala Tyr Gly Val Ile Lys
        435                 440                 445 cac aag ctg tgc cga cga gga aaa tgc cag aag gag gcc aaa agg agc       1392
His Lys Leu Cys Arg Arg Gly Lys Cys Gln Lys Glu Ala Lys Arg Ser
    450                 455                 460 agt gcg gac aag ggc gtg gcc ctc agc ctg gac gac gtc aaa aga cac       1440
Ser Ala Asp Lys Gly Val Ala Leu Ser Leu Asp Asp Val Lys Arg His
465                 470                 475                 480 aac ccg tgc gag agc ctt cgg ggc cac cct gcc ggg atg aca tac gct       1488
Asn Pro Cys Glu Ser Leu Arg Gly His Pro Ala Gly Met Thr Tyr Ala
                485                 490                 495 gcc aac atc gta cct cac cat ccg gcc cga ggc acg ttc gag gac ttt       1536
Ala Asn Ile Val Pro His His Pro Ala Arg Gly Thr Phe Glu Asp Phe
            500                 505                 510 acc tgc tgagccccgc aggccgccga accaaagacc tagatgggga ggactaggag        1592
Thr Cys agcgaggggg cccccagctg cctcctaa                                        1620

<210> SEQ ID NO 4
<211> LENGTH: 514
<212> TYPE: PRT
<213> ORGANISM: Homo sapiens

<400> SEQUENCE: 4
```

-continued

```
Pro Val Ser Ile Gln Ala Phe Ala Ser Ser Thr Leu His Gly Met
 1               5                  10                 15

Ala His Ile Phe Ser Tyr Glu Arg Leu Ser Leu Lys Arg Ala Leu Trp
            20                  25                  30

Ala Leu Cys Phe Leu Gly Ser Leu Ala Val Leu Leu Cys Val Cys Thr
            35                  40                  45

Glu Arg Val Gln Tyr Tyr Phe His Tyr His Val Thr Lys Leu Asp
 50                  55                  60

Glu Val Ala Ala Ser Gln Leu Thr Phe Pro Ala Val Thr Leu Cys Asn
 65                  70                  75                  80

Leu Asn Glu Phe Arg Phe Ser Gln Val Ser Lys Asn Asp Leu Tyr His
                85                  90                  95

Ala Gly Glu Leu Leu Ala Leu Leu Asn Asn Arg Tyr Glu Ile Pro Asp
                100                 105                 110

Thr Gln Met Ala Asp Glu Lys Gln Leu Glu Ile Leu Gln Asp Lys Ala
                115                 120                 125

Asn Phe Arg Ser Phe Lys Pro Lys Pro Phe Asn Met Arg Glu Phe Tyr
        130                 135                 140

Asp Arg Ala Gly His Asp Ile Arg Asp Met Leu Leu Ser Cys His Phe
145                 150                 155                 160

Arg Gly Glu Val Cys Ser Ala Glu Asp Phe Lys Val Val Phe Thr Arg
                165                 170                 175

Tyr Gly Lys Cys Tyr Thr Phe Asn Ser Gly Arg Asn Gly Arg Pro Arg
            180                 185                 190

Leu Lys Thr Met Lys Gly Gly Thr Gly Asn Gly Leu Glu Ile Met Leu
            195                 200                 205

Asp Ile Gln Gln Asp Glu Tyr Leu Pro Val Trp Gly Glu Thr Asp Glu
        210                 215                 220

Thr Ser Phe Glu Ala Gly Ile Lys Val Gln Ile His Ser Gln Asp Glu
225                 230                 235                 240

Pro Pro Phe Ile Asp Gln Leu Gly Phe Gly Val Ala Pro Gly Phe Gln
                245                 250                 255

Thr Phe Val Ala Cys Gln Glu Gln Arg Leu Ile Tyr Leu Pro Pro Pro
                260                 265                 270

Trp Gly Thr Cys Lys Ala Val Thr Met Asp Ser Asp Leu Asp Phe Phe
        275                 280                 285

Asp Ser Tyr Ser Ile Thr Ala Cys Arg Ile Asp Cys Glu Thr Arg Tyr
        290                 295                 300

Leu Val Glu Asn Cys Asn Cys Arg Met Val His Met Pro Gly Asp Ala
305                 310                 315                 320

Pro Tyr Cys Thr Pro Glu Gln Tyr Lys Glu Cys Ala Asp Pro Ala Leu
                325                 330                 335

Asp Phe Leu Val Glu Lys Asp Gln Glu Tyr Cys Val Cys Glu Met Pro
            340                 345                 350

Cys Asn Leu Thr Arg Tyr Gly Lys Glu Leu Ser Met Val Lys Ile Pro
            355                 360                 365

Ser Lys Ala Ser Ala Lys Tyr Leu Ala Lys Lys Phe Asn Lys Ser Glu
        370                 375                 380

Gln Tyr Ile Gly Glu Asn Ile Leu Val Leu Asp Ile Phe Phe Glu Val
385                 390                 395                 400

Leu Asn Tyr Glu Thr Ile Glu Gln Lys Lys Ala Tyr Glu Ile Ala Gly
                405                 410                 415

Leu Leu Gly Asp Ile Gly Gly Gln Met Gly Leu Phe Ile Gly Ala Ser
```

-continued

```
                      420                 425                 430
Ile Leu Thr Val Leu Glu Leu Phe Asp Tyr Ala Tyr Gly Val Ile Lys
            435                 440                 445
His Lys Leu Cys Arg Arg Gly Lys Cys Gln Lys Glu Ala Lys Arg Ser
        450                 455                 460
Ser Ala Asp Lys Gly Val Ala Leu Ser Leu Asp Asp Val Lys Arg His
465                 470                 475                 480
Asn Pro Cys Glu Ser Leu Arg Gly His Pro Ala Gly Met Thr Tyr Ala
                485                 490                 495
Ala Asn Ile Val Pro His His Pro Ala Arg Gly Thr Phe Glu Asp Phe
                500                 505                 510
Thr Cys
```

<210> SEQ ID NO 5
<211> LENGTH: 1666
<212> TYPE: DNA
<213> ORGANISM: Homo sapiens
<220> FEATURE:
<221> NAME/KEY: CDS
<222> LOCATION: (128)..(1663)

<400> SEQUENCE: 5

```
tctggcgcga tgcttacctt gcgttctctc ccctgaacgt caaggtttaa gcagagcccg      60
aggactggga gctcttctct gaaattcgat caacctgaag ccagttgcgg aactgcacgg     120 ggtcccg atg gac ctc aag gaa agc ccc agt gag ggc agc ctg caa cct       169
        Met Asp Leu Lys Glu Ser Pro Ser Glu Gly Ser Leu Gln Pro
          1               5                  10 tct agc atc cag atc ttt gcc aac acc tcc acc ctc cat ggc atc cgc       217
Ser Ser Ile Gln Ile Phe Ala Asn Thr Ser Thr Leu His Gly Ile Arg
 15                  20                  25                  30 cac atc ttc gtg tat ggg ccg ctg acc atc cgg cgt gtg ctg tgg gca       265
His Ile Phe Val Tyr Gly Pro Leu Thr Ile Arg Arg Val Leu Trp Ala
                 35                  40                  45 gtg gcc ttc gtg ggc tct ctg ggc ctg ctg ctg gtg gag agc tct gag       313
Val Ala Phe Val Gly Ser Leu Gly Leu Leu Leu Val Glu Ser Ser Glu
             50                  55                  60 agg gtg tcc tac tac ttc tcc tac cag cat gtc act aag gtg gac gaa       361
Arg Val Ser Tyr Tyr Phe Ser Tyr Gln His Val Thr Lys Val Asp Glu
         65                  70                  75 gtg gtg gct caa agc ctg gtc ttc cca gct gtg acc ctc tgt aac ctc       409
Val Val Ala Gln Ser Leu Val Phe Pro Ala Val Thr Leu Cys Asn Leu
     80                  85                  90 aat ggc ttc cgg ttc tcc agg ctc acc acc aac gac ctg tac cat gct       457
Asn Gly Phe Arg Phe Ser Arg Leu Thr Thr Asn Asp Leu Tyr His Ala
 95                 100                 105                 110 ggg gag ctg ctg gcc ctg ctg gat gtc aac ctg cag atc ccg gac ccc       505
Gly Glu Leu Leu Ala Leu Leu Asp Val Asn Leu Gln Ile Pro Asp Pro
                115                 120                 125 cat ctg gct gac ccc tcc gtg ctg gag gcc ctg cgg cag aag gcc aac       553
His Leu Ala Asp Pro Ser Val Leu Glu Ala Leu Arg Gln Lys Ala Asn
            130                 135                 140 ttc aag cac tac aaa ccc aag cag ttc agc atg ctg gag ttc ctg cac       601
Phe Lys His Tyr Lys Pro Lys Gln Phe Ser Met Leu Glu Phe Leu His
        145                 150                 155 cgt gtg ggc cat gac ctg aag gat atg atg ctc tac tgc aag ttc aaa       649
Arg Val Gly His Asp Leu Lys Asp Met Met Leu Tyr Cys Lys Phe Lys
    160                 165                 170 ggg cag gag tgc ggc cac caa gac ttc acc aca gtg ttt aca aaa tat       697
```

```
Gly Gln Glu Cys Gly His Gln Asp Phe Thr Thr Val Phe Thr Lys Tyr
175                 180                 185                 190 ggg aag tgt tac atg ttt aac tca ggc gag gat ggc aaa cct ctg ctc        745
Gly Lys Cys Tyr Met Phe Asn Ser Gly Glu Asp Gly Lys Pro Leu Leu
                195                 200                 205 acc acg gtc aag ggg ggg aca ggc aac ggg ctg gag atc atg ctg gac        793
Thr Thr Val Lys Gly Gly Thr Gly Asn Gly Leu Glu Ile Met Leu Asp
            210                 215                 220 att cag cag gat gag tac ctg ccc atc tgg gga gag aca gag gaa acg        841
Ile Gln Gln Asp Glu Tyr Leu Pro Ile Trp Gly Glu Thr Glu Glu Thr
        225                 230                 235 aca ttt gaa gca gga gtg aaa gtt cag atc cac agt cag tct gag cca        889
Thr Phe Glu Ala Gly Val Lys Val Gln Ile His Ser Gln Ser Glu Pro
240                 245                 250 cct ttc atc caa gag ctg ggc ttt ggg gtg gct cca ggg ttc cag acc        937
Pro Phe Ile Gln Glu Leu Gly Phe Gly Val Ala Pro Gly Phe Gln Thr
255                 260                 265                 270 ttt gtg gcc aca cag gag cag agg ctc aca tac ctg ccc cca ccg tgg        985
Phe Val Ala Thr Gln Glu Gln Arg Leu Thr Tyr Leu Pro Pro Pro Trp
                275                 280                 285 ggt gag tgc cga tcc tca gag atg ggc ctc gac ttt ttt cct gtt tac       1033
Gly Glu Cys Arg Ser Ser Glu Met Gly Leu Asp Phe Phe Pro Val Tyr
            290                 295                 300 agc atc acc gcc tgt agg att gac tgt gag acc cgc tac att gtg gaa       1081
Ser Ile Thr Ala Cys Arg Ile Asp Cys Glu Thr Arg Tyr Ile Val Glu
        305                 310                 315 aac tgc aac tgc cgc atg gtt cac atg cca ggg gat gcc cct ttt tgt       1129
Asn Cys Asn Cys Arg Met Val His Met Pro Gly Asp Ala Pro Phe Cys
320                 325                 330 acc cct gag cag cac aag gag tgt gca gag cct gcc cta ggt ctg ttg       1177
Thr Pro Glu Gln His Lys Glu Cys Ala Glu Pro Ala Leu Gly Leu Leu
335                 340                 345                 350 gcg gaa aag gac agc aat tac tgt ctc tgc agg aca ccc tgc aac cta       1225
Ala Glu Lys Asp Ser Asn Tyr Cys Leu Cys Arg Thr Pro Cys Asn Leu
                355                 360                 365 acc cgc tac aac aaa gag ctc tcc atg gtg aag atc ccc agc aag aca       1273
Thr Arg Tyr Asn Lys Glu Leu Ser Met Val Lys Ile Pro Ser Lys Thr
            370                 375                 380 tca gcc aag tac ctt gag aag aaa ttt aac aaa tca gaa aaa tat atc       1321
Ser Ala Lys Tyr Leu Glu Lys Lys Phe Asn Lys Ser Glu Lys Tyr Ile
        385                 390                 395 tca gag aac atc ctt gtt ctg gat ata ttt ttt gaa gct ctc aat tat       1369
Ser Glu Asn Ile Leu Val Leu Asp Ile Phe Phe Glu Ala Leu Asn Tyr
400                 405                 410 gag aca att gaa cag aag aag gcg tat gaa gtt gct gcc tta ctt ggt       1417
Glu Thr Ile Glu Gln Lys Lys Ala Tyr Glu Val Ala Ala Leu Leu Gly
415                 420                 425                 430 gat att ggt ggt cag atg gga ttg ttc att ggt gct agt atc ctt aca       1465
Asp Ile Gly Gly Gln Met Gly Leu Phe Ile Gly Ala Ser Ile Leu Thr
                435                 440                 445 ata cta gag ctc ttt gat tat att tat gag ctg atc aaa gag aag cta       1513
Ile Leu Glu Leu Phe Asp Tyr Ile Tyr Glu Leu Ile Lys Glu Lys Leu
            450                 455                 460 tta gac ctg ctt ggc aaa gag gag gat gaa ggg agc cac gat gag aat       1561
Leu Asp Leu Leu Gly Lys Glu Glu Asp Glu Gly Ser His Asp Glu Asn
        465                 470                 475 gtg agt act tgt gac aca atg cca aac cac tct gaa acc atc agt cac       1609
Val Ser Thr Cys Asp Thr Met Pro Asn His Ser Glu Thr Ile Ser His
480                 485                 490
```

```
act gtg aac gtg ccc ctg cag acg acc ctg ggg acc ctg gaa gaa ata    1657
Thr Val Asn Val Pro Leu Gln Thr Thr Leu Gly Thr Leu Glu Glu Ile
495                 500                 505                 510 gcc tgc tga                                                         1666
Ala Cys <210> SEQ ID NO 6
<211> LENGTH: 512
<212> TYPE: PRT
<213> ORGANISM: Homo sapiens

<400> SEQUENCE: 6

Met Asp Leu Lys Glu Ser Pro Ser Glu Gly Ser Leu Gln Pro Ser Ser
  1               5                  10                  15

Ile Gln Ile Phe Ala Asn Thr Ser Thr Leu His Gly Ile Arg His Ile
                 20                  25                  30

Phe Val Tyr Gly Pro Leu Thr Ile Arg Arg Val Leu Trp Ala Val Ala
             35                  40                  45

Phe Val Gly Ser Leu Gly Leu Leu Val Glu Ser Ser Glu Arg Val
         50                  55                  60

Ser Tyr Tyr Phe Ser Tyr Gln His Val Thr Lys Val Asp Glu Val Val
 65                  70                  75                  80

Ala Gln Ser Leu Val Phe Pro Ala Val Thr Leu Cys Asn Leu Asn Gly
                 85                  90                  95

Phe Arg Phe Ser Arg Leu Thr Thr Asn Asp Leu Tyr His Ala Gly Glu
                100                 105                 110

Leu Leu Ala Leu Leu Asp Val Asn Leu Gln Ile Pro Asp Pro His Leu
            115                 120                 125

Ala Asp Pro Ser Val Leu Glu Ala Leu Arg Gln Lys Ala Asn Phe Lys
130                 135                 140

His Tyr Lys Pro Lys Gln Phe Ser Met Leu Glu Phe Leu His Arg Val
145                 150                 155                 160

Gly His Asp Leu Lys Asp Met Met Leu Tyr Cys Lys Phe Lys Gly Gln
                165                 170                 175

Glu Cys Gly His Gln Asp Phe Thr Thr Val Phe Thr Lys Tyr Gly Lys
            180                 185                 190

Cys Tyr Met Phe Asn Ser Gly Glu Asp Gly Lys Pro Leu Leu Thr Thr
        195                 200                 205

Val Lys Gly Gly Thr Gly Asn Gly Leu Glu Ile Met Leu Asp Ile Gln
210                 215                 220

Gln Asp Glu Tyr Leu Pro Ile Trp Gly Glu Thr Glu Thr Thr Phe
225                 230                 235                 240

Glu Ala Gly Val Lys Val Gln Ile His Ser Gln Ser Glu Pro Pro Phe
                245                 250                 255

Ile Gln Glu Leu Gly Phe Gly Val Ala Pro Gly Phe Gln Thr Phe Val
            260                 265                 270

Ala Thr Gln Glu Gln Arg Leu Thr Tyr Leu Pro Pro Pro Trp Gly Glu
        275                 280                 285

Cys Arg Ser Ser Glu Met Gly Leu Asp Phe Phe Pro Val Tyr Ser Ile
    290                 295                 300

Thr Ala Cys Arg Ile Asp Cys Glu Thr Arg Tyr Ile Val Glu Asn Cys
305                 310                 315                 320

Asn Cys Arg Met Val His Met Pro Gly Asp Ala Pro Phe Cys Thr Pro
                325                 330                 335

Glu Gln His Lys Glu Cys Ala Glu Pro Ala Leu Gly Leu Leu Ala Glu
```

-continued

```
                       340                 345                 350
Lys Asp Ser Asn Tyr Cys Leu Cys Arg Thr Pro Cys Asn Leu Thr Arg
                355                 360                 365
Tyr Asn Lys Glu Leu Ser Met Val Lys Ile Pro Ser Lys Thr Ser Ala
            370                 375                 380
Lys Tyr Leu Glu Lys Lys Phe Asn Lys Ser Glu Lys Tyr Ile Ser Glu
385                 390                 395                 400
Asn Ile Leu Val Leu Asp Ile Phe Phe Glu Ala Leu Asn Tyr Glu Thr
                405                 410                 415
Ile Glu Gln Lys Lys Ala Tyr Glu Val Ala Ala Leu Leu Gly Asp Ile
                420                 425                 430
Gly Gly Gln Met Gly Leu Phe Ile Gly Ala Ser Ile Leu Thr Ile Leu
            435                 440                 445
Glu Leu Phe Asp Tyr Ile Tyr Glu Leu Ile Lys Glu Lys Leu Leu Asp
            450                 455                 460
Leu Leu Gly Lys Glu Glu Asp Glu Gly Ser His Asp Glu Asn Val Ser
465                 470                 475                 480
Thr Cys Asp Thr Met Pro Asn His Ser Glu Thr Ile Ser His Thr Val
                485                 490                 495
Asn Val Pro Leu Gln Thr Thr Leu Gly Thr Leu Glu Glu Ile Ala Cys
            500                 505                 510
```

<210> SEQ ID NO 7
<211> LENGTH: 3647
<212> TYPE: DNA
<213> ORGANISM: rattus sp.
<220> FEATURE:
<221> NAME/KEY: CDS
<222> LOCATION: (109)..(1785)

<400> SEQUENCE: 7

```
ctgccacaga ggctctggtg aggaaggaca gacagctgga ccggcgcaga cctagccgaa      60
gtccaacctc cgtcccttct ggtggcttct tcctgtctcc tgaacaag atg ccc atc     117
                                                    Met Pro Ile
                                                      1 cag atc ttt tgt tct gtg tca ttc tcc tct gga gag gag gcc ccg gga      165
Gln Ile Phe Cys Ser Val Ser Phe Ser Ser Gly Glu Glu Ala Pro Gly
        5                  10                  15 tcc atg gca gat atc tgg ggt ccc cac cac cac cgg cag cag cag gac      213
Ser Met Ala Asp Ile Trp Gly Pro His His His Arg Gln Gln Gln Asp
 20                  25                  30                  35 agc tca gaa tcg gaa gaa gag gaa gag aag gaa atg gag gca ggg tcg      261
Ser Ser Glu Ser Glu Glu Glu Glu Lys Glu Met Glu Ala Gly Ser
                 40                  45                  50 gag ttg gat gag ggt gat gac tca cct agg gac ttg gtg gcc ttc gcc      309
Glu Leu Asp Glu Gly Asp Asp Ser Pro Arg Asp Leu Val Ala Phe Ala
             55                  60                  65 aac agc tgt acc ttc cat ggt gcc agc cat gtg ttt gtg gaa ggg ggc      357
Asn Ser Cys Thr Phe His Gly Ala Ser His Val Phe Val Glu Gly Gly
         70                  75                  80 cca ggg cca agg cag gcc tta tgg gca gtg gcc ttt gtc ata gca ctg      405
Pro Gly Pro Arg Gln Ala Leu Trp Ala Val Ala Phe Val Ile Ala Leu
     85                  90                  95 ggt gcc ttc ctg tgc cag gta ggg gac cgc gtt gct tat tac ctc agc      453
Gly Ala Phe Leu Cys Gln Val Gly Asp Arg Val Ala Tyr Tyr Leu Ser
100                 105                 110                 115 tac cca cac gtg act ttg cta gac gaa gtg gcc acc acg gag ctg gtc      501
Tyr Pro His Val Thr Leu Leu Asp Glu Val Ala Thr Thr Glu Leu Val
```

-continued

|  |  |  | 120 |  |  |  | 125 |  |  |  | 130 |  |  |  |
|---|---|---|---|---|---|---|---|---|---|---|---|---|---|---|
| ttc | cca | gct | gtc | acc | ttc | tgc | aac | acc | aat | gcc | gtg | cgg | ttg | tcc | cag | 549 |
| Phe | Pro | Ala | Val | Thr | Phe | Cys | Asn | Thr | Asn | Ala | Val | Arg | Leu | Ser | Gln |
|  |  |  | 135 |  |  |  | 140 |  |  |  | 145 |  |  |  |

```
ctc agc tac cct gac ttg ctc tac ctg gcc ccc atg cta gga ctg gat      597
Leu Ser Tyr Pro Asp Leu Leu Tyr Leu Ala Pro Met Leu Gly Leu Asp
        150                 155                 160 gag agt gat gac ccc ggg gtg ccc ctt gct cct cct ggc cca gag gct      645
Glu Ser Asp Asp Pro Gly Val Pro Leu Ala Pro Pro Gly Pro Glu Ala
165                 170                 175 ttc tcc ggg gag cct ttt aac ctc cat cgt ttc tat aat cgc tct tgc      693
Phe Ser Gly Glu Pro Phe Asn Leu His Arg Phe Tyr Asn Arg Ser Cys
180                 185                 190                 195 cac cgg ctg gag gac atg ctc cta tat tgt tcc tac tgt ggg ggc ccc      741
His Arg Leu Glu Asp Met Leu Leu Tyr Cys Ser Tyr Cys Gly Gly Pro
        200                 205                 210 tgt ggt ccc cac aac ttc tca gtg gtc ttc act cgg tat ggg aag tgt      789
Cys Gly Pro His Asn Phe Ser Val Val Phe Thr Arg Tyr Gly Lys Cys
        215                 220                 225 tac aca ttc aac tcg ggc caa gat ggg cgg cca cgg ctg aag acc atg      837
Tyr Thr Phe Asn Ser Gly Gln Asp Gly Arg Pro Arg Leu Lys Thr Met
        230                 235                 240 aaa ggt ggg act ggc aat ggc ctg gag atc atg ctg gac att cag caa      885
Lys Gly Gly Thr Gly Asn Gly Leu Glu Ile Met Leu Asp Ile Gln Gln
245                 250                 255 gat gaa tat ttg cct gtg tgg gga gag acc gac gag aca tcc ttc gaa      933
Asp Glu Tyr Leu Pro Val Trp Gly Glu Thr Asp Glu Thr Ser Phe Glu
260                 265                 270                 275 gca ggc atc aaa gtg cag atc cac agt cag gat gaa ccc cct ttc atc      981
Ala Gly Ile Lys Val Gln Ile His Ser Gln Asp Glu Pro Pro Phe Ile
        280                 285                 290 gac cag ctg ggc ttt ggt gtg gct cca ggt ttc cag acg ttt gtg tct      1029
Asp Gln Leu Gly Phe Gly Val Ala Pro Gly Phe Gln Thr Phe Val Ser
        295                 300                 305 tgc cag gag cag agg ctc atc tac ctg ccc tca ccc tgg ggc acc tgc      1077
Cys Gln Glu Gln Arg Leu Ile Tyr Leu Pro Ser Pro Trp Gly Thr Cys
        310                 315                 320 aat gct gtt acc atg gac tcg gat ttc ttc gac tcc tac agc atc act      1125
Asn Ala Val Thr Met Asp Ser Asp Phe Phe Asp Ser Tyr Ser Ile Thr
325                 330                 335 gcc tgc cgg att gat tgc gag acg cgt tac ctg gtg gag aac tgc aac      1173
Ala Cys Arg Ile Asp Cys Glu Thr Arg Tyr Leu Val Glu Asn Cys Asn
340                 345                 350                 355 tgc cgt atg gtg cac atg cca ggg gac gcc cca tac tgc act cca gag      1221
Cys Arg Met Val His Met Pro Gly Asp Ala Pro Tyr Cys Thr Pro Glu
        360                 365                 370 cag tac aag gag tgt gca gat cct gcc ctg gac ttc cta gtg gag aaa      1269
Gln Tyr Lys Glu Cys Ala Asp Pro Ala Leu Asp Phe Leu Val Glu Lys
        375                 380                 385 gac cag gaa tac tgc gtg tgt gag atg cct tgc aac ctg acc cgc tac      1317
Asp Gln Glu Tyr Cys Val Cys Glu Met Pro Cys Asn Leu Thr Arg Tyr
        390                 395                 400 ggc aag gag ctg tcc atg gtc aag atc cca agc aaa gcc tcc gcc aag      1365
Gly Lys Glu Leu Ser Met Val Lys Ile Pro Ser Lys Ala Ser Ala Lys
        405                 410                 415 tac ctg gcc aag aag ttc aac aaa tcg gag cag tac ata ggg gag aac      1413
Tyr Leu Ala Lys Lys Phe Asn Lys Ser Glu Gln Tyr Ile Gly Glu Asn
420                 425                 430                 435 att ctg gtg ctg gac att ttc ttt gaa gtc ctc aac tat gag acc atc      1461
```

```
Ile Leu Val Leu Asp Ile Phe Phe Glu Val Leu Asn Tyr Glu Thr Ile
            440                 445                 450 gag cag aaa aag gcc tat gag atc gca ggg ctg ttg ggt gac atc ggg         1509
Glu Gln Lys Lys Ala Tyr Glu Ile Ala Gly Leu Leu Gly Asp Ile Gly
            455                 460                 465 ggc cag atg ggg ttg ttc atc ggt gcc agc atc ctc acc gtg ctg gaa         1557
Gly Gln Met Gly Leu Phe Ile Gly Ala Ser Ile Leu Thr Val Leu Glu
            470                 475                 480 ctc ttt gac tat gcc tac gag gtc att aag cac agg ctg tgc aga cgt         1605
Leu Phe Asp Tyr Ala Tyr Glu Val Ile Lys His Arg Leu Cys Arg Arg
        485                 490                 495 gga aag tgc cag aag gag gct aag agg agc agc gca gac aag ggc gtg         1653
Gly Lys Cys Gln Lys Glu Ala Lys Arg Ser Ser Ala Asp Lys Gly Val
500                 505                 510                 515 gcg ctc agc ctg gat gac gtc aaa aga cac aat ccc tgc gag agc ctc         1701
Ala Leu Ser Leu Asp Asp Val Lys Arg His Asn Pro Cys Glu Ser Leu
                520                 525                 530 cga gga cat cct gcc ggg atg acg tac gct gcc aac atc cta cct cac         1749
Arg Gly His Pro Ala Gly Met Thr Tyr Ala Ala Asn Ile Leu Pro His
            535                 540                 545 cat ccc gct cga ggc acg ttt gag gac ttt acc tgc taagccctcg              1795
His Pro Ala Arg Gly Thr Phe Glu Asp Phe Thr Cys
        550                 555 caggccgctg taccaaaggc ctaggtgggg agggctgggg gagcaagggg cccccaactg        1855
cccccagcta ccctgtggac ttaactgcat tcctggtcag tggttccctc ttgtctgtgg        1915
tgagaaagga gtcttgacca tagagtcctc tcccagcctc tatcccatct ttttatttta       1975
atttaatcac atttgctctg taatattgct tgaggctggg gatcgtgatt tcccccccagt      2035 tcttttattg ttgagaatag ttttctctat tctgggtttt ctgttatttc aaatgaatct       2095
gcaaattgct cttcccatct ctatgaagaa ttgcgttgga attttgatgg ggattgtatt       2155
gaatctgtag attgcctttg gtaagatggc cattttttact atgttaatcc tgccaattca      2215
tgagcaaggg agatctttct atctctgaaa tctacttcag tttctttctt cagagacttg       2275
aagttcttgt cataaaaatc ttttggtta gagccacacc aagtatttt atattgtttg         2335 tgactattgt gaatggtgtc atttcccctaa tttccttctc agcctactta tcctttgagt      2395
agaggaaggc ttctgatttg tttgggttaa ttttataccc agctgctttg ctaaagttct       2455
ttatcaggtt taggtgttct ctggtggaac ttttggggtc acgtaagaat actattatat       2515
catctgcaaa tagtgatatt tcacttcttc ctttccaatt tctatccctc tggggacttt       2575
ttgttgtcta attgctctgg ctaggacttc aaattctata ttgaatagat agggagagag       2635
tgggcagcct tgtctagttc ctggttttcg tgggatcgct tcaaatttct ctccatttag       2695
tttgatattg gctactggtt tgctgtatat ggcttttact gtacttaggt atgggccttg       2755
aattcctgat atttccaaga cttttaacat gaagggttt tgaaatttgc caaatgcttt        2815
ctcagcatct aatgagatga tcatgtgccc tccccccacc ttgagtttgt ttatatagtg       2875
ggttacatga aaggatcatt tctaatagtc cacaagtctg ccaaatcttg ctgattgtga       2935
ctcatttcca tagcaggctc tataacttct ctaacagatt gcattaaact ctgcttgggg       2995
aaggcattac ctcttggttg aagcaatgtt gtagtttcta tgcctgctga gtaaatagcc       3055
tcaagtccaa gtacttgccc agactaatga tcaaacgtat ccaggagttc cataccagag       3115
atgtactctt ctctccttg aagtacattg ctggaagagt aattgtgttt gctagagata       3175
ctccttcgaa ctgcaaaaga aatctcttgg ctaagcatat aatcaagcct caggttttct       3235
```

-continued

```
ttttattaaa tagctgcttg taagaaagtg gacactaagc atatacctca aagggagaca    3295
gaatgactct gtgccttcac tgatggaagt ctgggttaca aattacatca aagaaccta     3355 tcatagtgaa acatctcatt ccctggtat aatcccttct agaaatacac ttgtgactct    3415
gaaatgttat aatcgtgaca actaggctgt tacagataca ccaagttaaa tttgatagag    3475
aaaccaggct tggagcctca tgtccatagg gcaagaggaa gatgctgagt gtttaaggtt    3535
ggtttgagcg aagaacaata ccttgtgtca caaaaatgaa aggaaaaag  aaaaaaggaa    3595 agaaggaaag aaagagagag aaagaaaaag aaagaaagaa aaaaaaaaaa aa            3647
```

<210> SEQ ID NO 8
<211> LENGTH: 559
<212> TYPE: PRT
<213> ORGANISM: rattus sp.

<400> SEQUENCE: 8

```
Met Pro Ile Gln Ile Phe Cys Ser Val Ser Phe Ser Gly Glu Glu
  1               5                  10                  15

Ala Pro Gly Ser Met Ala Asp Ile Trp Gly Pro His His Arg Gln
                 20                  25                  30

Gln Gln Asp Ser Ser Glu Ser Glu Glu Glu Glu Lys Glu Met Glu
             35                  40                  45

Ala Gly Ser Glu Leu Asp Glu Gly Asp Ser Pro Arg Asp Leu Val
         50                  55                  60

Ala Phe Ala Asn Ser Cys Thr Phe His Gly Ala Ser His Val Phe Val
 65                  70                  75                  80

Glu Gly Gly Pro Gly Pro Arg Gln Ala Leu Trp Ala Val Ala Phe Val
                 85                  90                  95

Ile Ala Leu Gly Ala Phe Leu Cys Gln Val Gly Asp Arg Val Ala Tyr
                100                 105                 110

Tyr Leu Ser Tyr Pro His Val Thr Leu Leu Asp Glu Val Ala Thr Thr
            115                 120                 125

Glu Leu Val Phe Pro Ala Val Thr Phe Cys Asn Thr Asn Ala Val Arg
        130                 135                 140

Leu Ser Gln Leu Ser Tyr Pro Asp Leu Leu Tyr Leu Ala Pro Met Leu
145                 150                 155                 160

Gly Leu Asp Glu Ser Asp Pro Gly Val Pro Leu Ala Pro Pro Gly
                165                 170                 175

Pro Glu Ala Phe Ser Gly Glu Pro Phe Asn Leu His Arg Phe Tyr Asn
                180                 185                 190

Arg Ser Cys His Arg Leu Glu Asp Met Leu Leu Tyr Cys Ser Tyr Cys
            195                 200                 205

Gly Gly Pro Cys Gly Pro His Asn Phe Ser Val Val Phe Thr Arg Tyr
        210                 215                 220

Gly Lys Cys Tyr Thr Phe Asn Ser Gly Gln Asp Gly Arg Pro Arg Leu
225                 230                 235                 240

Lys Thr Met Lys Gly Gly Thr Gly Asn Gly Leu Glu Ile Met Leu Asp
                245                 250                 255

Ile Gln Gln Asp Glu Tyr Leu Pro Val Trp Gly Glu Thr Asp Glu Thr
            260                 265                 270

Ser Phe Glu Ala Gly Ile Lys Val Gln Ile His Ser Gln Asp Glu Pro
        275                 280                 285

Pro Phe Ile Asp Gln Leu Gly Phe Gly Val Ala Pro Gly Phe Gln Thr
    290                 295                 300
```

```
Phe Val Ser Cys Gln Glu Gln Arg Leu Ile Tyr Leu Pro Ser Pro Trp
305                 310                 315                 320

Gly Thr Cys Asn Ala Val Thr Met Asp Ser Asp Phe Asp Ser Tyr
            325                 330                 335

Ser Ile Thr Ala Cys Arg Ile Asp Cys Glu Thr Arg Tyr Leu Val Glu
            340                 345                 350

Asn Cys Asn Cys Arg Met Val His Met Pro Gly Asp Ala Pro Tyr Cys
            355                 360                 365

Thr Pro Glu Gln Tyr Lys Glu Cys Ala Asp Pro Ala Leu Asp Phe Leu
370                 375                 380

Val Glu Lys Asp Gln Glu Tyr Cys Val Cys Glu Met Pro Cys Asn Leu
385                 390                 395                 400

Thr Arg Tyr Gly Lys Glu Leu Ser Met Val Lys Ile Pro Ser Lys Ala
                405                 410                 415

Ser Ala Lys Tyr Leu Ala Lys Lys Phe Asn Lys Ser Glu Gln Tyr Ile
                420                 425                 430

Gly Glu Asn Ile Leu Val Leu Asp Ile Phe Phe Glu Val Leu Asn Tyr
            435                 440                 445

Glu Thr Ile Glu Gln Lys Lys Ala Tyr Glu Ile Ala Gly Leu Leu Gly
450                 455                 460

Asp Ile Gly Gly Gln Met Gly Leu Phe Ile Gly Ala Ser Ile Leu Thr
465                 470                 475                 480

Val Leu Glu Leu Phe Asp Tyr Ala Tyr Glu Val Ile Lys His Arg Leu
                485                 490                 495

Cys Arg Arg Gly Lys Cys Gln Lys Glu Ala Lys Arg Ser Ser Ala Asp
                500                 505                 510

Lys Gly Val Ala Leu Ser Leu Asp Asp Val Lys Arg His Asn Pro Cys
            515                 520                 525

Glu Ser Leu Arg Gly His Pro Ala Gly Met Thr Tyr Ala Ala Asn Ile
            530                 535                 540

Leu Pro His His Pro Ala Arg Gly Thr Phe Glu Asp Phe Thr Cys
545                 550                 555

<210> SEQ ID NO 9
<211> LENGTH: 1602
<212> TYPE: DNA
<213> ORGANISM: rattus sp.
<220> FEATURE:
<221> NAME/KEY: CDS
<222> LOCATION: (1)..(1599)

<400> SEQUENCE: 9 atg aaa cct cgc tcc gga ctg gag gag gcc cag cgg cga cag gcc tca      48
Met Lys Pro Arg Ser Gly Leu Glu Glu Ala Gln Arg Arg Gln Ala Ser
  1               5                  10                  15 gac atc cgg gtg ttt gcc agc agc tgc aca atg cat ggt ctg ggc cac      96
Asp Ile Arg Val Phe Ala Ser Ser Cys Thr Met His Gly Leu Gly His
             20                  25                  30 atc ttt ggc cct gga ggc ctg acc ctg cgc cga ggg ctg tgg gcc aca     144
Ile Phe Gly Pro Gly Gly Leu Thr Leu Arg Arg Gly Leu Trp Ala Thr
         35                  40                  45 gct gtg ctc ctg tcg ctg gcg gcc ttc ctc tac cag gtg gct gag cgg     192
Ala Val Leu Leu Ser Leu Ala Ala Phe Leu Tyr Gln Val Ala Glu Arg
     50                  55                  60 gtt cgc tac tat ggg gag ttc cac cat aag acc acc ctg gat gag cgt     240
Val Arg Tyr Tyr Gly Glu Phe His His Lys Thr Thr Leu Asp Glu Arg
 65                  70                  75                  80
```

| | |
|---|---|
| gag agc cac cag ctc acc ttc cca gct gtg act ctg tgt aat atc aac<br>Glu Ser His Gln Leu Thr Phe Pro Ala Val Thr Leu Cys Asn Ile Asn<br>                          85                      90                      95 | 288 |
| cca ctg cgc cgc tca cgc ctc aca ccc aat gac ttg cac tgg gct gga<br>Pro Leu Arg Arg Ser Arg Leu Thr Pro Asn Asp Leu His Trp Ala Gly<br>            100                     105                    110 | 336 |
| aca gcg ctg ctg ggc ctg gac cct gct gaa cat gct gcc tac ctt cgt<br>Thr Ala Leu Leu Gly Leu Asp Pro Ala Glu His Ala Ala Tyr Leu Arg<br>115                      120                    125 | 384 |
| gca ctg ggc cag ccc ccc gca cca cct ggc ttc atg ccc agt ccg acc<br>Ala Leu Gly Gln Pro Pro Ala Pro Pro Gly Phe Met Pro Ser Pro Thr<br>130                      135                    140 | 432 |
| ttt gac atg gca caa ctc tac gcc aga gcc ggc cac tcc ctt gag gac<br>Phe Asp Met Ala Gln Leu Tyr Ala Arg Ala Gly His Ser Leu Glu Asp<br>145                  150                    155                    160 | 480 |
| atg ttg ttg gat tgc cga tac cgt ggc cag ccc tgt ggg cct gag aac<br>Met Leu Leu Asp Cys Arg Tyr Arg Gly Gln Pro Cys Gly Pro Glu Asn<br>                        165                    170                    175 | 528 |
| ttc aca gtg atc ttt act cga atg ggg caa tgc tac acc ttc aac tct<br>Phe Thr Val Ile Phe Thr Arg Met Gly Gln Cys Tyr Thr Phe Asn Ser<br>            180                     185                    190 | 576 |
| ggt gcc cac ggt gca gag ctg ctc acc act cca aag ggt ggt gct ggc<br>Gly Ala His Gly Ala Glu Leu Leu Thr Thr Pro Lys Gly Gly Ala Gly<br>195                      200                    205 | 624 |
| aac gga ctg gag att atg cta gat gta cag caa gag gag tat ctg ccc<br>Asn Gly Leu Glu Ile Met Leu Asp Val Gln Gln Glu Glu Tyr Leu Pro<br>210                      215                    220 | 672 |
| atc tgg aag gac atg gaa gag acc ccg ttt gag gtg ggg atc cga gtg<br>Ile Trp Lys Asp Met Glu Glu Thr Pro Phe Glu Val Gly Ile Arg Val<br>225                  230                    235                    240 | 720 |
| cag att cac agc cag gat gag ccc cct gcc att gac cag ctg ggc ttc<br>Gln Ile His Ser Gln Asp Glu Pro Pro Ala Ile Asp Gln Leu Gly Phe<br>                        245                    250                    255 | 768 |
| ggg gca gcc cca ggc cat cag act ttt gtg tcc tgt cag cag cag caa<br>Gly Ala Ala Pro Gly His Gln Thr Phe Val Ser Cys Gln Gln Gln Gln<br>260                      265                    270 | 816 |
| ctg agt ttc ctg cca cca ccc tgg ggt gac tgc aat acc gca tct ttg<br>Leu Ser Phe Leu Pro Pro Pro Trp Gly Asp Cys Asn Thr Ala Ser Leu<br>            275                     280                    285 | 864 |
| gat ccc gac gac ttt gat cca gag ccc tct gat ccc ttg ggt tcc ccc<br>Asp Pro Asp Asp Phe Asp Pro Glu Pro Ser Asp Pro Leu Gly Ser Pro<br>290                      295                    300 | 912 |
| aga ccc aga ccc agc cct cct tat agt tta ata ggt tgt cgc ctg gcc<br>Arg Pro Arg Pro Ser Pro Pro Tyr Ser Leu Ile Gly Cys Arg Leu Ala<br>305                  310                    315                    320 | 960 |
| tgt gag tct cgc tat gtg gct cgg aag tgt ggc tgt cga atg atg cat<br>Cys Glu Ser Arg Tyr Val Ala Arg Lys Cys Gly Cys Arg Met Met His<br>                        325                    330                    335 | 1008 |
| atg cct gga aac tcc cca gtg tgc agc ccc cag cag tac aag gac tgc<br>Met Pro Gly Asn Ser Pro Val Cys Ser Pro Gln Gln Tyr Lys Asp Cys<br>            340                     345                    350 | 1056 |
| gcc agc cca gct ctg gac gct atg ctg cga aag gac acg tgt gtc tgc<br>Ala Ser Pro Ala Leu Asp Ala Met Leu Arg Lys Asp Thr Cys Val Cys<br>355                      360                    365 | 1104 |
| ccc aac ccg tgc gct act aca cgc tat gcc aag gag ctc tcc atg gtg<br>Pro Asn Pro Cys Ala Thr Thr Arg Tyr Ala Lys Glu Leu Ser Met Val<br>370                      375                    380 | 1152 |
| cgg att ccc agc cgc gcg tca gct cgc tac ctg gcc cgg aaa tac aac<br>Arg Ile Pro Ser Arg Ala Ser Ala Arg Tyr Leu Ala Arg Lys Tyr Asn<br>385                  390                    395                    400 | 1200 |

-continued

```
cgc agc gag tcc tac att acg gag aat gta ctg gtt ctg gat atc ttc     1248
Arg Ser Glu Ser Tyr Ile Thr Glu Asn Val Leu Val Leu Asp Ile Phe
            405                 410                 415 ttt gag gcc ctc aac tat gaa gcg gtg gaa caa aag gcg gcc tat gaa     1296
Phe Glu Ala Leu Asn Tyr Glu Ala Val Glu Gln Lys Ala Ala Tyr Glu
        420                 425                 430 gtg tcg gag ctg ctg gga gac att ggg gga cag atg gga ctg ttt att     1344
Val Ser Glu Leu Leu Gly Asp Ile Gly Gly Gln Met Gly Leu Phe Ile
    435                 440                 445 gga gca agc ctg ctt acc atc ctt gag atc ctc gac tat ctc tgt gag     1392
Gly Ala Ser Leu Leu Thr Ile Leu Glu Ile Leu Asp Tyr Leu Cys Glu
450                 455                 460 gtt ttc caa gac aga gtc ctg ggg tat ttc tgg aac aga agg agc gct     1440
Val Phe Gln Asp Arg Val Leu Gly Tyr Phe Trp Asn Arg Arg Ser Ala
465                 470                 475                 480 caa aag cgc tct ggc aac act ctg ctc cag gaa gag ttg aat ggc cat     1488
Gln Lys Arg Ser Gly Asn Thr Leu Leu Gln Glu Glu Leu Asn Gly His
            485                 490                 495 cga aca cat gtt ccc cac ctc agc cta ggg ccc agg cct cct acc act     1536
Arg Thr His Val Pro His Leu Ser Leu Gly Pro Arg Pro Pro Thr Thr
        500                 505                 510 ccc tgt gct gtc acc aag aca ctc tct gcc tcc cac cgt acc tgt tac     1584
Pro Cys Ala Val Thr Lys Thr Leu Ser Ala Ser His Arg Thr Cys Tyr
    515                 520                 525 ctc gtc aca agg ctc tag                                             1602
Leu Val Thr Arg Leu
    530
```

<210> SEQ ID NO 10
<211> LENGTH: 533
<212> TYPE: PRT
<213> ORGANISM: rattus sp.

<400> SEQUENCE: 10

```
Met Lys Pro Arg Ser Gly Leu Glu Glu Ala Gln Arg Arg Gln Ala Ser
  1               5                  10                  15

Asp Ile Arg Val Phe Ala Ser Ser Cys Thr Met His Gly Leu Gly His
                 20                  25                  30

Ile Phe Gly Pro Gly Gly Leu Thr Leu Arg Arg Gly Leu Trp Ala Thr
             35                  40                  45

Ala Val Leu Leu Ser Leu Ala Ala Phe Leu Tyr Gln Val Ala Glu Arg
         50                  55                  60

Val Arg Tyr Tyr Gly Glu Phe His His Lys Thr Thr Leu Asp Glu Arg
 65                  70                  75                  80

Glu Ser His Gln Leu Thr Phe Pro Ala Val Thr Leu Cys Asn Ile Asn
                 85                  90                  95

Pro Leu Arg Arg Ser Arg Leu Thr Pro Asn Asp Leu His Trp Ala Gly
            100                 105                 110

Thr Ala Leu Leu Gly Leu Asp Pro Ala Glu His Ala Ala Tyr Leu Arg
        115                 120                 125

Ala Leu Gly Gln Pro Pro Ala Pro Pro Gly Phe Met Pro Ser Pro Thr
    130                 135                 140

Phe Asp Met Ala Gln Leu Tyr Ala Arg Ala Gly His Ser Leu Glu Asp
145                 150                 155                 160

Met Leu Leu Asp Cys Arg Tyr Arg Gly Gln Pro Cys Gly Pro Glu Asn
                165                 170                 175

Phe Thr Val Ile Phe Thr Arg Met Gly Gln Cys Tyr Thr Phe Asn Ser
```

180             185             190
Gly Ala His Gly Ala Glu Leu Leu Thr Thr Pro Lys Gly Gly Ala Gly
            195                 200                 205

Asn Gly Leu Glu Ile Met Leu Asp Val Gln Gln Glu Tyr Leu Pro
    210                 215                 220

Ile Trp Lys Asp Met Glu Glu Thr Pro Phe Glu Val Gly Ile Arg Val
225                 230                 235                 240

Gln Ile His Ser Gln Asp Glu Pro Pro Ala Ile Asp Gln Leu Gly Phe
                245                 250                 255

Gly Ala Ala Pro Gly His Gln Thr Phe Val Ser Cys Gln Gln Gln Gln
            260                 265                 270

Leu Ser Phe Leu Pro Pro Pro Trp Gly Asp Cys Asn Thr Ala Ser Leu
        275                 280                 285

Asp Pro Asp Asp Phe Asp Pro Glu Pro Ser Asp Pro Leu Gly Ser Pro
    290                 295                 300

Arg Pro Arg Pro Ser Pro Pro Tyr Ser Leu Ile Gly Cys Arg Leu Ala
305                 310                 315                 320

Cys Glu Ser Arg Tyr Val Ala Arg Lys Cys Gly Cys Arg Met Met His
                325                 330                 335

Met Pro Gly Asn Ser Pro Val Cys Ser Pro Gln Gln Tyr Lys Asp Cys
            340                 345                 350

Ala Ser Pro Ala Leu Asp Ala Met Leu Arg Lys Asp Thr Cys Val Cys
        355                 360                 365

Pro Asn Pro Cys Ala Thr Thr Arg Tyr Ala Lys Glu Leu Ser Met Val
    370                 375                 380

Arg Ile Pro Ser Arg Ala Ser Ala Arg Tyr Leu Ala Arg Lys Tyr Asn
385                 390                 395                 400

Arg Ser Glu Ser Tyr Ile Thr Glu Asn Val Leu Val Leu Asp Ile Phe
                405                 410                 415

Phe Glu Ala Leu Asn Tyr Glu Ala Val Glu Gln Lys Ala Ala Tyr Glu
            420                 425                 430

Val Ser Glu Leu Leu Gly Asp Ile Gly Gly Gln Met Gly Leu Phe Ile
        435                 440                 445

Gly Ala Ser Leu Leu Thr Ile Leu Glu Ile Leu Asp Tyr Leu Cys Glu
    450                 455                 460

Val Phe Gln Asp Arg Val Leu Gly Tyr Phe Trp Asn Arg Arg Ser Ala
465                 470                 475                 480

Gln Lys Arg Ser Gly Asn Thr Leu Leu Gln Glu Leu Asn Gly His
                485                 490                 495

Arg Thr His Val Pro His Leu Ser Leu Gly Pro Arg Pro Thr Thr
            500                 505                 510

Pro Cys Ala Val Thr Lys Thr Leu Ser Ala Ser His Arg Thr Cys Tyr
        515                 520                 525

Leu Val Thr Arg Leu
        530

<210> SEQ ID NO 11
<211> LENGTH: 1948
<212> TYPE: DNA
<213> ORGANISM: rattus sp.
<220> FEATURE:
<221> NAME/KEY: CDS
<222> LOCATION: (16)..(1704)

<400> SEQUENCE: 11

```
cctcgggctg aatga atg agc cgg agc ggc gga gcc cgg ctg ccc gcg acc         51
              Met Ser Arg Ser Gly Gly Ala Arg Leu Pro Ala Thr
                1               5                  10 gcg ctc agc ggc ccg gga cgc ttc cgt atg gcc cgc gag cag ccg gcg         99
Ala Leu Ser Gly Pro Gly Arg Phe Arg Met Ala Arg Glu Gln Pro Ala
         15                  20                  25 ccc gtg gcg gtg gcg gca gct agg cag ccc gga gga gac cgg agc ggc        147
Pro Val Ala Val Ala Ala Ala Arg Gln Pro Gly Gly Asp Arg Ser Gly
 30                  35                  40 gat ccg gcg ctg cag ggg cca ggg gtc gcc cgc agg ggg cgg ccg tcc        195
Asp Pro Ala Leu Gln Gly Pro Gly Val Ala Arg Arg Gly Arg Pro Ser
 45                  50                  55                  60 ctg agt cgc act aaa ttg cac ggg ctg cgg cac atg tgc gcg ggg cgc        243
Leu Ser Arg Thr Lys Leu His Gly Leu Arg His Met Cys Ala Gly Arg
             65                  70                  75 acg gcg gcg gga ggc tct ttc cag cga cgg gcg ctg tgg gtg ctg gcc        291
Thr Ala Ala Gly Gly Ser Phe Gln Arg Arg Ala Leu Trp Val Leu Ala
                 80                  85                  90 ttc tgc acg tcc ctc ggc ttg ctg ctc tcc tgg tcc tcg aac cgc ctg        339
Phe Cys Thr Ser Leu Gly Leu Leu Leu Ser Trp Ser Ser Asn Arg Leu
                     95                 100                 105 ctc tac tgg ctc agc ttc ccg tca cac aca cga gtg cac cgt gag tgg        387
Leu Tyr Trp Leu Ser Phe Pro Ser His Thr Arg Val His Arg Glu Trp
110                 115                 120 agc cgc cag ctg ccg ttc ccc gcc gtc acc gtg tgc aac aac aac ccc        435
Ser Arg Gln Leu Pro Phe Pro Ala Val Thr Val Cys Asn Asn Asn Pro
125                 130                 135                 140 ctg cgc ttc ccg cgc ctc tcc aag ggg gac ctc tac tac gcg ggc cac        483
Leu Arg Phe Pro Arg Leu Ser Lys Gly Asp Leu Tyr Tyr Ala Gly His
                145                 150                 155 tgg cta ggg ctg ctg ctt ccc aac cgc acc gcg cgc ccg ctg gtc agc        531
Trp Leu Gly Leu Leu Leu Pro Asn Arg Thr Ala Arg Pro Leu Val Ser
            160                 165                 170 gag ctg ctg cgg ggc gac gag ccg cgc cgc cag tgg ttc cgc aaa ctg        579
Glu Leu Leu Arg Gly Asp Glu Pro Arg Arg Gln Trp Phe Arg Lys Leu
                175                 180                 185 gcc gac ttc cgc ctc ttc ctg ccg ccg cgc cac ttc gag ggc atc agc        627
Ala Asp Phe Arg Leu Phe Leu Pro Pro Arg His Phe Glu Gly Ile Ser
190                 195                 200 gct gcc ttc atg gac cgt ttg ggc cac cag ctg gag gat atg ctg ctc        675
Ala Ala Phe Met Asp Arg Leu Gly His Gln Leu Glu Asp Met Leu Leu
205                 210                 215                 220 tcc tgc aag tac cgg ggc gag ctc tgt ggc ccg cac aac ttc tcc tca        723
Ser Cys Lys Tyr Arg Gly Glu Leu Cys Gly Pro His Asn Phe Ser Ser
                225                 230                 235 gtg ttt aca aaa tac ggg aag tgt tac atg ttt aac tca ggc gag gat        771
Val Phe Thr Lys Tyr Gly Lys Cys Tyr Met Phe Asn Ser Gly Glu Asp
                    240                 245                 250 ggc aag ccg ctg ctc acc acg gtc aag ggg ggg acg ggc aac ggg ctg        819
Gly Lys Pro Leu Leu Thr Thr Val Lys Gly Gly Thr Gly Asn Gly Leu
        255                 260                 265 gag atc atg ctg gac att cag caa gat gag tac ctg ccc atc tgg gga        867
Glu Ile Met Leu Asp Ile Gln Gln Asp Glu Tyr Leu Pro Ile Trp Gly
    270                 275                 280 gag aca gag gaa aca acg ttt gaa gca gga gtg aag gtt cag atc cac        915
Glu Thr Glu Glu Thr Thr Phe Glu Ala Gly Val Lys Val Gln Ile His
285                 290                 295                 300 agt cag tct gag ccg cct ttc atc caa gag ctg ggc ttt ggg gtg gct        963
Ser Gln Ser Glu Pro Pro Phe Ile Gln Glu Leu Gly Phe Gly Val Ala
                305                 310                 315
```

-continued

| | |
|---|---|
| ccg ggg ttc cag acc ttc gtg gcc aca caa gag cag agg ctc aca tat<br>Pro Gly Phe Gln Thr Phe Val Ala Thr Gln Glu Gln Arg Leu Thr Tyr<br>320                             325                     330 | 1011 |
| ctg ccc cca cca tgg ggg gag tgc cgg tcc tca gag atg gga ctc gac<br>Leu Pro Pro Pro Trp Gly Glu Cys Arg Ser Ser Glu Met Gly Leu Asp<br>     335                         340                    345 | 1059 |
| ttc ttt cct gtt tac agc atc aca gcc tgt cgg att gac tgt gag acc<br>Phe Phe Pro Val Tyr Ser Ile Thr Ala Cys Arg Ile Asp Cys Glu Thr<br>350                           355                     360 | 1107 |
| cgc tac atc gtg gag aac tgt aac tgc cgc atg gtc cac atg cca ggg<br>Arg Tyr Ile Val Glu Asn Cys Asn Cys Arg Met Val His Met Pro Gly<br>365                          370                    375             380 | 1155 |
| gac gcc cct ttc tgc acc cct gag cag cac aag gag tgt gca gag cct<br>Asp Ala Pro Phe Cys Thr Pro Glu Gln His Lys Glu Cys Ala Glu Pro<br>                   385                     390                 395 | 1203 |
| gcc ctc ggt cta ctg gca gaa aag gac agc aat tac tgt ctc tgc agg<br>Ala Leu Gly Leu Leu Ala Glu Lys Asp Ser Asn Tyr Cys Leu Cys Arg<br>              400                     405                    410 | 1251 |
| aca ccc tgc aac ctg aca cgc tac aac aaa gag ctc tcc atg gtg aag<br>Thr Pro Cys Asn Leu Thr Arg Tyr Asn Lys Glu Leu Ser Met Val Lys<br>415                           420                    425 | 1299 |
| atc ccc agc aag acg tca gcc aag tac tta gag aag aaa ttt aac aaa<br>Ile Pro Ser Lys Thr Ser Ala Lys Tyr Leu Glu Lys Lys Phe Asn Lys<br>     430                         435                    440 | 1347 |
| tcg gaa aaa tat atc tca gag aac att ctt gtt ctg gac ata ttt ttt<br>Ser Glu Lys Tyr Ile Ser Glu Asn Ile Leu Val Leu Asp Ile Phe Phe<br>445                           450                    455             460 | 1395 |
| gag gcg ctc aat tac gaa aca att gaa cag aag aag gcg tat gaa gtt<br>Glu Ala Leu Asn Tyr Glu Thr Ile Glu Gln Lys Lys Ala Tyr Glu Val<br>                   465                     470                 475 | 1443 |
| gct gcc tta ctt ggt gac atc ggt ggt cag atg gga ctg ttc att ggt<br>Ala Ala Leu Leu Gly Asp Ile Gly Gly Gln Met Gly Leu Phe Ile Gly<br>              480                     485                    490 | 1491 |
| gct agt ctc ctc aca ata cta gag ctc ttt gat tat att tat gag ctg<br>Ala Ser Leu Leu Thr Ile Leu Glu Leu Phe Asp Tyr Ile Tyr Glu Leu<br>495                           500                    505 | 1539 |
| atc aaa gag aag cta tta gac ctg ctt ggc aaa gaa gaa gag gaa ggg<br>Ile Lys Glu Lys Leu Leu Asp Leu Leu Gly Lys Glu Glu Glu Glu Gly<br>     510                         515                    520 | 1587 |
| agc cac gat gag aac atg agc acc tgt gac aca atg cca aac cac tct<br>Ser His Asp Glu Asn Met Ser Thr Cys Asp Thr Met Pro Asn His Ser<br>525                           530                    535             540 | 1635 |
| gaa acc atc agc cac act gtg aac gtg ccc ctg cag aca gct ttg ggc<br>Glu Thr Ile Ser His Thr Val Asn Val Pro Leu Gln Thr Ala Leu Gly<br>              545                     550                    555 | 1683 |
| acc ctg gag gag att gcc tgc tgacacctct caggcaacgc agcacctcca<br>Thr Leu Glu Glu Ile Ala Cys<br>              560 | 1734 |
| aacagacctt aaaggcccaa gacctaggac aggagacagc aagcgcaggt gggatcgccc | 1794 |
| ctgacgactg aaagaagcag agccccccat atgcacacat tgcgaacttc tgccaaacct | 1854 |
| cacctggcca catctgacat gaaccgtccc gggccctgcg tcatgtccct cgcaggaccg | 1914 |
| atgagtcgca ctccggaact gtccaagaac taac | 1948 |

<210> SEQ ID NO 12
<211> LENGTH: 563
<212> TYPE: PRT
<213> ORGANISM: rattus sp.

```
<400> SEQUENCE: 12

Met Ser Arg Ser Gly Gly Ala Arg Leu Pro Ala Thr Ala Leu Ser Gly
 1               5                  10                  15

Pro Gly Arg Phe Arg Met Ala Arg Glu Gln Pro Ala Pro Val Ala Val
            20                  25                  30

Ala Ala Ala Arg Gln Pro Gly Gly Asp Arg Ser Gly Asp Pro Ala Leu
        35                  40                  45

Gln Gly Pro Gly Val Ala Arg Arg Gly Arg Pro Ser Leu Ser Arg Thr
    50                  55                  60

Lys Leu His Gly Leu Arg His Met Cys Ala Gly Arg Thr Ala Ala Gly
 65                  70                  75                  80

Gly Ser Phe Gln Arg Arg Ala Leu Trp Val Leu Ala Phe Cys Thr Ser
                85                  90                  95

Leu Gly Leu Leu Leu Ser Trp Ser Ser Asn Arg Leu Leu Tyr Trp Leu
            100                 105                 110

Ser Phe Pro Ser His Thr Arg Val His Arg Glu Trp Ser Arg Gln Leu
        115                 120                 125

Pro Phe Pro Ala Val Thr Val Cys Asn Asn Pro Leu Arg Phe Pro
    130                 135                 140

Arg Leu Ser Lys Gly Asp Leu Tyr Tyr Ala Gly His Trp Leu Gly Leu
145                 150                 155                 160

Leu Leu Pro Asn Arg Thr Ala Arg Pro Leu Val Ser Glu Leu Leu Arg
                165                 170                 175

Gly Asp Glu Pro Arg Arg Gln Trp Phe Arg Lys Leu Ala Asp Phe Arg
            180                 185                 190

Leu Phe Leu Pro Pro Arg His Phe Glu Gly Ile Ser Ala Ala Phe Met
        195                 200                 205

Asp Arg Leu Gly His Gln Leu Glu Asp Met Leu Leu Ser Cys Lys Tyr
    210                 215                 220

Arg Gly Glu Leu Cys Gly Pro His Asn Phe Ser Ser Val Phe Thr Lys
225                 230                 235                 240

Tyr Gly Lys Cys Tyr Met Phe Asn Ser Gly Glu Asp Gly Lys Pro Leu
                245                 250                 255

Leu Thr Thr Val Lys Gly Gly Thr Gly Asn Gly Leu Glu Ile Met Leu
            260                 265                 270

Asp Ile Gln Gln Asp Glu Tyr Leu Pro Ile Trp Gly Glu Thr Glu Glu
        275                 280                 285

Thr Thr Phe Glu Ala Gly Val Lys Val Gln Ile His Ser Gln Ser Glu
    290                 295                 300

Pro Pro Phe Ile Gln Glu Leu Gly Phe Gly Val Ala Pro Gly Phe Gln
305                 310                 315                 320

Thr Phe Val Ala Thr Gln Glu Gln Arg Leu Thr Tyr Leu Pro Pro
                325                 330                 335

Trp Gly Glu Cys Arg Ser Ser Glu Met Gly Leu Asp Phe Phe Pro Val
            340                 345                 350

Tyr Ser Ile Thr Ala Cys Arg Ile Asp Cys Glu Thr Arg Tyr Ile Val
        355                 360                 365

Glu Asn Cys Asn Cys Arg Met Val His Met Pro Gly Asp Ala Pro Phe
    370                 375                 380

Cys Thr Pro Glu Gln His Lys Glu Cys Ala Glu Pro Ala Leu Gly Leu
385                 390                 395                 400

Leu Ala Glu Lys Asp Ser Asn Tyr Cys Leu Cys Arg Thr Pro Cys Asn
                405                 410                 415
```

```
Leu Thr Arg Tyr Asn Lys Glu Leu Ser Met Val Lys Ile Pro Ser Lys
            420                 425                 430

Thr Ser Ala Lys Tyr Leu Glu Lys Lys Phe Asn Lys Ser Glu Lys Tyr
        435                 440                 445

Ile Ser Glu Asn Ile Leu Val Leu Asp Ile Phe Phe Glu Ala Leu Asn
    450                 455                 460

Tyr Glu Thr Ile Glu Gln Lys Lys Ala Tyr Glu Val Ala Ala Leu Leu
465                 470                 475                 480

Gly Asp Ile Gly Gly Gln Met Gly Leu Phe Ile Gly Ala Ser Leu Leu
                485                 490                 495

Thr Ile Leu Glu Leu Phe Asp Tyr Ile Tyr Glu Leu Ile Lys Glu Lys
            500                 505                 510

Leu Leu Asp Leu Leu Gly Lys Glu Glu Glu Gly Ser His Asp Glu
        515                 520                 525

Asn Met Ser Thr Cys Asp Thr Met Pro Asn His Ser Glu Thr Ile Ser
    530                 535                 540

His Thr Val Asn Val Pro Leu Gln Thr Ala Leu Gly Thr Leu Glu Glu
545                 550                 555                 560

Ile Ala Cys
```

<210> SEQ ID NO 13
<211> LENGTH: 1736
<212> TYPE: DNA
<213> ORGANISM: Homo sapiens

<400> SEQUENCE: 13

```
acgacgggt  tctggccatg  aagcccacct  caggcccaga  ggaggcccgg  cggccagcct    60
cggacatccg  cgtgttcgcc  agcaactgct  cgatgcacgg  gctgggccac  gtcttcgggc   120
caggcagcct  gagcctgcgc  cggggatgt   gggcagcggc  cgtggtcctg  tcagtggcca   180
ccttcctcta  ccaggtggct  gagagggtgc  gctactacag  ggagttccac  caccagactg   240
ccctggatga  gcgagaaagc  caccggctca  tcttcccggc  tgtcaccctg  tgcaacatca   300
acccactgcg  ccgctcgcgc  ctaacgccca  cgacctgca   ctgggctggg  tctgcgctgc   360
tgggcctgga  tcccgcagag  cacgccgcct  tcctgcgcgc  cctgggccgg  cccctgcac    420
cgcccggctt  catgcccagt  cccaccttg   acatggcgca  actctatgcc  cgtgctgggc   480
actccctgga  tgacatgctg  ctggactgtc  gcttccgtgg  ccaaccttgt  gggcctgaga   540
acttcaccac  gatcttcacc  cggatgggaa  agtgctacac  atttaactct  ggcgctgatg   600
gggcagagct  gctcaccact  actaggggtg  gcatgggcaa  tgggctggac  atcatgctgg   660
acgtgcagca  ggaggaatat  ctacctgtgt  ggagggacaa  tgaggagacc  ccgtttgagg   720
tggggatccg  agtgcagatc  acagccagg   aggagccgcc  catcatcgat  cagctgggct   780
tgggggtgtc  cccgggctac  cagaccttg   tttcttgcca  gcagcagcag  ctgagcttcc   840
tgccaccgcc  ctggggcgat  tgcagttcag  catctctgaa  ccccaactat  gagccagagc   900
cctctgatcc  cctaggctcc  cccagcccca  gcccagccc   tccctatacc  cttatgggt   960
gtcgcctggc  ctgcgaaacc  cgctacgtgg  ctcggaagtg  cggctgccga  atggtgtaca   1020
tgccaggcga  cgtgccagtg  tgcagccccc  agcagtacaa  gaactgtgcc  cacccggcca   1080
tagatgccat  gcttcgcaag  gactcgtgcg  cctgccccaa  ccgtgcgcc   agcacgcgct   1140
acgccaagga  gctctccatg  gtgcggatcc  cgagccgcg   cgccgcgcgc  ttcctggccc   1200
ggaagctcaa  ccgcagcgag  gcctacatcg  cggagaacgt  gctggccctg  gacatcttct  1260
```

-continued

```
ttgaggccct caactatgag accgtggagc agaagaaggc ctatgagatg tcagagctgc      1320
ttggtgacat tgggggccag atggggctgt tcatcggggc cagcctgctc accatcctcg      1380
agatcctaga ctacctctgt gaggtgttcc gagacaaggt cctgggatat ttctggaacc      1440
gacagcactc ccaaaggcac tccagcacca atctgcttca ggaagggctg ggcagccatc      1500
gaacccaagt tccccacctc agcctgggcc ccagacctcc caccctcccc tgtgccgtca      1560
ccaagactct ctccgcctcc caccgcacct gctaccttgt cacacagctc tagacctgct      1620
gtctgtgtcc tcggagcccc gccctgacat cctggacatg cctagcctgc acgtagcttt      1680
tccgtcttca ccccaaataa agtcctaatg catcaaaaaa aaaaaaaaaa aaaaaa         1736
```

<210> SEQ ID NO 14
<211> LENGTH: 531
<212> TYPE: PRT
<213> ORGANISM: Homo sapiens

<400> SEQUENCE: 14

```
Met Lys Pro Thr Ser Gly Pro Glu Glu Ala Arg Arg Pro Ala Ser Asp
 1               5                  10                  15

Ile Arg Val Phe Ala Ser Asn Cys Ser Met His Gly Leu Gly His Val
                20                  25                  30

Phe Gly Pro Gly Ser Leu Ser Leu Arg Arg Gly Met Trp Ala Ala Ala
            35                  40                  45

Val Val Leu Ser Val Ala Thr Phe Leu Tyr Gln Val Ala Glu Arg Val
        50                  55                  60

Arg Tyr Tyr Arg Glu Phe His His Gln Thr Ala Leu Asp Glu Arg Glu
 65                  70                  75                  80

Ser His Arg Leu Ile Phe Pro Ala Val Thr Leu Cys Asn Ile Asn Pro
                85                  90                  95

Leu Arg Arg Ser Arg Leu Thr Pro Asn Asp Leu His Trp Ala Gly Ser
                100                 105                 110

Ala Leu Leu Gly Leu Asp Pro Ala Glu His Ala Ala Phe Leu Arg Ala
            115                 120                 125

Leu Gly Arg Pro Pro Ala Pro Pro Gly Phe Met Pro Ser Pro Thr Phe
        130                 135                 140

Asp Met Ala Gln Leu Tyr Ala Arg Ala Gly His Ser Leu Asp Asp Met
145                 150                 155                 160

Leu Leu Asp Cys Arg Phe Arg Gly Gln Pro Cys Gly Pro Glu Asn Phe
                165                 170                 175

Thr Thr Ile Phe Thr Arg Met Gly Lys Cys Tyr Thr Phe Asn Ser Gly
                180                 185                 190

Ala Asp Gly Ala Glu Leu Leu Thr Thr Thr Arg Gly Gly Met Gly Asn
            195                 200                 205

Gly Leu Asp Ile Met Leu Asp Val Gln Gln Glu Glu Tyr Leu Pro Val
        210                 215                 220

Trp Arg Asp Asn Glu Glu Thr Pro Phe Glu Val Gly Ile Arg Val Gln
225                 230                 235                 240

Ile His Ser Gln Glu Glu Pro Pro Ile Ile Asp Gln Leu Gly Leu Gly
                245                 250                 255

Val Ser Pro Gly Tyr Gln Thr Phe Val Ser Cys Gln Gln Gln Gln Leu
                260                 265                 270

Ser Phe Leu Pro Pro Pro Trp Gly Asp Cys Ser Ser Ala Ser Leu Asn
            275                 280                 285
```

```
Pro Asn Tyr Glu Pro Glu Pro Ser Asp Pro Leu Gly Ser Pro Ser Pro
    290                 295                 300

Ser Pro Ser Pro Pro Tyr Thr Leu Met Gly Cys Arg Leu Ala Cys Glu
305                 310                 315                 320

Thr Arg Tyr Val Ala Arg Lys Cys Gly Cys Arg Met Val Tyr Met Pro
                325                 330                 335

Gly Asp Val Pro Val Cys Ser Pro Gln Gln Tyr Lys Asn Cys Ala His
            340                 345                 350

Pro Ala Ile Asp Ala Met Leu Arg Lys Asp Ser Cys Ala Cys Pro Asn
        355                 360                 365

Pro Cys Ala Ser Thr Arg Tyr Ala Lys Glu Leu Ser Met Val Arg Ile
    370                 375                 380

Pro Ser Arg Ala Ala Arg Phe Leu Ala Arg Lys Leu Asn Arg Ser
385                 390                 395                 400

Glu Ala Tyr Ile Ala Glu Asn Val Leu Ala Leu Asp Ile Phe Phe Glu
                405                 410                 415

Ala Leu Asn Tyr Glu Thr Val Glu Gln Lys Ala Tyr Glu Met Ser
            420                 425                 430

Glu Leu Leu Gly Asp Ile Gly Gly Gln Met Gly Leu Phe Ile Gly Ala
        435                 440                 445

Ser Leu Leu Thr Ile Leu Glu Ile Leu Asp Tyr Leu Cys Glu Val Phe
    450                 455                 460

Arg Asp Lys Val Leu Gly Tyr Phe Trp Asn Arg Gln His Ser Gln Arg
465                 470                 475                 480

His Ser Ser Thr Asn Leu Leu Gln Glu Gly Leu Gly Ser His Arg Thr
                485                 490                 495

Gln Val Pro His Leu Ser Leu Gly Pro Arg Pro Thr Pro Pro Cys
            500                 505                 510

Ala Val Thr Lys Thr Leu Ser Ala Ser His Arg Thr Cys Tyr Leu Val
        515                 520                 525

Thr Gln Leu
    530

<210> SEQ ID NO 15
<211> LENGTH: 625
<212> TYPE: PRT
<213> ORGANISM: Helix aspersa

<400> SEQUENCE: 15

Met Lys Tyr Thr Ser Ala Ala Thr Lys Pro Gly Val Phe Pro Glu His
 1               5                  10                  15

His Gln His Ala Met Met Arg Asn Arg Tyr His Pro His Cys Asn
            20                  25                  30

Tyr Ser Asp Asn Arg Ser Ala Ile Asp Ile Ala Glu Leu Gly Ser
        35                  40                  45

Glu Ser Asn Ala His Gly Leu Ala Lys Ile Val Thr Ser Arg Asp Thr
    50                  55                  60

Lys Arg Lys Val Ile Trp Ala Leu Leu Val Ile Ala Gly Phe Thr Ala
65                  70                  75                  80

Ala Thr Leu Gln Leu Ser Leu Leu Val Arg Lys Tyr Leu Gln Phe Gln
                85                  90                  95

Val Val Glu Leu Ser Glu Ile Lys Asp Ser Met Pro Val Gln Tyr Pro
            100                 105                 110

Ser Val Ser Ile Cys Asn Ile Glu Pro Ile Ser Leu Arg Thr Ile Arg
        115                 120                 125
```

-continued

```
Arg Met Tyr Phe Asn Asn Glu Ser Gln Asn Leu Ile Thr Trp Leu Arg
    130                 135                 140
Phe Ile Gln Lys Phe Arg Phe Glu Gln Asp Ser Phe Met Asn Ser Ile
145                 150                 155                 160
Arg Ala Phe Tyr Glu Asn Leu Gly Gln Asp Ala Lys Lys Leu Ser His
                165                 170                 175
Asn Leu Glu Asp Met Leu Met His Cys Arg Phe Asn Arg Glu Leu Cys
                180                 185                 190
His Val Ser Asn Phe Ser Thr Phe Phe Asp Gly Asn Tyr Phe Asn Cys
                195                 200                 205
Phe Thr Phe Asn Ser Gly Gln Arg Leu Gln Met His Ala Thr Gly Pro
    210                 215                 220
Glu Asn Gly Leu Ser Leu Ile Phe Ser Val Glu Lys Asp Asp Pro Leu
225                 230                 235                 240
Pro Gly Thr Tyr Gly Val Tyr Asn Phe Asp Asn Asn Ile Leu His Ser
                245                 250                 255
Ala Gly Val Arg Val Val His Ala Pro Gly Ser Met Pro Ser Pro
                260                 265                 270
Val Asp His Gly Ile Asp Ile Pro Pro Gly Tyr Ser Ser Ser Val Gly
    275                 280                 285
Leu Lys Ala Ile Leu His Thr Arg Leu Pro Tyr Pro Tyr Gly Asn Cys
    290                 295                 300
Thr Asn Asp Met Leu Asn Gly Ile Lys Gln Tyr Lys Tyr Thr Phe Phe
305                 310                 315                 320
Ala Cys Leu Gln Leu Cys Lys Gln Arg Leu Ile Ile Gln Arg Cys Gly
                325                 330                 335
Cys Lys Ser Ser Ala Leu Pro Glu Val Pro Ser Tyr Asn Ala Thr Phe
                340                 345                 350
Cys Gly Val Ile Lys Asp Trp Gln Glu Ile Asn Arg Asn His Ser Asn
                355                 360                 365
Glu Asp His Asn Gln Ser Glu Glu Asp Arg Ala Phe Ile Pro Thr Pro
                370                 375                 380
Tyr Leu Ala Cys Glu Glu Arg Glu Gln Lys Asn Leu Asn Asn Asp Arg
385                 390                 395                 400
Thr Tyr Glu Leu Ser Cys Gly Cys Phe Gln Pro Cys Ser Glu Thr Ser
                405                 410                 415
Tyr Leu Lys Ser Val Ser Leu Ser Tyr Trp Pro Leu Glu Phe Tyr Gln
                420                 425                 430
Leu Ser Ala Val Glu Arg Phe Phe Lys Gln Glu Arg Gln Ala Gly Gln
                435                 440                 445
Asn His Phe Met Lys Thr Ala Tyr Glu Tyr Leu Glu Lys Leu Ala His
    450                 455                 460
Pro Ser Gln Lys His Leu Ala Arg Asn Asp Ser His Met Asp Asp Ile
465                 470                 475                 480
Leu Ser Lys Ser Tyr Ser Leu Ser Glu Lys Glu Met Ala Lys Glu Ala
                485                 490                 495
Ser Asp Leu Ile Arg Gln Asn Met Leu Arg Leu Asn Ile Tyr Leu Glu
                500                 505                 510
Asp Leu Ser Val Val Glu Tyr Arg Gln Leu Pro Ala Tyr Gly Leu Ala
                515                 520                 525
Asp Leu Phe Ala Asp Ile Gly Gly Thr Leu Gly Leu Trp Met Gly Ile
                530                 535                 540
```

```
Ser Val Leu Thr Ile Met Glu Leu Ile Glu Leu Val Ile Arg Leu Thr
545                 550                 555                 560

Gly Leu Val Phe Asn Ser Glu Lys Gly Leu Pro Arg Gly Pro Thr Thr
                565                 570                 575

Val Asn Asn Asn Gly Ser Asn Asn His Ser Gln Ser Thr Ser Gln
            580                 585                 590

His Gln Leu Tyr Asn Gly Tyr Met Asp His Asp Ser His Tyr Ser Asp
        595                 600                 605

Ser Ala Gly Ala Ser Val Phe Asp Phe Arg Arg Gly Val Glu Ser Pro
        610                 615                 620

Val
625

<210> SEQ ID NO 16
<211> LENGTH: 564
<212> TYPE: PRT
<213> ORGANISM: C. elegans
<220> FEATURE:
<221> NAME/KEY: SITE
<222> LOCATION: (180)
<223> OTHER INFORMATION: Xaa represents 207 non-disclosed amino acids

<400> SEQUENCE: 16

Met Ser Trp Met Gln Asn Leu Lys Asn Tyr Gln His Leu Arg Asp Pro
 1               5                  10                  15

Ser Glu Tyr Met Ser Gln Val Tyr Gly Asp Pro Leu Ala Tyr Leu Gln
            20                  25                  30

Glu Asn Thr Lys Phe Val Thr Glu Arg Glu Tyr Tyr Glu Asp Phe Gly
        35                  40                  45

Tyr Gly Glu Cys Phe Asn Ser Ser Glu Ser Glu Val Gln Cys Glu Leu
    50                  55                  60

Ile Thr Gly Glu Phe Asp Pro Lys Leu Leu Pro Tyr Asp Lys Arg Leu
65                  70                  75                  80

Ala Trp His Phe Lys Glu Phe Cys Tyr Lys Thr Ser Ala His Gly Ile
                85                  90                  95

Pro Met Ile Gly Glu Ala Pro Asn Val Tyr Arg Ala Val Trp Val
            100                 105                 110

Met Leu Phe Leu Gly Cys Met Ile Met Leu Tyr Leu Asn Ala Gln Ser
        115                 120                 125

Val Leu Asp Lys Tyr Asn Arg Asn Glu Lys Ile Val Asp Ile Gln Leu
    130                 135                 140

Phe Lys Phe Asp Thr Ala Pro Phe Pro Ala Ile Thr Leu Cys Asn Leu
145                 150                 155                 160

Asn Pro Tyr Lys Ala Ser Leu Ala Thr Ser Val Asp Leu Val Lys Arg
                165                 170                 175

Thr Leu Ser Xaa Glu Ile Trp Thr Tyr Leu Gln Gly Gly Thr Pro Thr
        180                 185                 190

Glu Asp Pro Asn Phe Leu Glu Ala Met Gly Phe Gln Gly Met Thr Asp
    195                 200                 205

Glu Val Ala Ile Val Thr Lys Ala Lys Glu Asn Ile Met Phe Ala Met
210                 215                 220

Ala Thr Leu Ser Met Gln Asp Arg Glu Arg Leu Ser Thr Thr Lys Arg
225                 230                 235                 240

Glu Leu Val His Lys Cys Ser Phe Asn Gly Lys Ala Cys Asp Ile Glu
                245                 250                 255

Ala Asp Phe Leu Thr His Ile Asp Pro Val Phe Gly Ser Cys Phe Thr
```

-continued

```
                        260                 265                 270
Phe Asn His Asn Arg Thr Val Asn Leu Thr Ser Ile Arg Ala Gly Pro
                275                 280                 285

Met Tyr Gly Leu Arg Met Leu Val Tyr Val Asn Ala Ser Asp Tyr Met
        290                 295                 300

Pro Thr Thr Glu Ala Thr Gly Val Arg Leu Thr Ile His Asp Lys Glu
305                 310                 315                 320

Asp Phe Pro Phe Pro Asp Thr Phe Gly Tyr Ser Ala Pro Thr Gly Tyr
                325                 330                 335

Val Ser Ser Phe Gly Leu Arg Leu Arg Lys Met Ser Arg Leu Pro Ala
                340                 345                 350

Pro Tyr Gly Asp Cys Val Pro Asp Gly Lys Thr Ser Asp Tyr Ile Tyr
                355                 360                 365

Ser Asn Tyr Glu Tyr Ser Val Glu Gly Cys Tyr Arg Ser Cys Phe Gln
370                 375                 380

Gln Leu Val Leu Lys Glu Cys Arg Cys Gly Asp Pro Arg Phe Pro Val
385                 390                 395                 400

Pro Glu Gly Ala Arg His Cys Asp Ala Ala Asp Pro Val Ala Arg Arg
                405                 410                 415

Cys Leu Asp Ala Arg Met Asn Asp Leu Gly Gly Leu His Gly Ser Phe
                420                 425                 430

Arg Cys Arg Cys Gln Gln Pro Cys Gly Gln Ser Ile Tyr Ser Val Thr
                435                 440                 445

Tyr Ser Pro Ala Lys Trp Pro Ser Leu Ser Leu Gln Ile Gln Leu Gly
        450                 455                 460

Ser Cys Asn Gly Thr Ala Val Glu Cys Asn Lys His Tyr Lys Glu Asn
465                 470                 475                 480

Gly Ala Met Val Glu Val Phe Tyr Glu Gln Leu Asn Phe Glu Met Leu
                485                 490                 495

Thr Glu Ser Glu Ala Tyr Gly Phe Val Asn Leu Leu Ala Asp Phe Gly
                500                 505                 510

Gly Gln Leu Gly Leu Trp Cys Gly Ile Ser Phe Leu Thr Cys Cys Glu
                515                 520                 525

Phe Val Phe Leu Phe Leu Glu Thr Ala Tyr Met Ser Ala Glu His Asn
                530                 535                 540

Tyr Ser Leu Tyr Lys Lys Lys Ala Glu Lys Ala Lys Lys Val Ala
545                 550                 555                 560

Ser Gly Ser Phe
```

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: primer
<223> OTHER INFORMATION: "n" at positions 6, 9, 12, 15 & 16 represents "inosine", while "n" at position 18 represents A, T, C, G or unknown

<400> SEQUENCE: 17
ttyccngcnr tnacnntntg yaay                                          24

<210> SEQ ID NO 18
<211> LENGTH: 26
<212> TYPE: DNA
<213> ORGANISM: Artificial Sequence
<220> FEATURE:

<223> OTHER INFORMATION: Description of Artificial Sequence: primer
<223> OTHER INFORMATION: "n" at positions 3, 6, 9, 11 & 12 represents
      "inosine", while "n" at positions 15 & 18 represents A, T, C, G or
      unknown

<400> SEQUENCE: 18
canarnccna nntgnccncc dawrtc                                              26

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 19
attgctcttc ccatctctat                                                     20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 20
ttcaaggccc atacctaagt                                                     20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 21
cgattgcagt tcagcatctc t                                                   21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 22
accattcggc agccgcactt                                                     20